United States Patent
Connaris et al.

(10) Patent No.: US 11,466,059 B2
(45) Date of Patent: Oct. 11, 2022

(54) MODIFIED PROTEIN

(71) Applicant: Pneumagen Ltd, Fife (GB)

(72) Inventors: Helen Connaris, Fife (GB); Jane Alexandra Potter, Fife (GB)

(73) Assignee: Pneumagen Ltd, Fife (GB)

( * ) Notice: Subject to any disclaimer, the term of this patent is extended or adjusted under 35 U.S.C. 154(b) by 0 days.

(21) Appl. No.: 15/733,350

(22) PCT Filed: Jan. 9, 2019

(86) PCT No.: PCT/GB2019/050053
§ 371 (c)(1),
(2) Date: Jul. 8, 2020

(87) PCT Pub. No.: WO2019/138222
PCT Pub. Date: Jul. 18, 2019

(65) Prior Publication Data
US 2021/0070814 A1    Mar. 11, 2021

(30) Foreign Application Priority Data
Jan. 9, 2018   (GB) ..................................... 1800334

(51) Int. Cl.
| | | |
|---|---|---|
| *C07K 14/315* | (2006.01) | |
| *A61K 38/00* | (2006.01) | |
| *A61K 39/39* | (2006.01) | |
| *C07K 14/28* | (2006.01) | |
| *A61K 39/00* | (2006.01) | |

(52) U.S. Cl.
CPC .......... *C07K 14/3156* (2013.01); *A61K 38/00* (2013.01); *A61K 39/39* (2013.01); *C07K 14/28* (2013.01); *A61K 2039/55516* (2013.01)

(58) Field of Classification Search
None
See application file for complete search history.

(56) References Cited

FOREIGN PATENT DOCUMENTS

| | | |
|---|---|---|
| WO | 2010029312 A1 | 3/2010 |
| WO | 2015/110831 | 7/2015 |
| WO | 2018055365 A1 | 3/2018 |
| WO | 2018055370 A1 | 3/2018 |
| WO | 2018055373 A1 | 3/2018 |

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Ellis (Vaccines, W.B. Saunders Company, Chapter 29, 1988, pp. 568-574).*
Boslego et al (Vaccines and Immunotherapy, 1991, Chapter 17).*
International Search Report and Written Opinion corresponding to PCT/GB2019/050053; dated Feb. 26, 2019 (13 pages).
Alias, N. "Multivalent sialic acid binding proteins as novel therapeutics for influenza and parainfluenza infection" A Thesis, 2014, University of St. Andrews, 253 pages; retrieved from: http://hdl.handle.net/10023/4479.
Connaris et al. "Prevention of influenza by targeting host receptors using engineered proteins" PNAS, 111 (17):6401-6406 (2014).
Gov

MODIFIED PROTEIN

RELATED APPLICATIONS

This application is a 35 U.S.C. § 371 national stage application of PCT Application No. PCT/GB2019/050053, filed on Jan. 9, 2019, which claims priority from United Kingdom Patent Application No. 1800334.3, filed on Jan. 9, 2018, the contents of each of which are incorporated herein by reference in their entireties. The above-referenced PCT International Application was published in the English language as International Publication No. WO 2019/138222 A1 on Jul. 18, 2019.

FIELD OF THE INVENTION

The present invention provides novel sialic acid binding molecules and uses (including medical uses) of the same.

BACKGROUND

Sialic-acid binding carbohydrate binding modules (CBMs) (including those derived from *Vibrio cholerae* and *Streptococcus pneumoniae* and multi-valent forms thereof) have been shown to be effective antimicrobial agents with some shown to protect mice against a lethal challenge of H7N9 influenza virus. The biologic, Sp2CBMTD, contains two copies of a CBM Family 40 domain from *S. pneumoniae* neuraminidase A (SpCBM) genetically fused to the trimerization domain from *Pseudomonas aeruginosa* pseudaminidase (PaTD). The protein assembles via the trimerization domain to form an oligomer containing six copies of SpCBM.

However, with any protein-based therapeutic, there is a risk of adverse effects associated with the patient's immune responses to the biologic. In some cases, the biologic may induce the production of anti-drug antibodies (ADAs) which can result in the formation of immune complexes (ICs) between the ADA and the drug. The presence of such complexes may reduce the effectiveness or alter the half-life of the therapeutic, or could cause adverse effects such as hypersensitivity reactions.

There are a number of factors that influence the immunogenicity of a protein. One key determinant is the presence of intrinsic epitopes that can trigger T-cell dependent events that lead to antibody production. T-cells recognize short peptide fragments derived from the processing of the protein antigen that occurs within an antigen-presenting cell (APC). Some of these fragments will form complexes with human leukocyte antigen (HLA)/major histocompatibility complex (MHC) class II molecules, and, if bound stably enough, will be carried to the surface of the APC and presented to T-cells. The recognition of non-self peptide by the T-cell receptor triggers the subsequent immune response.

SUMMARY OF THE INVENTION

The present disclosure provides a novel cohort of sialic acid binding molecules.

The sialic acid binding molecules described herein may comprise one or more modified carbohydrate binding modules (CBMs).

As stated, with any protein-based therapeutic, there is the risk of adverse effects associated with the patient's immune responses to the biologic. The biologic may elicit the production of anti-drug antibodies (ADAs) which can result in the formation of immune complexes (ICs) between the ADA and the drug. The presence of such complexes may reduce the effectiveness, alter the half-life of the therapeutic or could cause adverse effects such as hypersensitivity reactions. The disclosed CBMs have been subject to modification so as to reduce the risk of these adverse effects.

Carbohydrate binding modules are classified into families and CBMs classed as members of the Family 40 CBMs (CBM40) may be useful in the manufacture of the modified molecules described herein. The Family 40 CBMs embrace molecules of approximately 200 residues and are often found at the N-terminus of GH33 sialidases. They may also be found inserted in the β-propeller of GH33 sialidases.

As such, the sialic acid binding molecules described herein may comprise one or more modified Family 40 carbohydrate binding modules (CBM40s).

Throughout this specification the term "comprising" is used to denote that embodiments "comprise" the noted features and as such, may also include other features. However, the term "comprising" may also encompass embodiments which "consist essentially of" the relevant features or "consist of" the relevant features.

In view of the above, the disclosure may embrace molecules, for example, larger molecules, which comprise a sialic acid binding component. As stated, that sialic acid binding component (i.e. the sialic acid binding molecule) may itself comprise (consist of or consist essentially of) a modified CBM, for example, a modified CBM40. By way of (non-limiting) example, the molecules of this disclosure may not only exhibit an ability to bind sialic acid, but may also have one or more other functions. For example, the molecules may have enzymatic activity. For example, a useful molecule may comprise a modified CBM (as described herein) and exhibit some sialidase activity.

In one embodiment, the CBM may not be provided as part of, or comprised within, a molecule with enzymatic (for example sialidase) activity.

A useful sialic acid binding molecule may be a fusion protein comprising an enzymatic portion and a sialic acid binding portion—wherein the sialic acid binding portion comprises a modified CBM as described herein. In such cases, the enzymatic portion may be fused to the sialic acid binding portion. As stated, the enzymatic portion of any useful fusion protein may comprise (or have, or exhibit) sialidase activity.

The term "modified" embraces molecules which contain one or more mutations relative to a reference sequence.

A "reference sequence" may be any wild type CBM sequence. For example, a reference sequence may comprise, consist essentially of or consist of a wild type family 40 CBM sequence, e.g. the wild type CBM sequences from *Vibrio cholerae* NanH sialidase or *Streptococcus pneumoniae* NanA sialidase (it should be appreciated that similar or homologous CBMs (including CBM40s) present in other organisms are to be encompassed within the scope of the term "CBM" and/or as CBM reference sequences).

Accordingly, a modified CBM sequence may be derived from a specific or particular wild type CBM.

A modified CBM sequence may comprise a wild type CBM sequence which includes one or more mutations.

The one or more mutations may be functional—that is to say they may individually (and/or independently) or collectively (for example, synergistically) modulate (alter, improve or suppress/inhibit) one or more of the physiological, biological immunological and/or pharmacological properties characteristic of a wild type CBM (for example the wild type CBM from which the modified CBM is derived). In particular, the one or more mutations may:

(i) alter the immunogenicity (or antigenicity) of the CBM; and/or
(ii) alter (for example improve) the efficacy (of the CBM or of any multimeric molecule comprising a modified CBM)' and/or
(iii) they may modulate (for example improve) the thermostability of the CBM; and/or
(iv) they may modulate (for example improve) the solubility of the CBM; and/or
(v) they may modulate (for example improve) the in vivo half-life of the molecule.

A "mutation" may include any alteration to the wild-type CBM molecule. For example, the term "mutation" may embrace, for example:
(i) one or more amino acid substitution(s) (where one or more of the wild type amino acid(s) is/are swapped or changed for another (different) amino acid—the term "substitutions" would include conservative amino acid substitutions); and/or
(ii) one or more amino acid deletion(s) (where one or more of the wild type amino acid residue(s) are removed); and/or
(iii) one or more amino acid addition(s)/insertion(s) (where additional amino acid residue(s) are added to a wild type (or reference) primary sequence); and/or
(iv) one or more amino acid/sequence inversions (usually where two or more consecutive amino acids in a primary sequence are reversed; and/or
(v) one or more amino acid/sequence duplications (where an amino acid or a part of the primary amino acid sequence (for example a stretch of 5-10 amino acids) is repeated)

As stated, a modified CBM according to this disclosure may comprise one or more of the mutations described herein.

An exemplary wild type CBM (in other words a reference sequence from which a useful modified CBM may be derived) is *Streptococcus pneumoniae* NanA sialidase—the amino acid sequence for which has been deposited under accession number P62575 and is reproduced below as SEQ ID NO: 1 (1035 amino acids).

```
                                                  SEQ ID NO: 1
MSYFRNRDID  IERNSMNRSV  QERKCRYSIR  KLSVGAVSMI

VGAVVFGTSP  VLAQEGASEQ  PLANETQLSG  ESSTLTDTEK

SQPSSETELS  GNKQEQERKD  KQEEKIPRDY  YARDLENVET

VIEKEDVETN  ASNGQRVDLS  SELDKLKKLE  NATVHMEFKP

DAKAPAFYNL  FSVSSATKKD  EYFTMAVYNN  TATLEGRGSD

GKQFYNNYND  APLKVKPGQW  NSVTFTVEKP  TAELPKGRVR

LYVNGVLSRT  SLRSGNFIKD  MPDVTHVQIG  ATKRANNTVW

GSNLQIRNLT  VYNRALTPEE  VQKRSQLFKR  SDLEKKLPEG

AALTEKTDIF  ESGRNGKPNK  DGIKSYRIPA  LLKTDKGTLI

AGADERRLHS  SDWGDIGMVI  RRSEDNGKTW  GDRVTITNLR

DNPKASDPSI  GSPVNIDMVL  VQDPETKRIF  SIYDMFPEGK

GIFGMSSQKE  EAYKKIDGKT  YQILYREGEK  GAYTIRENGT

VYTPDGKATD  YRVVVDPVKP  AYSDKGDLYK  GNQLLGNIYF

TTNKTSPFRI  AKDSYLWMSY  SDDDGKTWSA  PQDITPMVKA
```

-continued

```
DWMKFLGVGP  GTGIVLRNGP  HKGRILIPVY  TTNNVSHLNG

SQSSRIIYSD  DHGKTWHAGE  AVNDNRQVDG  QKIHSSTMNN

RRAQNTESTV  VQLNNGDVKL  FMRGLTGDLQ  VATSKDGGVT

WEKDIKRYPQ  VKDVYVQMSA  IHTMHEGKEY  IILSNAGGPK

RENGMVHLAR  VEENGELTWL  KHNPIQKGEF  AYNSLQELGN

GEYGILYEHT  EKGQNAYTLS  FRKFNWDFLS  KDLISPTEAK

VKRTREMGKG  VIGLEFDSEV  LVNKAPTLQL  ANGKTARFMT

QYDTKTLLFT  VDSEDMGQKV  TGLAEGAIES  MHNLPVSVAG

TKLSNGMNGS  EAAVHEVPEY  TGPLGTSGEE  PAPTVEKPEY

TGPLGTSGEE  PAPTVEKPEY  TGPLGTAGEE  AAPTVEKPEF

TGGVNGTEPA  VHEIAEYKGS  DSLVTLTTKE  DYTYKAPLAQ

QALPETGNKE  SDLLASLGLT  AFFLGLFTLG  KKREQ
```

The CBM region of SEQ ID NO: 1 is from amino acid residue 121 to 305—this sequence is designated SEQ ID NO: 2 (that sequence being: VIEKEDVETN ASNGQRVDLS SELDKLKKLE NATVHMEFKP DAKAPAFYNL FSVSSATKKD EYFTMAVYNN TATLEGRGSD GKQFYNNYND APLKVKPGQW NSVTFTVEKP TAELPKGRVR LYVNGVLSRT SLRSGNFIKD MPDVTHVQIG ATKRANNTVW GSNLQIRNLT VYNRALTPEE VQKRS).

Thus this disclosure provides sialic acid binding molecules which comprise modified forms of SEQ ID NO: 2 (and/or SEQ ID NO: 1). A modified form of SEQ ID NO: 2 may comprise one or more mutated residues—the mutations being, for example, amino acid substitutions, additions/insertions, duplications, deletions and/or inversions made relative to the sequence of SEQ ID NO: 2.

An exemplary *Vibrio cholerae* NanH sialidase amino acid sequence is deposited under accession umber A5F7A4 and is reproduced below as SEQ ID NO: 3 (781 amino acids).

```
                                                  SEQ ID NO: 3
MRFKNVKKTA  LMLAMFGMAT  SSNAALFDYN  ATGDTEFDSP

AKQGWMQDNT  NNGSGVLTNA  DGMPAWLVQG  IGGRAQWTYS

LSTNQHAQAS  SFGWRMTTEM  KVLSGGMITN  YYANGTQRVL

PIISLDSSGN  LVVEFEGQTG  RTVLATGTAA  TEYHKFELVF

LPGSNPSASF  YFDGKLIRDN  IQPTASKQNM  IVWGNGSSNT

DGVAAYRDIK  FEIQGDVIFR  GPDRIPSIVA  SSVTPGVVTA

FAEKRVGGGD  PGALSNTNDI  ITRTSRDGGI  TWDTELNLTE

QINVSDEFDF  SDPRPIYDPS  SNTVLVSYAR  WPTDAAQNGD

RIKPWMPNGI  FYSVYDVASG  NWQAPIDVTD  QVKERSFQIA

GWGGSELYRR  NTSLNSQQDW  QSNAKIRIVD  GAANQIQVAD

GSRKYVVTLS  IDESGGLVAN  LNGVSAPIIL  QSEHAKVHSF

HDYELQYSAL  NHTTTLFVDG  QQITTWAGEV  SQENNIQFGN

ADAQIDGRLH  VQKIVLTQQG  HNLVEFDAFY  LAQQTPEVEK

DLEKLGWTKI  KTGNTMSLYG  PIPFRWKSSS  ILETLEPSEA

DMVELQNGDL  LLTARLDFNQ  IVNGVNYSPR  QQFLSKDGGI
```

-continued

```
TWSLLEANNA NVFSNISTGT VDASITRFEQ SDGSHFLLFT

NPQGNPAGTN GRQNLGLWFS FDEGVTWKGP IQLVNGASAY

SDIYQLDSEN AIVIVETDNS NMRILRMPIT LLKQKLTLSQ N
```

The CBM region of SEQ ID NO: 3 is from amino acid residue 25 to 216—this sequence may be SEQ ID NO: 4 (that sequence being: ALFDYNATGD TEFDSPAKQG WMQDNTNNGS GVLTNADGMP AWLVQGIGGR AQWTYSLSTN QHAQASSFGW RMTTEMKVLS GGMITNYYAN GTQRVLPIIS LDSSGNLVVE FEGQT-GRTVL ATGTAATEYH KFELVFLPGS NPSASFYFDG KLIRDNIQPT ASKQNMIVWG NGSSNTDGVA AY)

Thus this disclosure provides sialic acid binding molecules which comprise modified forms of SEQ ID NO: 4 (and/or SEQ ID NO: 3). A modified form of SEQ ID NO: 4 may comprise one or more mutated residues—the mutations being, for example, amino acid substitutions, additions/insertions, duplications, deletions and/or inversions made relative to the sequence of SEQ ID NO: 4.

As stated, the sialic acid binding molecules described herein may comprise one or more (for example two or more) modified CBMs. Where the sialic acid binding molecules comprise two or more modified CBMs, the molecule may be referred to as a multivalent CBM. A sialic acid binding molecule which is (or which comprises) a multivalent CBM, may be prepared as a construct comprising the multiple (two or more) modified CBMs linked by amino acid/peptide linkers. Each modified CBM may be linked to another by, for example, peptides comprising 5, 10 or 15 amino acids. By way of example any one or more of the following peptides may be used to link two or more CBMs to produce a sialic acid binding molecule which is a multivalent CBM:

(i) 5 amino acid linkers:

```
ALXGS

LQALG

GGXSG

GGALG

GGSLG
```

(ii) 10 amino acid linkers:

```
ALXGSGGGSG

LQALGGGGSL
```

(iii) 15 amino acid linkers:

```
ALXGSGGGSGGGGSG
```

Where "X" is any amino acid.

The sialic acid binding molecules for use may further comprise one or more oligomerisation domain(s). Like the CBM component of the disclosed sialic acid binding molecules, the oligomerisation domains may be derived from wild type oligomerisation domains and may therefore comprise one or more mutations relative to a corresponding wild type oligomerisation domain sequence. Useful oligomerisation domains exhibit an ability to self-associate to form multimeric structures, for example, trimers. A modified oligomerisation domain for use may comprise any molecule with that same oligomerisation property. For the avoidance of doubt, the term "oligomerisation domain" as used herein embraces not only wild type oligomerisation domains, but also those that are modified (the "modified oligomerisation domains" disclosed herein).

For example, a sialic acid binding molecule according to this disclosure may comprise one or more (for example, two) CBMs (for example, one, two or more modified CBMs as described herein) bound, coupled or fused to an oligomerisation domain. The resulting sialic acid binding molecule is a (multimeric) CBM::oligomerisation domain "fusion".

Suitable oligomerisation domains may include those obtainable from the *Pseudomonas aeruginosa* pseudaminidase. An exemplary *Pseudomonas aeruginosa* pseudaminidase amino acid sequence has been deposited under accession number Q9L6G4 (derived from strain PAO579) and is reproduced below as SEQ ID NO: 13 (438 amino acids). It should be appreciated that similar, homologous or other useful oligomerisation domains may be encompassed within the scope of the general term "oligomerisation domain".

```
                                              SEQ ID NO: 13
MNTYFDIPHR LVGKALYESY YDHFGQMDIL SDGSLYLIYR

RATEHVGGSD GRVVFSKLEG GIWSAPTIVA QAGGQDFRDV

AGGTMPSGRI VAASTVYETG EVKVYVSDDS GVTWVHKFTL

ARGGADYNFA HGKSFQVGAR YVIPLYAATG VNYELKWLES

SDGGETWGEG STIYSGNTPY NETSYLPVGD GVILAVARVG

SGAGGALRQF ISLDDGGTWT DQGNVTAQNG DSTDILVAPS

LSYIYSEGGT PHVVLLYTNR TTHFCYYRTI LLAKAVAGSS

GWTERVPVYS APAASGYTSQ VVLGGRRILG NLFRETSSTT

SGAYQFEVYL GGVPDFESDW FSVSSNSLYT LSHGLQRSPR

RVVVEFARSS SPSTWNIVMP SYFNDGGHKG SGAQVEVGSL

NIRLGTGAAV WGTGYFGGID NSATTRFATG YYRVRAWI
```

The oligomerisation domain of SEQ ID NO: 13 is from amino acid residue 333 to 438—this sequence may be SEQ ID NO: 14 (that sequence being: VPDFESDWFS VSSNSLYTLS HGLQRSPRRV VVEFARSSSP STWNIVMPSY FNDGGHKGSG AQVEVGSLNI RLGTGAAVWG TGYFGGIDNS ATTRFATGYY RVRAWI).

As stated, the invention may exploit modified oligomerisation domains. A modified oligomerisation domain may comprise an oligomerisation domain which contains one or more mutations relative to a reference oligomerisation sequence.

A "reference oligomerisation sequence" may be any wild type oligomerisation domain sequence, including for example SEQ ID NOS: 13 and 14 above.

Accordingly, a modified oligomerisation domain may be derived from a specific or particular wild type oligomerisation domain.

A modified oligomerisation domain sequence may comprise a wild type oligomerisation domain sequence which includes one or more mutations.

The one or more mutations may be functional—that is to say they may individually (and/or independently) or collectively (for example synergistically) modulate (improve or suppress/inhibit) one or more of the physiological, immunological, biological and/or pharmacological properties characteristic of a wild type oligomerisation domain (for example the wild type oligomerisation domain from which the modified oligomerisation domain is derived). As stated above, the mutation(s) may
   (i) alter the immunogenicity (or antigenicity) of the oligomerisation domain; and/or
   (ii) improve efficacy (of, for example, multimeric molecules comprising one or more modified CBMs); and/or
   (iii) they may modulate (for example improve) the thermostability of the oligomerisation domain; and/or
   (iv) they may modulate (for example improve) the solubility of the oligomerisation domain; and/or
   (v) they may modulate (for example improve) the in vivo half-life of the oligomerisation domain.

In the context of a modified oligomerisation domain, the term "mutation" is as defined above.

In all cases, the mutations may modulate an immunological/antigenic property of a CBM or oligomerisation domain or a sialic acid binding molecule comprising the same.

There are a number of factors that influence the immunogenicity of a protein. One key determinant is the presence of intrinsic epitopes that can trigger T-cell dependent events that lead to antibody production. T-cells recognize short peptide fragments derived from the processing of the protein antigen that occurs within an antigen-presenting cell (APC). Some of these fragments will form complexes with human leukocyte antigen (HLA)/major histocompatability complex (MHC) class II molecules, and, if bound stably enough, will be carried to the surface of the APC and presented to T-cells. The recognition of non-self peptide by the T-cell receptor triggers the subsequent immune response. As such, in order to provide CBMs which are less immunogenic, wild type CBM and/or oligomerisation domains may be analysed in order to identify those regions which are immunogenic/antigenic (i.e. regions or domains which are likely to harbour or contain immunological epitopes). Immunogenicity (or antigenicity) is a property that may be assessed relative to, for example a particular human or animal host—in other words a CBM and/or oligomerisation domain may be analysed in order to determine which regions or domains may be immunogenic/antigenic in a specific (for example human) host. Immunogenicity (or antigenicity) may be assessed using, for example in silico in screening techniques (screening for, for example, T cell epitopes: including (as an example) ProPred in silico analysis), T-cell proliferation assays (including, Proimmune Human donor T-cell proliferation assay) and other immunological techniques. Further information regarding methods to "deimmunize" a protein may be derived from Jawa V, et al. ((2013) T-cell dependent immunogenicity of protein therapeutics: Preclinical assessment and mitigation. Clin Immunol. 149, 534-555) and Singh H, and Raghava G P ((2001) ProPred: prediction of HLA-DR binding sites. Bioinformatics. 17(12), 1236-7) the entire contents of which are incorporated by reference.

Using these techniques, it has been possible to identify immunogenic/antigenic regions of both the CBM and oligomerisation domains. FIG. 1 shows a complete analysis (ProPred predictions) of the antigenic regions within a SpCBM sequence (FIG. 1A) and a PaTD sequence (FIG. 1B). Predicted binders are coloured blue, with the first residue of each binding region shown in red. Predicted antigenic peptides (green bars) and Proimmune (purple bars) are shown under the sequences.

For example, within the SpCBM molecule, various regions between residues 127 to 300 (as shown in FIG. 1A) have been identified as harbouring immunogenic/antigenic domains. For example regions spanning residues 127-135, 146-154, 154-166, 158-166, 143-151, 149-157, 167-176, 167-178, 182-196, 188-196, 185-193, 204-212, 213-221, 220-228, 239-246, 239-254, 241-249, 242-249, 241-250, 241-251, 239-251, 239-249, 239-247, 246-254, 243-251, 257-265, 267-275, 284-300, 284-299, 284-297, 286-284, 286-300 and 289-296 have been identified as potentially immunogenic (some of which are predicted to bind a small number of alleles, whereas others are regarded as moderately or highly immunogenic).

More specifically and using the above described in silico and immunologic (T cell proliferation) assays) the regions spanning residues:

```
167 to 178 of SEQ ID NO: 1 (i.e. sequence:
FYNLFSVSSATK)

167 to 181 of SEQ ID NO: 1 (i.e. sequence:
FYNLFSVSSATKKDE)

239 to 251 of SEQ ID NO: 1 (i.e. sequence:
VRLYVNGVLSRTS)

236 to 250 of SEQ ID NO: 1 (i.e. sequence
KGRVRLYVNGVLSRT)

245 to 254 of SEQ ID NO: 1 (i.e. sequence:
GVLSRTSLRS)

286 to 294 of SEQ ID NO: 1 (i.e. sequence
IRNLTVYNR)
``` have been identified as immunogenic/antigenic. It should be noted that the region spanning residues 245 to 254 is identified representing an area of significant immunogenicity.

Within the PaTD oligomerisation domain, regions between residues 336 to 424 has been identified as harbouring immunogenic/antigenic domains. For example, the regions spanning residues 336-344, 340-348, 341-349, 348-356, 353-363, 355-363, 355-370, 362-370, 362-370/371, 375-383, 375-390, 400-407, 402-410, 397-405, 403-410 and 416-424 have been identified as potentially immunogenic (some of which are predicted to bind a small number of alleles, whereas others are regarded as moderately or highly immunogenic). By way of non-limiting example, residues 338 to 352 of SEQ ID NO: 13 have been identified as harbouring immunogenic/antigenic domains.

More specifically and using the above described in silico and immunologic (T cell proliferation) assays) the regions spanning residues:

```
340 to 349 of SEQ ID NO: 13 (i.e. sequence:
TNFSVSSNSLY)

351 to 359 of SEQ ID NO: 13 (i.e. sequence:
LSHGLQRSP)

398 to 406 of SEQ ID NO: 13 (i.e. sequence:
GSLNIRLGT)

392 to 406 of SEQ ID NO: 13 (i.e. sequence:
GAQVEVGSLNIRLGT)

338 to 352 of SEQ ID NO: 13 (i.e. sequence:
SDWFSVSSNSLYTLS)
``` have been identified as immunogenic/antigenic. It should be noted that the regions spanning residues 340-349, 351-359 and 398-406 were identified representing areas of significant immunogenicity.

Collectively, these regions (from both the CBM and oligomerisation domain) will be referred to as regions of "immunogenicity/antigenicity".

Accordingly, a modified CBM and/or oligomerisation for use can be generated by mutating (for example substituting, deleting, adding to, inverting and/or duplicating) one or more of the amino acid residues (or amino acid sequences) within, for example, the above identified regions of immunogenicity/antigenicity.

Thus, a modified CBM or oligomerisation domain according to this disclosure may comprise a modified immunogenicity (or antigenicity) profile. In other words, as compared to a wild type CBM or oligomerisation domain, a modified CBM/oligomerisation domain according to this disclosure may be less (or differently) immunogenic/antigenic in a human or animal host. One of skill will appreciate that mutations introduced to the primary amino acid sequence of a CBM or an oligomerisation domain, can modulate immunogenicity by rendering certain epitopes more or less immunogenic.

Thus, in one aspect, the invention provides a method of obtaining a CBM with a modified immunologic profile, said method comprising, determining which regions or domains of a CBM primary, secondary and/or tertiary amino acid sequence/structure are immunogenic and mutating one or more of the amino acid residues or sequences within one or more of the determined immunogenic/antigenic regions or domains.

Further, the invention provides a modified CBM obtainable by a method of obtaining a CBM with a modified immunologic profile (as described above).

Further, the disclosure provides a method of obtaining an oligomerisation domain with a modified immunologic profile, said method comprising, determining which regions or domains of an oligomerisation domain CBM primary, secondary and/or tertiary amino acid sequence/structure are immunogenic and mutating one or more of the amino acid residues or sequences within one or more of the determined immunogenic/antigenic regions or domains.

Further, the invention provides a modified oligomerisation domain obtainable by a method of obtaining an oligomerisation domain with a modified immunologic profile (as described above).

The disclosure further provides a method of obtaining a modified multimeric CBM. The method may comprise:
  obtaining at least one CBM with a modified immunologic profile as set out above; and optionally obtaining an oligomerisation domain with a modified immunologic profile as set our above; and
  creating a multimeric CBM which comprises at least one modified CBM.

CBM/oligomerisation domain immunogenicity/antigenicity may be subject to individual amino acid mutations. For example a specific amino acid residue may be replaced (substituted with another) or deleted. In order to predict the effect of any given mutation, a modified sequence (the sequence containing at least one mutation verses a reference sequence) may be fed into, for example, a program designed to identify immunogenic sequences (including for example MHC binding regions within an antigen sequence). One of skill will be familiar with suitable programs and systems—but ProPred is one example: the aim of this server is to predict MHC Class-II binding regions in an antigen sequence, using quantitative matrices derived from published literature by Sturniolo et. al., 1999. The server will assist in locating promiscuous binding regions.

The user will aim to identify those mutations that might have an effect on the immunogenicity/antigenicity of the CBM/oligomerisation domain but at the same time not affect the protein structure (which may be crucial to the sialic acid binding property of the CBM and to the oligomerisation property of the oligomerisation domain). For example, the modified CBM disclosed herein may maintain binding affinity for sialyllactose as assessed by, for example, surface plasmon resonance (SPR).

Based on the above and using the SpCBM molecule as an example, one or more of the following residues may be mutated:
  Residue(s) 167 (F), 168 (Y), 169 (N), 170 (L), 171 (F), 172 (S), 173 (V), 174 (S), 175 (S), 176 (A), 177 (T), 178 (K), 179 (K), 180 (D), 181 (E), 236 (K), 237 (G), 238 (R), 239 (V), 240 (R), 241 (L), 242 (Y), 243 (V), 244 (N), 245 (G), 246 (V), 247 (L), 248 (S), 249 (R), 250 (T), 251 (S), 252 (L), 253 (R), 254 (S), 286 (I), 287 (R), 288 (N), 289 (L), 290 (T), 291 (V), 292 (Y), 293 (N) and/or 294 (R)

Based on the above and using the PaTD as an example, one or more of the following residues may be mutated:
  Residue(s) 338 (S), 339 (D), 340 (W), 341 (F), 342 (S), 343 (V), 344 (S), 345 (S), 346 (N), 347 (S), 348 (L), 349 (Y), 350 (T), 351 (L), 352 (S), 353 (H), 354 (G), 355 (L), 356 (Q), 357 (R), 358 (S), 359 (P), 392 (G), 393 (A), 394 (Q), 395 (V), 396 (E), 397 (V), 398 (G), 399 (S), 400 (L), 401 (N), 402 (I), 403 (R), 404 (L), 405 (G) and/or 406 (T).

It should be noted, that the term "mutation" includes the addition of further amino acids(s) to any of the regions (the "immunogenicity/antigenicity regions) containing these residues. Further, the term "mutation" may include the duplication of any one or more amino acids and/or the inversion of any sequence within these regions. For example, short sequences of two or more (for example 3, 4, 5, 6, 7, 8, 9, 10, 11, 12, 13, 14 or 15 (or more)) amino acids may be inverted (and/or duplicated). Where the mutation is a substitution, the substituted amino acid may be any one of the other 19 naturally occurring amino acids or an artificial or synthetic amino acid. Further, the substituted amino acid may be a derivative or analogue of the wild type amino acid at the relevant position.

By way of non-limiting example and with reference to SpCBM, one or more the following mutations may be made (note, not all of these mutations may be directed at modulating the immunogenicity of a CBM)—for example, one or more of the mutations (including mutations M156F and M185I) may be used to modulate thermostability:

| | | |
|---|---|---|
| (i) | M156F | |
| (ii) | Y168W | (designated "Im15") |
| (iii) | L170A | (designated "Im16") |
| (iv) | L170T | (designated "Im17") |
| (v) | V173G | (designated "Im18") |
| (vi) | M185I | |
| (vii) | V239A | (designated "Im19") |
| (viii) | V239T | (designated "Im20") |
| (ix) | V246G | (designated "Im21") |
| (x) | I286A | (designated "Im22") |
| (xi) | Y292E | (designated "Im23") |

Further, and again by way of non-limiting example and with reference to the PaTD molecule, one or more of the following mutations may be made:

| | | |
|---|---|---|
| (i) | S342D | (designated "Im24") |
| (ii) | S345D | (designated "Im25") |
| (iii) | L348D | (designated "Im26") |
| (iv) | R403K | (designated "Im27") |

For the avoidance of doubt, any of CBM mutations listed as (i)-(xi) above and any of the PaTD mutations listed as (i)-(iv) may be made individually and/or in combination with one or more other of the listed mutations. For example, mutations at two or more of residues 156, 170 and 185 or 239, 246, 286 and 292 or 156, 170, 185, 239, 246, 286 and 292 may be combined. Additionally, or alternatively, mutations at residues 239 and 246 or 286 and 292 may be combined.

Further, the mutations listed above are examples only and it should be understood that any mutation at the noted positions which results in a CBM/oligomerisation domain having the desired properties (for example, reduced immunogenicity/antigenicity in a human host) is to be included within the scope of this invention.

Many techniques exist to allow one of skill in this field to introduce one or more amino acid mutations into a CBM or oligomerisation domain sequence. Any of those techniques may be used here and they include, for example, mutagenesis techniques, including: (site-) directed mutagenesis, PCR mutagenesis, insertional mutagenesis, signature tagged mutagenesis, transposon mutagenesis and/or sequence saturation mutagenesis. Gene synthesis techniques may also be used to introduce any one or more of the mutations described herein.

Prior to any mutagenesis procedures, a wild type CBM and/or oligomerisation domain nucleic acid sequence may be subject to a codon-optimisation process in which the codons are optimised for expression in an expression system, such as, for example, a bacterial (e.g. an *E. coli*) expression system.

While useful sialic acid binding molecules may comprise a monomeric modified CBM (i.e. a single modified CBM), others may be multimeric—in other words, molecules which comprise two or more CBMs (for example, two or more modified CBMs). In such cases, the sialic acid binding molecule may be referred to as a "multimeric CBM". Sialic acid binding molecules, which comprise a plurality of CBMs, may comprise two or more modified CBMs wherein some but not all of the CBMs within the sialic acid binding molecule are modified. In other words, a sialic acid binding molecule, which comprises two or more CBMs, may comprise a mixture of modified and non-modified CBMs.

In one embodiment, the sialic acid binding molecules may comprise hexameric CBMs. A hexameric CBM comprises six CBM monomers. In most cases, a hexameric CBM comprises two fused CBMs which are further conjugated to themselves via a fused oligomerisation (trimerisation) domain.

By way of example, the generic structure of a useful hexameric CBM molecules may be represented as:

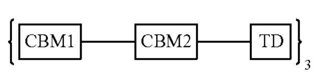

The schematic (and generic) structure above shows a sialic acid binding molecule comprising three repeat units each comprising 2 CBMs (CBM1 and CBM 2) and an oligomerisation domain (in this case, a trimerisation domain: TD).

As described herein, one or both of the CBM moieties may be a modified CBM as described herein. Each repeat unit may be the same or different—in other words, while each of the repeat units may comprise 2 CBMs (modified or otherwise). The type of CBM and/or the level or degree of modification, may vary. By way of non-limiting example, one repeat unit may contain two CBMs with wild type sequences. Another may comprise two different CBMs one with a wild type sequence and one with a modified sequence (comprising one or more mutations as described herein). The third repeat unit may comprise two modified CBMs (comprising one or more of the mutations described herein). One of skill will appreciate that other combinations of CBM type and/or sequence (wild type vs mutated sequence) may be prepared and tested.

By way of non-limiting example, the following represent individual units (referred to as "HEX" units) which may be used to make hexameric sialic acid binding molecules. In each case, the HEX unit comprises two modified CBMs (denoted CBM1 and CBM 2) with the specific mutations introduced to each CBM being identified in parenthesis. It should be noted that a "----" symbol indicates an amino acid linker (linking one CBM to another or a CBM to an oligomerisation domain). As such, a hexameric sialic acid binding molecule may be made up of several (for example 3) HEX units. In each case, the oligomerisation domain (denoted "TD") conjugates the units together as a trimer. While any given hexamer may comprise identical copies of the units described above (and below) under the headings HEX1, HEX2, HEX3, HEX4, HEX5, HEX6 and HEX17, one of skill will appreciate that further options are available. For example, a HEX unit may be made up of two CBMs, each having different mutations (the mutations being one or more selected from the options detailed herein).

```
(i) HEX1
CBM1 (L170T V239A V246G I286A Y292E)-----CBM2

(L170T V239A V246G I286A Y292E)-----TD (S342D

L348D R403K)

(ii) HEX2
CBM1 (V239A V246G I286A Y292E)----CBM2 (V239A

V246G I286A Y292E)----TD (S342D R403K)

(iii) HEX3
CBM1 (V239A V246G I286A)-----CBM2 (V239A V246G

I286A)-----TD (S342D R403K)

(iv) HEX4
CBM1 (V239A V246G)-----CBM2 (V239A

V246G)-----TD (S342D)

(v) HEX5
CBM1 (V239A V246G)-----(V239A V246G)-----TD (R403K)

(vi) HEX6
CBM1 (V239A V246G)-----CBM2 (V239A

V246G)-----TD (S342D R403K)

(vii) HEX17
CBM1 (V239A V246G A162P)-----CBM2 (V239A V246G

A162P)-----TD (S342D R403K)
```

It will be noted that HEX6 and HEX17 are identical except for the additional A162P mutation. This proline mutation (a substitution for the wild type Alanine at residue 162) has been shown to improve thermostability (the single CBM Tm by 3-4° C.). Further information regarding the use of proline mutations may be derived from Fu 2009, 'Increasing protein stability by improving beta-turns' (DOI 10.10021/prot.22509) describes the general approach. The proline mutation does not affect (increase or decrease) the predicted immunogenicity of the CBM molecule, is not located near the other mutations, the N- or C-termini or the ligand binding site. Rather unexpectedly, beyond the modest improvement in thermostability, it was noted that the A162P mutation yields hexameric CBMs (i.e. HEX17) exhibiting a marked improvement in in vivo experiments—in particular in comparison to those same experiments conducted using HEX6. For example, the modified molecules (in particular a molecule comprising 3×HEX17 units) exhibit modulation over pro-inflammatory cytokines, including for example IL-8. Indeed, the modulatory effect (specifically an inhibitory effect) on the production of IL-8 by a molecule comprising 3×HEX17 units, was improved over other tested modified molecules.

Relative to the amino acid sequences of Sp2CBMTD (aka "SpOrig") the amino acid sequence of the HEX6 and HEX 17 molecules is:

human subjects, suffering from, or at risk of contracting, a disease and/or condition caused or contributed to by a pathogen, particularly those pathogens which are capable of binding cell surface sialic acid-containing receptors. For example, the term "pathogen" may encompass any pathogen which is capable of binding, recognising or otherwise associating with a cell surface carbohydrate; especially those pathogens which have evolved to exploit or utilise the presence of cell surface (sialic acid) carbohydrates as a means of binding/adhering to and/or entering a cell. As such, the term "pathogen" may embrace microbial pathogens and may include respiratory pathogens such as viruses belonging to the Orthomyxoviridae or Paramyxoviridae families, for example, influenza and human parainfluenza, as well as bacteria belonging to the *Streptococcus* genus (such as *Streptococcus pneumoniae*) and/or *Haemophilus influenzae, Pseudomonas aeruginosa*—all of which are capable of binding carbohydrates on the surface of mammalian cells.

```
SpOrig   GAMVIEKEDVETNASNGQRVDLSSELDKLKKLENATVHMEFKPDAKAPAFYNLFSVSSAT
HEX6     GAMVIEKEDVETNASNGQRVDLSSELDKLKKLENATVHMEFKPDAKAPAFYNLFSVSSAT
HEX17    GAMVIEKEDVETNASNGQRVDLSSELDKLKKLENATVHMEFKPDPKAPAFYNLFSVSSAT SpOrig   KKDEYFTMAVYNNTATLEGRGSDGKQFYNNYNDAPLKVKPGQWNSVTFTVEKPTAELPKG
HEX6     KKDEYFTMAVYNNTATLEGRGSDGKQFYNNYNDAPLKVKPGQWNSVTFTVEKPTAELPKG
HEX17    KKDEYFTMAVYNNTATLEGRGSDGKQFYNNYNDAPLKVKPGQWNSVTFTVEKPTAELPKG SpOrig   RVRLYVNGVLSRTSLRSGNFIKDMPDVTHVQIGATKRANNTVWGSNLQIRNLTVYNRALT
HEX6     RARLYVNGGLSRTSLRSGNFIKDMPDVTHVQIGATKRANNTVWGSNLQIRNLTVYNRALT
HEX17    RARLYVNGGLSRTSLRSGNFIKDMPDVTHVQIGATKRANNTVWGSNLQIRNLTVYNRALT SpOrig   PEEVQKRSGGGSGVIEKEDVETNASNGQRVDLSSELDKLKKLENATVHMEFKPDAKAPAF
HEX6     PEEVQKRSGGGSGVIEKEDVETNASNGQRVDLSSELDKLKKLENATVHMEFKPDAKAPAF
HEX17    PEEVQKRSGGGSGVIEKEDVETNASNGQRVDLSSELDKLKKLENATVHMEFKPDPKAPAF SpOrig   YNLFSVSSATKKDEYFTMAVYNNTATLEGRGSDGKQFYNNYNDAPLKVKPGQWNSVTFTV
HEX6     YNLFSVSSATKKDEYFTMAVYNNTATLEGRGSDGKQFYNNYNDAPLKVKPGQWNSVTFTV
HEX17    YNLFSVSSATKKDEYFTMAVYNNTATLEGRGSDGKQFYNNYNDAPLKVKPGQWNSVTFTV SpOrig   EKPTAELPKGRVRLYVNGVLSRTSLRSGNFIKDMPDVTHVQIGATKRANNTVWGSNLQIR
HEX6     EKPTAELPKGRARLYVNGGLSRTSLRSGNFIKDMPDVTHVQIGATKRANNTVWGSNLQIR
HEX17    EKPTAELPKGRARLYVNGGLSRTSLRSGNFIKDMPDVTHVQIGATKRANNTVWGSNLQIR SpOrig   NLTVYNRALTPEEVQKRSGGALGVPDFESDWFSVSSNSLYTLSHGLQRSPRRVVVEFARS
HEX6     NLTVYNRALTPEEVQKRSGGSLGVPDFESDWFDVSSNSLYTLSHGLQRSPRRVVVEFARS
HEX17    NLTVYNRALTPEEVQKRSGGSLGVPDFESDWFDVSSNSLYTLSHGLQRSPRRVVVEFARS SpOrig   SSPSTWNIVMPSYFNDGGHKGSGAQVEVGSLNIRLGTGAAVWGTGYFGGIDNSATTRFAT
HEX6     SSPSTWNIVMPSYFNDGGHKGSGAQVEVGSLNIKLGTGAAVWGTGYFGGIDNSATTRFAT
HEX17    SSPSTWNIVMPSYFNDGGHKGSGAQVEVGSLNIKLGTGAAVWGTGYFGGIDNSATTRFAT SpOrig   GYYRVRAWI
HEX6     GYYRVRAWI
HEX17    GYYRVRAWI
```

Without wishing to be bound by any particular use or application, the disclosed molecules may be useful:
(i) in the treatment and/or prevention of diseases in a subject in need thereof;
(ii) in modulating immune responses (in human or animal subjects);
(iii) in modulating cell growth, proliferation and/or differentiation
(iv) as adjuvants; and/or
(vi) in the manufacture of medicaments.

Again, without wishing to be bound by any specific use, the disclosed molecules may be used (as medicaments) in the treatment and/or prevention of a variety of diseases and or conditions—in particular, diseases or conditions caused or contributed to by a pathogen, particularly those pathogens which are capable of binding cell surface sialic acid-containing receptors. The present disclosure may also provide methods useful in the treatment of subjects, particularly One of skill will appreciate that the mammalian cell most frequently colonised/infected by pathogens of the type described herein, are epithelial cells, especially those lining the mucosal tracts (for example, respiratory epithelial cells). For a full disclosure of how sialic acid binding molecules can be used to treat or prevent disease, see PCT/GB2009/002189, the entire contents of which are incorporated herein by reference.

In terms of modulating immune responses (in human or animal subjects), the various sialic acid binding molecules described herein (which molecules comprise one or more modified CBMs) have immunomodulatory properties. For example (and without wishing to be bound by theory), the disclosed sialic acid binding molecules modulate host immune responses, prime the immune system, modulate (e.g. increase or decrease) the expression, function and/or activity of immune system processes, pathways and/or any component(s) thereof. The term "priming" as applied to an immune response, may encompass the phenomenon of increasing the readiness and/or responsiveness of an immune system to an immunogen, antigen, pathogen, disease or infection. Without wishing to be bound by theory, in addition to any immunomodulatory properties associated with the sialic acid binding molecules disclosed herein, subjects administered or contacted with the disclosed sialic acid binding molecules may be rendered better able to cope with the onset of an infection/disease. For a full disclosure of the immunomodulatory activity of sialic acid binding molecules see PCT/GB2015/050161 the entire contents of which are incorporated herein by reference.

Further, it has been shown that the disclosed sialic acid binding molecules (which molecules may contain one or more modified CBMs) may be used to modulate aspects of cell growth and/or cell activity. The terms "growth" and "activity" as applied to cells may embrace processes and/or phenomena associated with one or more of cell proliferation, cell viability, cell migration, cell metabolism, cell differentiation and/or cell morphology/phenotype. The terms "growth" and/or "activity" may further include the response of a cell to certain exogenous and/or endogenous factors or stimuli including, for example, responses to certain compounds of the immune system, cytokines, chemokines and one or more environmental factors (light, temperature, pressure, mechanical stress and the like). Thus, the sialic acid binding molecules disclosed herein may be used to modulate (inhibit, decrease or increase) levels of cell responsiveness. Accordingly, any of the disclosed molecules may be used in the treatment or prevention of a disease and/or condition caused, contributed to and/or characterised by aberrant cell growth and/or activity or in the manufacture of a medicament to treat or prevent the same.

Without wishing to be bound to any particular medical application, it should be noted that diseases which are caused, contributed to or characterised by aberrant cell growth and/or activity may include, for example cell proliferation and/or differentiation disorders including, those referred to or classified as benign or malignant conditions. For example, the term "cell proliferation and/or differentiation disorders" may include those diseases and/or conditions collectively referred to as "cancer". The term "cancer" may include, but is not limited to, those cancers referred to as forms of breast cancer, bone cancer, brain cancer (gliomas), pancreatic cancer, lung cancer, prostate cancer, skin cancer, ovarian cancer, cervical cancer, head and neck cancers and bowel/colon cancer. The term "cancer" may also include those diseases and/or conditions collectively referred to as "leukaemias" (both chronic and acute) and any cancer affecting a mucosal/mucosal associated surface or tissue.

As such, a sialic acid binding molecule described herein, which molecule may comprise one or more modified CBMs, may find application (i.e. may be for use) in the treatment and/or prevention of cancer. The disclosed sialic acid binding molecules may further be used in the manufacture of a medicament for the treatment and/or prevention of cancer. For a full disclosure of how sialic acid binding molecules can be used to modulate cell growth and/or cell activity, see PCT/GB2017/052808 the entire contents of which are incorporated herein by reference.

Any of the disclosed sialic acid binding molecules (comprising one or more modified CBMs) may be used as adjuvants which themselves may be used in combination with one or more antigens to augment, modulate or enhance a host immune response to the one or more antigens. It should be noted that while the sialic acid binding molecule-based adjuvants disclosed herein can be combined with any type of antigen, the adjuvants, which are the subject of this disclosure may be particularly useful as mucosal adjuvants—in other words, for use with antigens that are to be administered mucosally. For a full disclosure of how sialic acid binding molecules can be used as adjuvants, see PCT/GB2017/052805 the entire contents of which are incorporated herein by reference.

It has also been shown that the disclosed sialic acid binding molecules (which molecules may contain one or more modified CBMs) may find utility in the treatment and/or prevention of sepsis. The term "sepsis" is applied to a number of diseases, conditions and/or syndromes which may have an infectious (for example viral, bacterial and/or fungal) aetiology. For example, term "sepsis", may embrace those disease states, conditions or syndromes referred to as SIRS (systemic inflammatory response syndrome: see Singer et al, 2016: JAMA "The third International consensus definitions for sepsis and septic shock), sepsis (which is often defined as "SIRS in response to an infectious process"), severe sepsis (that is sepsis with sepsis-induced organ dysfunction or tissue hypoperfusion (which itself might manifest as hypotension, elevated lactate or decreased urine output) and septic shock (severe sepsis plus persistently low blood pressure despite, for example, the administration of intravenous fluids). The term "sepsis" is most often applied to diseases, conditions and/or syndromes which result from "bacterial sepsis". Bacterial sepsis may stem from the presence of bacteria in blood and may sometimes be referred to as "bacteraemia" or "septicaemia". The term "sepsis" may also embrace diseases and/or conditions which are caused or contributed to by the presence of bacterial components such as LPS, toxins and/or membrane fragments in the blood. Components of this type may originate from primary infections present in other tissues and/or organs, for example, infections present in the lungs, brain, skin, urinary tract, pelvis and/or abdomen.

For a full disclosure of how sialic acid binding molecules can be used in the treatment and/or prevention of sepsis, see PCT/GB2017/052800 the entire contents of which are incorporated herein by reference The modified CBMs described herein and any molecules comprising the same may be conjugated, bound or joined to or associated with, other entities for the purpose of targeting or delivering that entity to some tissue or cell. Molecules of this type may be otherwise known as "therapeutic warheads" or "conjugates". Without wishing to be bound by theory, the presence of ligands for the various modified CBMs which may be comprised within the molecules of this disclosure, in certain cell receptors and membrane bound molecules, may allow the various molecules described herein to be exploited as a means to deliver conjugated heterologous molecules (these being molecules which are distinct from and different to the modified CBM or molecule comprising the same) to said cells or tissues comprising said cells. Such conjugated molecules may be useful in the treatment of a variety of diseases including, for example, cancer, where the conjugated molecules described herein (which molecules exhibit affinity for carbohydrates expressed on the surface of cells) may be used to direct therapeutic and/or cytotoxic moieties thereto.

By way of example, a molecule as described herein (including any of the modified CBMs or molecules comprising the same) may be conjugated to one or more (for example two, three, four or more) moieties which are, for example, therapeutic and/or cytotoxic.

Useful molecules may comprise a modified CBM of this disclosure conjugated (joined, bound or otherwise associated with) to a heterologous moiety. The heterologous moiety may comprise a therapeutic and/or cytotoxic moiety which may be conjugated to some part of the modified CBM molecule.

For example, the heterologous moiety may be conjugated to one or both ends of a modified CBM molecule. The heterologous moiety may be additionally or alternatively conjugated (or even fused) to an internal portion of a modified CBM molecule. It will be appreciated that however the heterologous moiety is to be conjugated to the modified CBM molecule, the molecule (nor its conjugation) should not (substantially) interfere with or ablate or reduce the carbohydrate (sialic acid) binding property of the modified CBM molecule.

As stated, the heterologous moiety may be a drug useful in the treatment of a disease which affects a cell or tissue expressing a receptor which comprises the ligand for any one of the modified CBMs (or molecules comprising the same) described herein. For example, the drug may be a chemotherapeutic drug for use in the treatment of cancer and the like. The heterologous moiety may be a cytotoxic moiety capable of killing or inducing apoptosis in, a cell. The heterologous moiety may comprise a molecule which is able to recruit specific cells to or into a particular tissue. For example, the heterologous moiety may be, for example, a T cell receptor (TCR) which may be used as a means to recruit T cells to, for example a tumour or cancerous tissue.

The present disclosure may provide compositions for application in the various uses, medicaments and methods described herein. As such, any of the modified CBMs described herein (or any molecule comprising a modified CBM) may be formulated for use.

For convenience, and with reference to the section below describing compositions, formulations and the like, it should be noted that both molecules comprising a modified CBM as described herein, a molecule comprising the same and any conjugates comprising the same (for example modified CBM::drug conjugates/fusions) shall be included under the general term “molecule comprising a modified CBM”.

A molecule comprising a modified CBM may be formulated for use as a therapeutic or pharmaceutical composition. The various compositions may comprise one or more of the molecules described herein and any given treatment may require the administration (together, concurrently or separately) of one or more of these compositions. It should be noted that a composition according to this disclosure may further comprise one or more other therapeutic moieties—for example molecules, small molecules, antibodies, oligonucleotides and the like useful in the treatment of one or more diseases and/or conditions. Additionally, or alternatively, the modified CBMs may be administered together with one or more other (different) therapeutic entities—wherein the one or more other (different) therapeutic entities may be used for the treatment of the same or a different disease. The term “administered together” embraces administration of a modified CBM before, after and/or at the same time as the administration of the one or more other therapeutic entities.

The molecules described herein may be formulated for enteral (including oral), parenteral and/or topical administration and one of skill will appreciate that the precise formulation may vary depending on the route of administration.

Pharmaceutical compositions according to the present invention may be prepared conventionally, comprising substances that are customarily used in pharmaceuticals and as described in, for example, Remington’s The Sciences and Practice of Pharmacy, 22nd Edition (Pharmaceutical Press 2012) and/or Handbook of Pharmaceutical Excipients, 7th edition (compiled by Rowe et al, Pharmaceutical Press, 2012)—the entire content of all of these documents and references being incorporated by reference.

A therapeutic or pharmaceutical composition of this disclosure (that is a composition comprising a molecule comprising a modified CBM and for use in any of the medicaments or methods described herein) may be formulated together with one or more pharmaceutically acceptable excipients, carriers, adjuvants and buffers. The compositions can be administered, e.g. orally (including mucosally), parentally, enterally, intramuscularly, subcutaneously, intravenously or via any other routes useful to achieve the desired effect (for example the modulation of cell growth/activity, treatment or prevention of diseases/conditions associated with the same and/or cancer and/or modulation of tumour growth). As stated, depending on the chosen route of administration, the exact composition of the formulation may vary.

A therapeutic or pharmaceutical formulation comprising a molecule comprising a modified CBM and for administration to a subject may be coated, encapsulated or enveloped in a material which protects the molecule from the action of enzymes, acids and other natural compounds/conditions (including, for example, compounds (including antibodies), cells and processes of the immune system) which may inactivate or denature the compound and/or its carbohydrate binding properties.

Among the various standard and conventional excipients that may be available for use in compositions comprising the molecules described herein, are those pharmaceutically acceptable organic or inorganic carrier substances which are suitable for parenteral, enteral, oral (including mucosal) and other routes of administration that do not deleteriously react with the molecule(s) comprising a modified CBM.

Where molecules comprising a modified CBM are to be formulated for parental administration, the compositions may be sterile.

The composition may comprise an oil-based or aqueous solution, a suspension and/or an emulsion.

In other embodiments, the composition may take the form of an implant, such as for example a (dissolvable or biodegradable) film, pessary or implant (including suppositories).

The pharmaceutical preparations comprising the molecules described herein may be mixed with stabilizers, wetting agents, emulsifiers, salts (for use in influencing osmotic pressure), buffers and/or other substances that do not react deleteriously with the active compounds.

One or more of the molecules described herein may be formulated for and administered, orally. As stated, oral administration would include mucosal administration which would itself would include administration intranasally and/or by inhalation.

Compositions for use may include solid dosage forms which are suitable for oral administration. These may include, for example capsules, tablets, pills, powders, and granules. In any given solid dosage form, a molecule comprising a modified CBM (or any molecule or conjugate comprising the same) may be admixed with at least one inert pharmaceutically-acceptable excipient. Examples of suitable excipients will be known to one of skill in this field but may include, for example fillers or extenders, humectants, wetting agents, binders, disintegrating agents, solution retarders, absorption accelerators, adsorbents, lubricants or mixtures thereof. A tablet, pill or capsule may further comprise a buffering agent. Solid dosage forms such as tablets, dragees, capsules, pills and/or granules also can be prepared with coatings and shells, such as coatings which protect against the gastrointestinal environment and/or stomach acid.

A solid dosage form may contain opacifying agents, and can also be formulated so as to ensure the delayed release of the active agent (in this case a molecule comprising a modified CBM or a conjugate comprising the same) in or to a specific part of the intestinal tract.

Solid compositions for oral administration can be formulated in a unit dosage form, each dosage containing an appropriate dose of a molecule comprising a modified CBM (or conjugate comprising the same). The exact amount of a molecule comprising a modified CBM (or conjugate comprising the same) contained within any given solid dosage form will vary depending on the intended use. A solid composition may contain a "unit dose"—a unit dose containing a quantity of a molecule comprising a modified CBM (or conjugate containing the same) calculated to produce the desired effect (for example modulation of cell growth and/or activity) over the course of a treatment period.

Liquid dosage forms for oral administration may (as stated) include emulsions, solutions, suspensions, syrups, and elixirs. In addition to the compound or composition, the liquid dosage forms may contain inert diluents commonly used in the art, such as water or other solvents, solubilizing agents and emulsifiers.

Any of the disclosed molecules may be used in any suitable amount. As stated, the molecules may be formulated for oral, mucosal or parenteral administration and as such, the precise formulation may depend on the intended route of administration and/or physiological and/or other attributes of the subject. The amount of a molecule comprising a modified CBM present in any given dose may be in the region of 0.1 µg-1000 µg. For example, amounts of about 0.1 µg, 0.2 µg, 0.3 µg, 0.4 µg, 0.5 µg, 1 µg, 10 µg, 20 µg, 25 µg, 50 µg, 100 µg, 200 µg, 300 µg, 400 µg, 500 µg, 600 µg, 700 µg, 800 µg or 900 µg. Higher amounts of modified CBM (or a molecule comprising the same) may be used; for example, amounts in the region of 1 mg-10 mg, for example amounts of about 1 mg, 2 mg, 3 mg, 4 µg, 5 mg, 6 mg, 7 mg, 8 mg or 9 mg. The selected amount of the modified CBM molecule may be formulated in a specific volume of a pharmaceutically acceptable excipient, diluent and/or buffer. The volume of excipient, diluent or buffer may be about 10 µl to 5 ml. For example, the required amount of CBM32/47/67/70 molecule may be combined (or formulated) with about 15 µl, 20 µl, 25 µl, 30 µl, 35 µl, 40 µl, 45 µl, 50 µl, 55 µl, 60 µl, 65 µl, 70 µl, 75 µl, 80 µl, 85 µl, 90 µl, 95 µl, 100 µl, 200 µl, 250 µl, 300 µl, 400 µl, 500 µl, 600 µl, 700 µl, 800 µl, 900 µl, 1 ml, 2 ml, 3 ml or 4 ml. Doses at concentrations of about 0.1 µg/ml-10 mg/ml may be used including, for example, doses at 5 µg/ml, 10 µg/ml, 20 µg/ml, 25 µg/ml, 50 µg/ml, 100 µg/ml, 200 µg/ml, 300 µg/ml, 500 µg/ml, 600 µg/ml, 700 µg/ml, 800 µg/ml or 900 µg/ml, 950 µg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml or 9.5 mg/ml.

In use, a dose of a modified CBM molecule, administered as part of the treatment and/or prevention of a disease (for example a cell proliferation and/or differentiation disorder or cancer), may be administered multiple times over a number of days, weeks months or years. For example, after an initial (or first) administration, a dose of a modified CBM molecule may be administered again at about (+/−1 or 2 days) 3, 4, 5, 6, 7, 8, 9, 10, 11, 12, 13, 14, 15, 16, 17, 21, 28 and/or 35 days later. Multiple repeat doses may be given at regular intervals—for example every 2, 3, 4, 5, 6, 7, 8, 9, 10, 11, 12, 13, 14, 15, 16, 17, 18, 19, 20, 21, 22, 23, 24, 25, 26, 27 or 28 day(s) after a preceding dose. On any given day, a specific dose of a modified CBM molecule may be administered 1, 2, 3 or more times. Each time, the modified CBM molecule may be administered (by whatever route is considered best) to affect a suitable treatment or to induce prophylaxis against a particular disease or condition.

DETAILED DESCRIPTION

The present invention will now be described in detail with reference to the following figures which show:

Figure 1A:
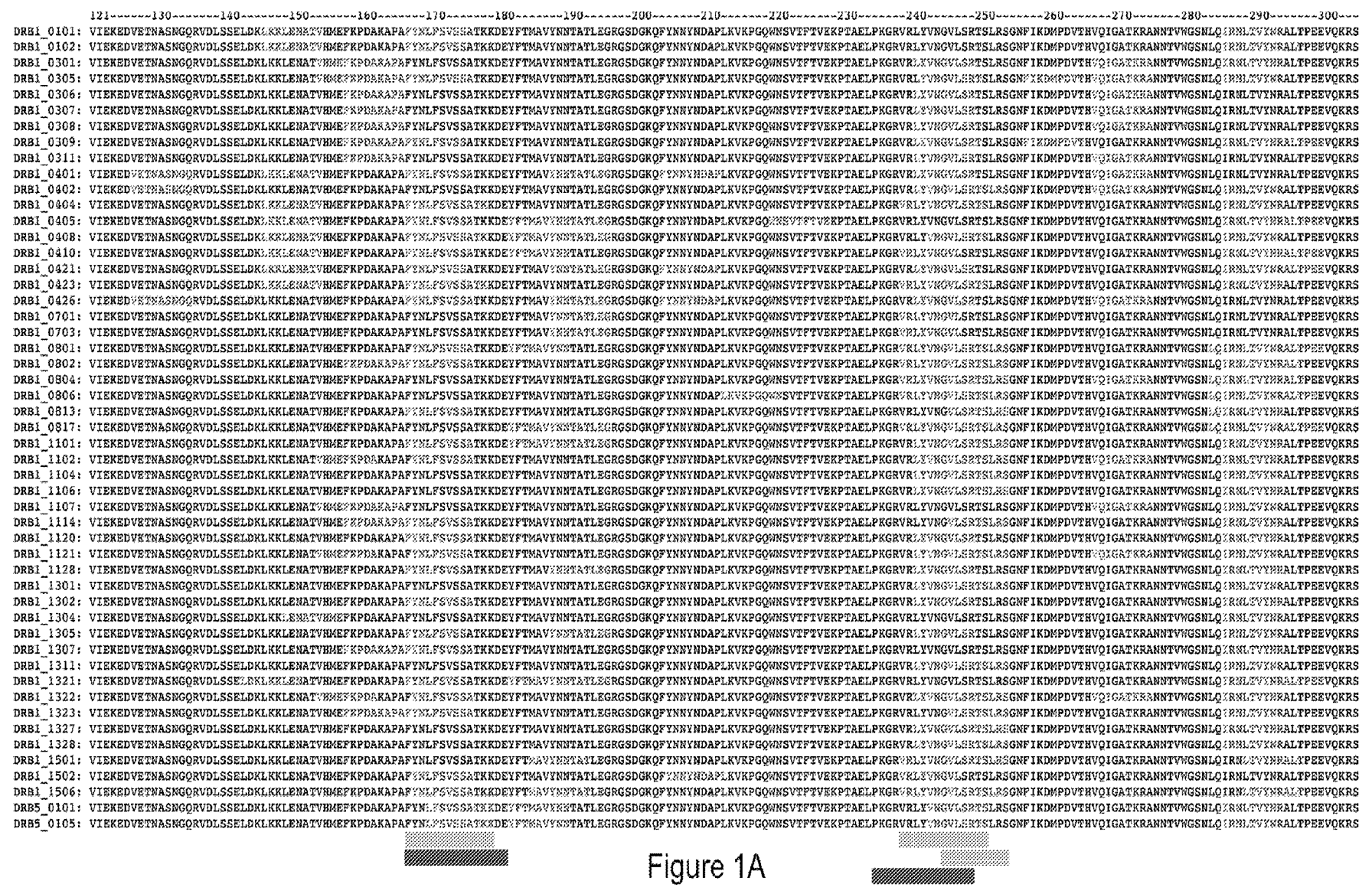
Figure 1B:
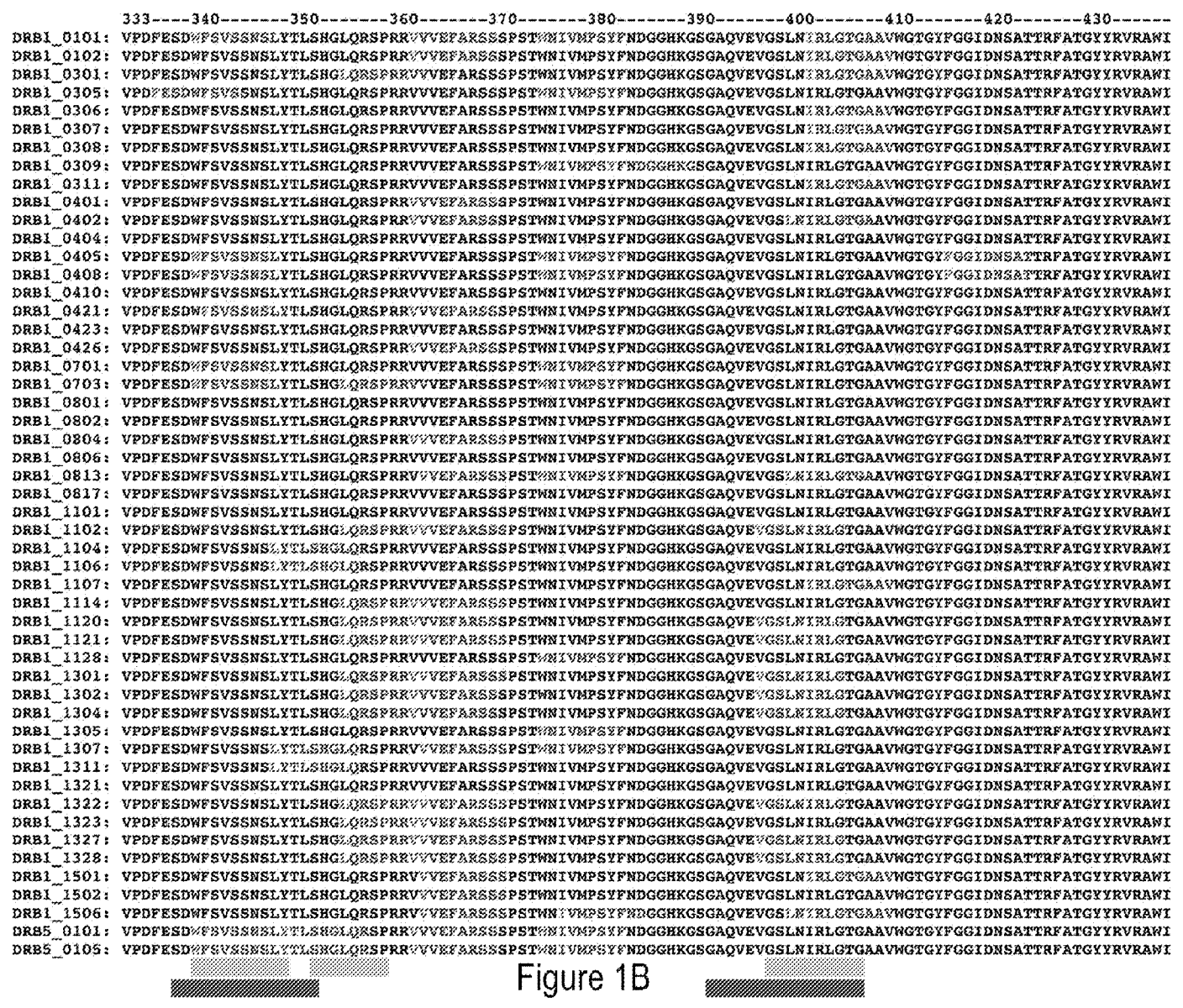

FIG. 1: ProPred predictions of antigenic peptides. A. SpCBM sequence (SEQ ID NO. 2). B. PaTD sequence (SEQ ID NO. 14). Predicted binders are coloured blue, with the first residue of each binding region shown in red. Antigenic peptides predicted by Nordic Biopharma (green bars) and ProImmune (purple bars) are shown under the sequences.

Figure 2:
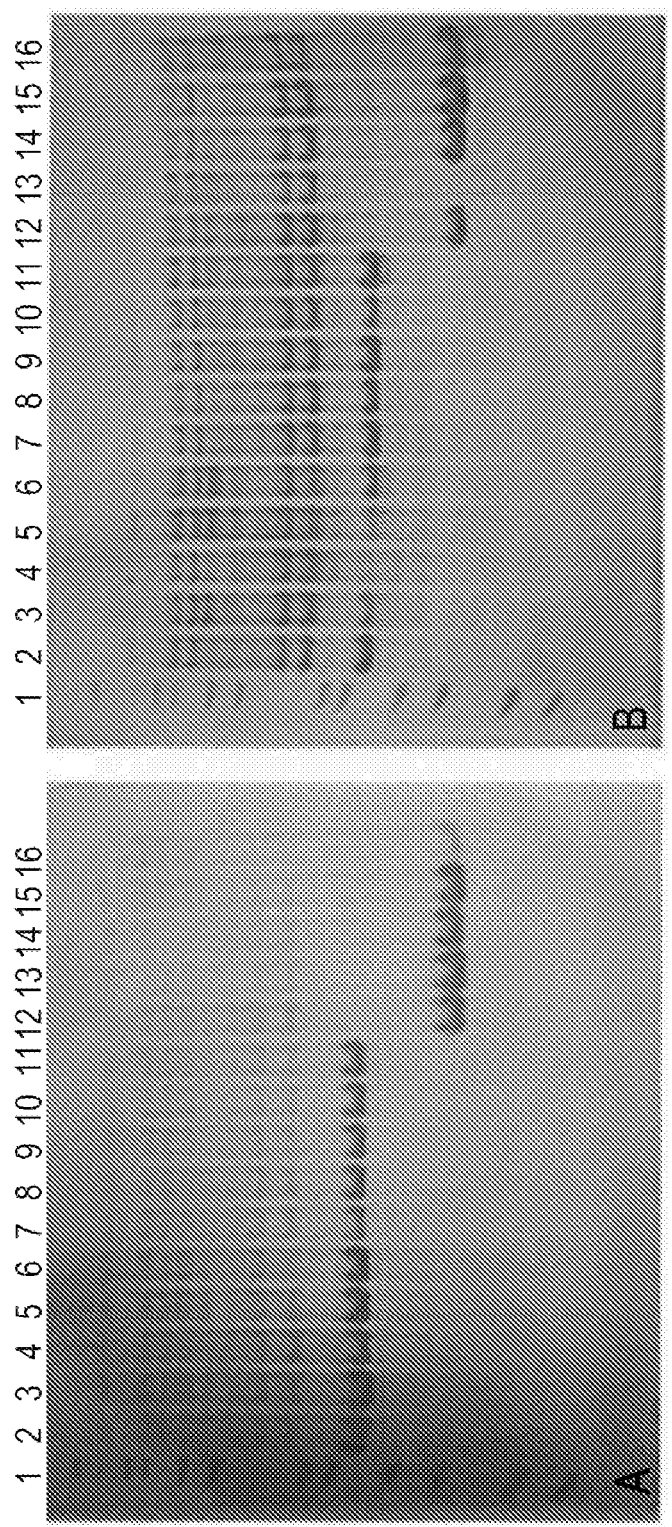

FIG. 2: Expression test of wild type and mutated domains. Lane 1, M12 standard; Lane 2, WT SpCBM; Lanes 3-11, Im15-Im23; Lanes 12-15, Im24-Im27; Lane 16, WT PaTD. A) Whole cell extracts, B) Soluble extracts.

Figure 3:
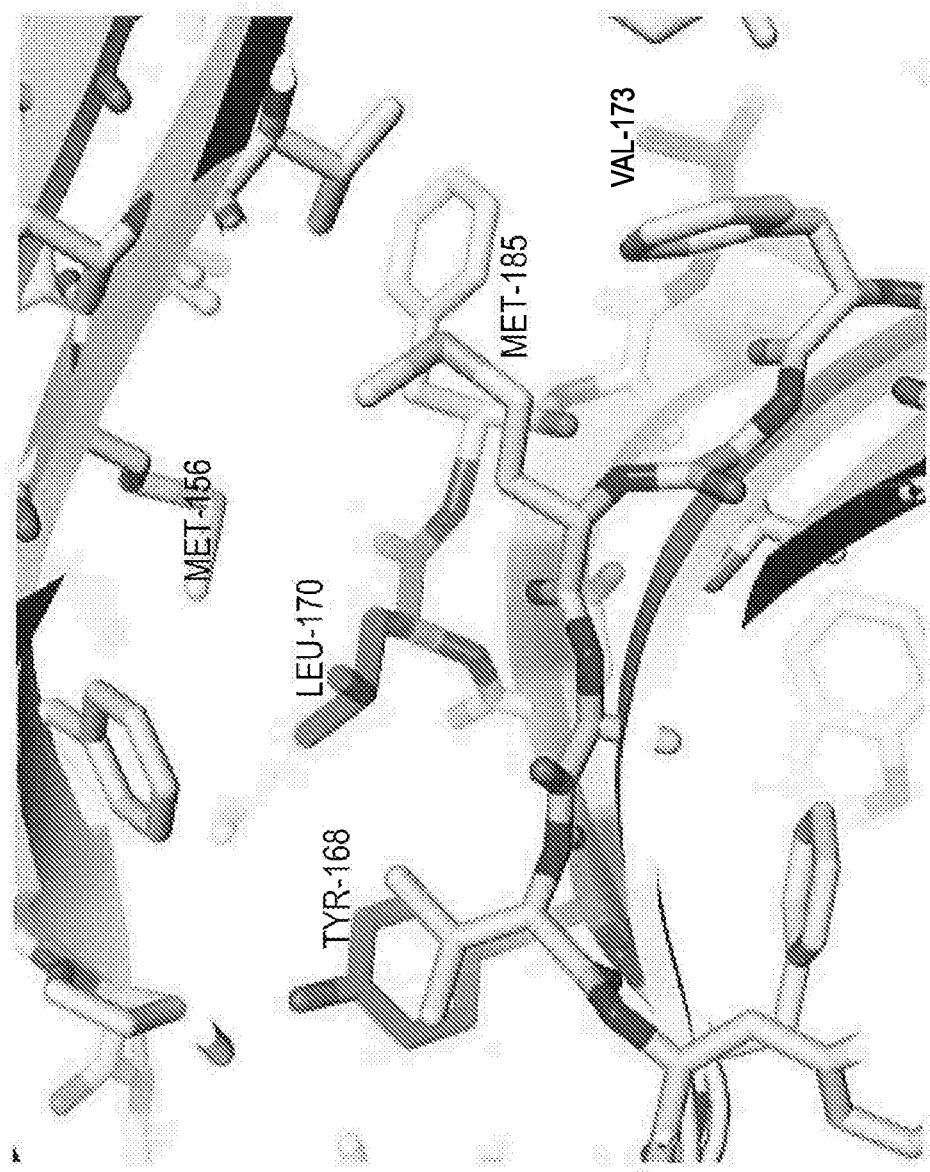

FIG. 3: Position of peptide 167-181 in the SpCBM structure

Figure 4:
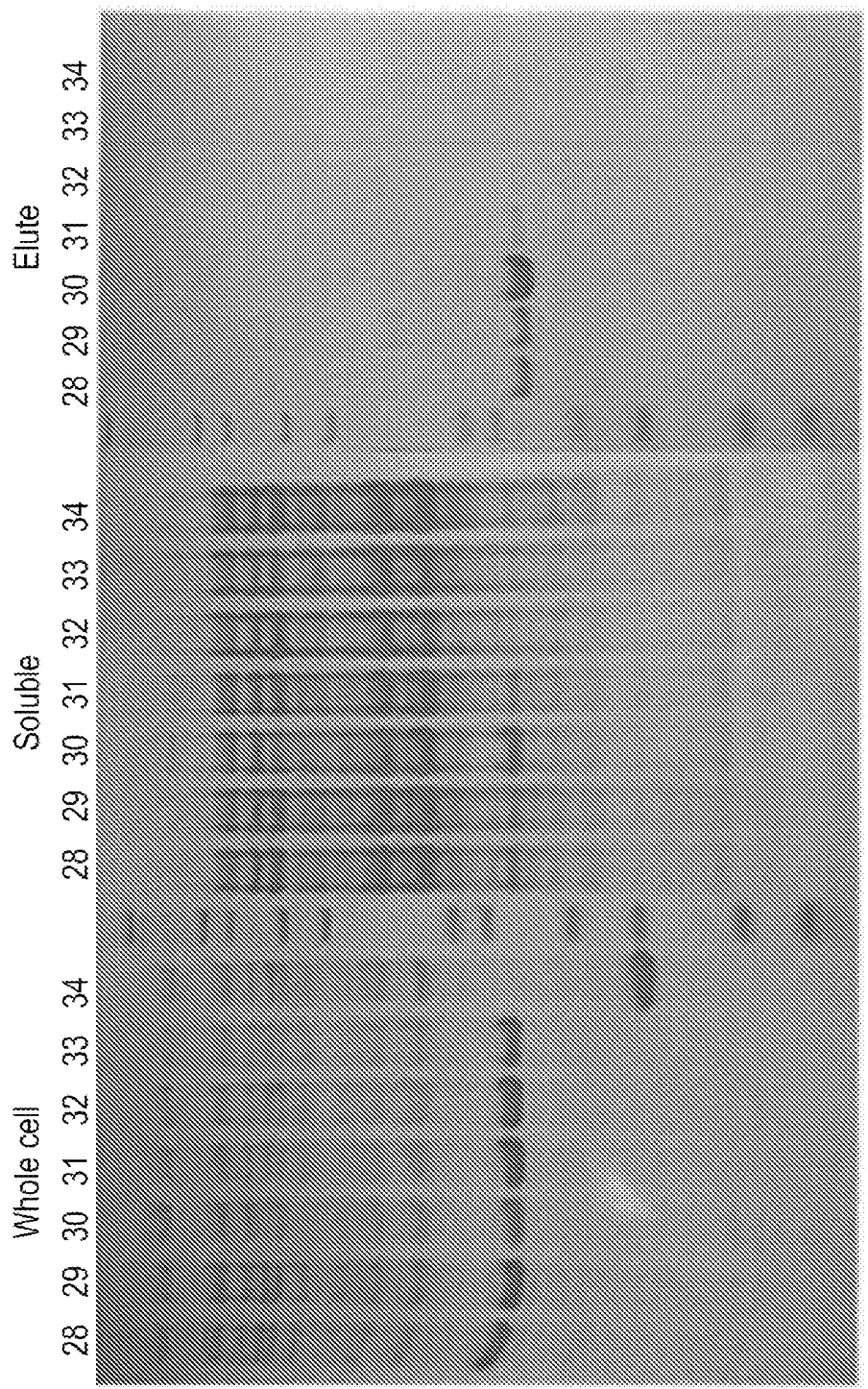

FIG. 4: Expression and Ni-NTA pull-down of variants Im28 to Im34

Figure 5:

FIG. 5: Sites of the HEX17 mutations on the hexamer structure. The quarternary structure of HEX17 was modelled by assembling the crystal structures of the individual SpCBM (pdb code 4c1x) and PaTD (pdb code 2w38) into the hexamer (i.e. 6 copies of SpCBM and 3 copies of PaTD per molecule). The positions of the bound ligand ($\alpha$2,3-sialyllactose) are shown in stick form (orange). The positions of the mutations are also shown: Blue, the sites of the A162P mutation; Cyan, the sites of the other two CBM mutations; Magenta, the sites of the TD mutations.

Figure 6:
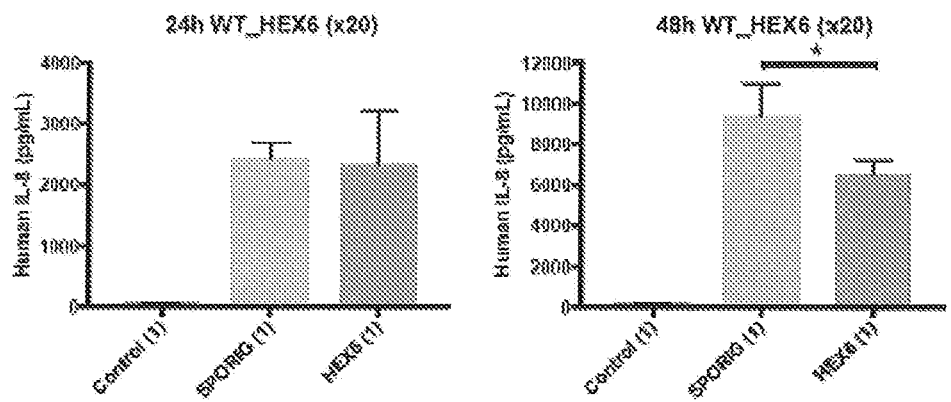
Figure 6:
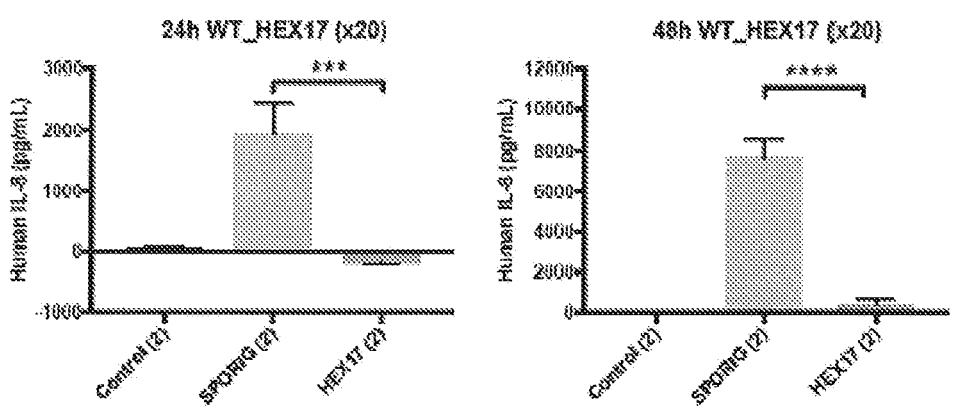
Figure 7A:
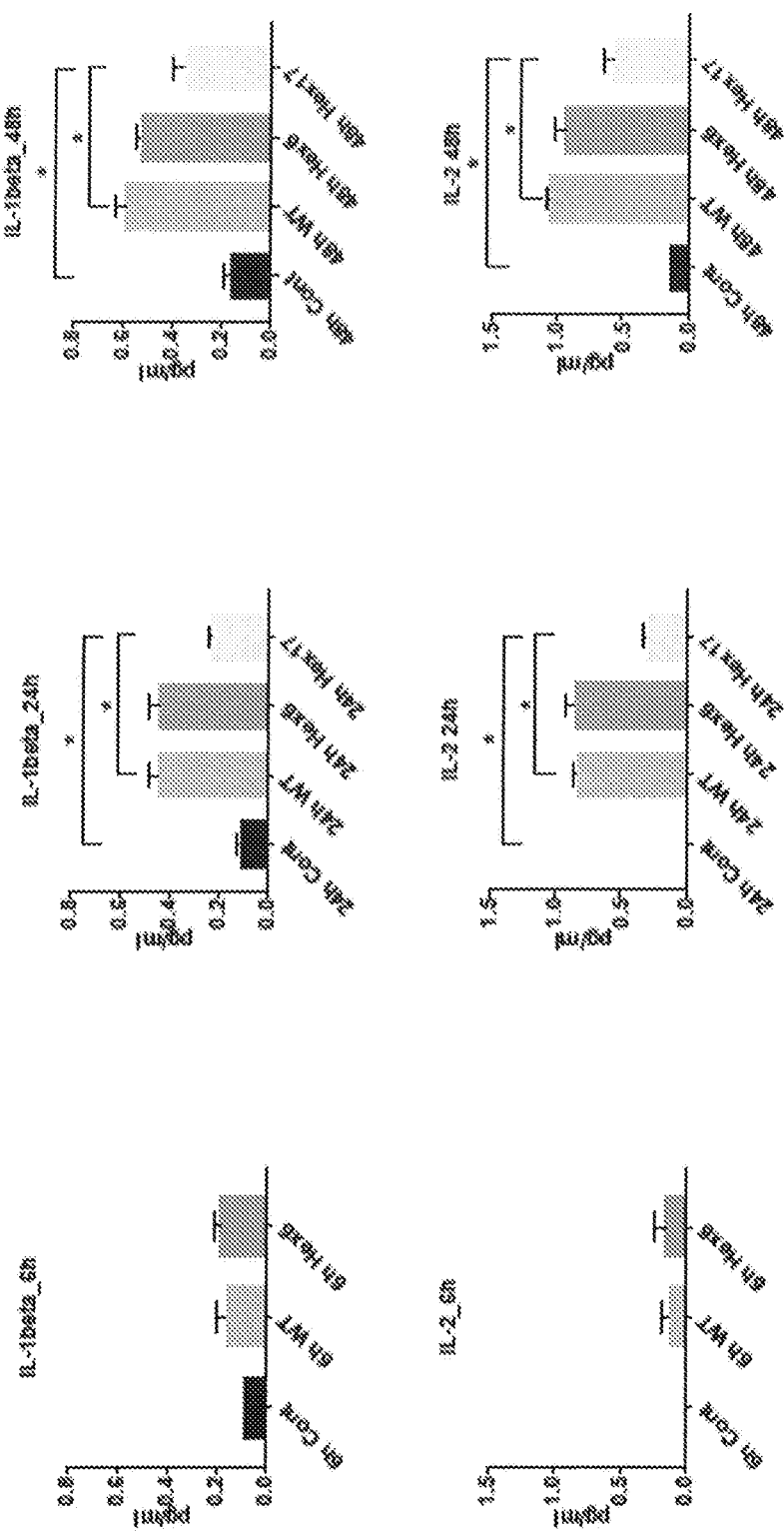
Figure 7B:
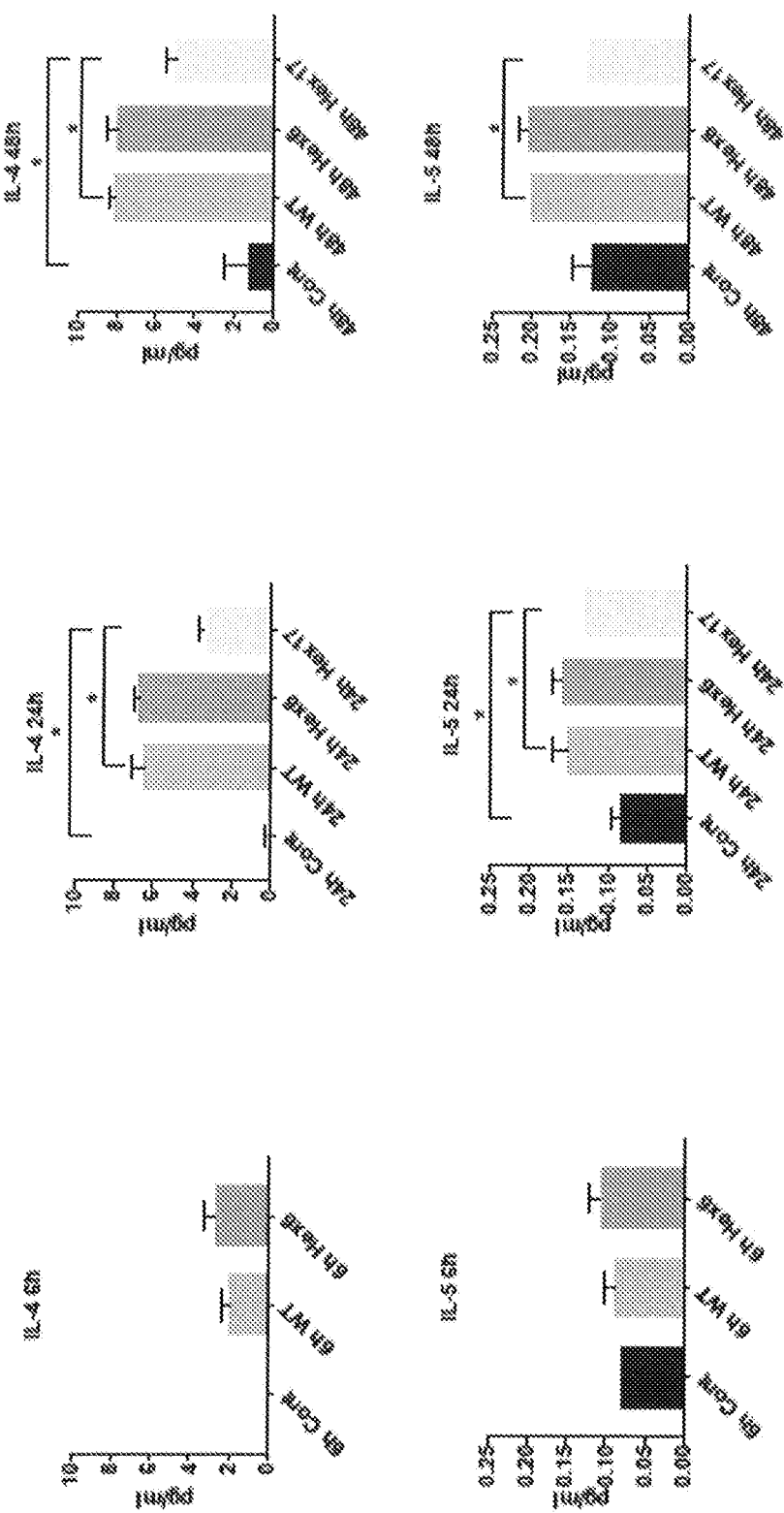
Figure 7C:
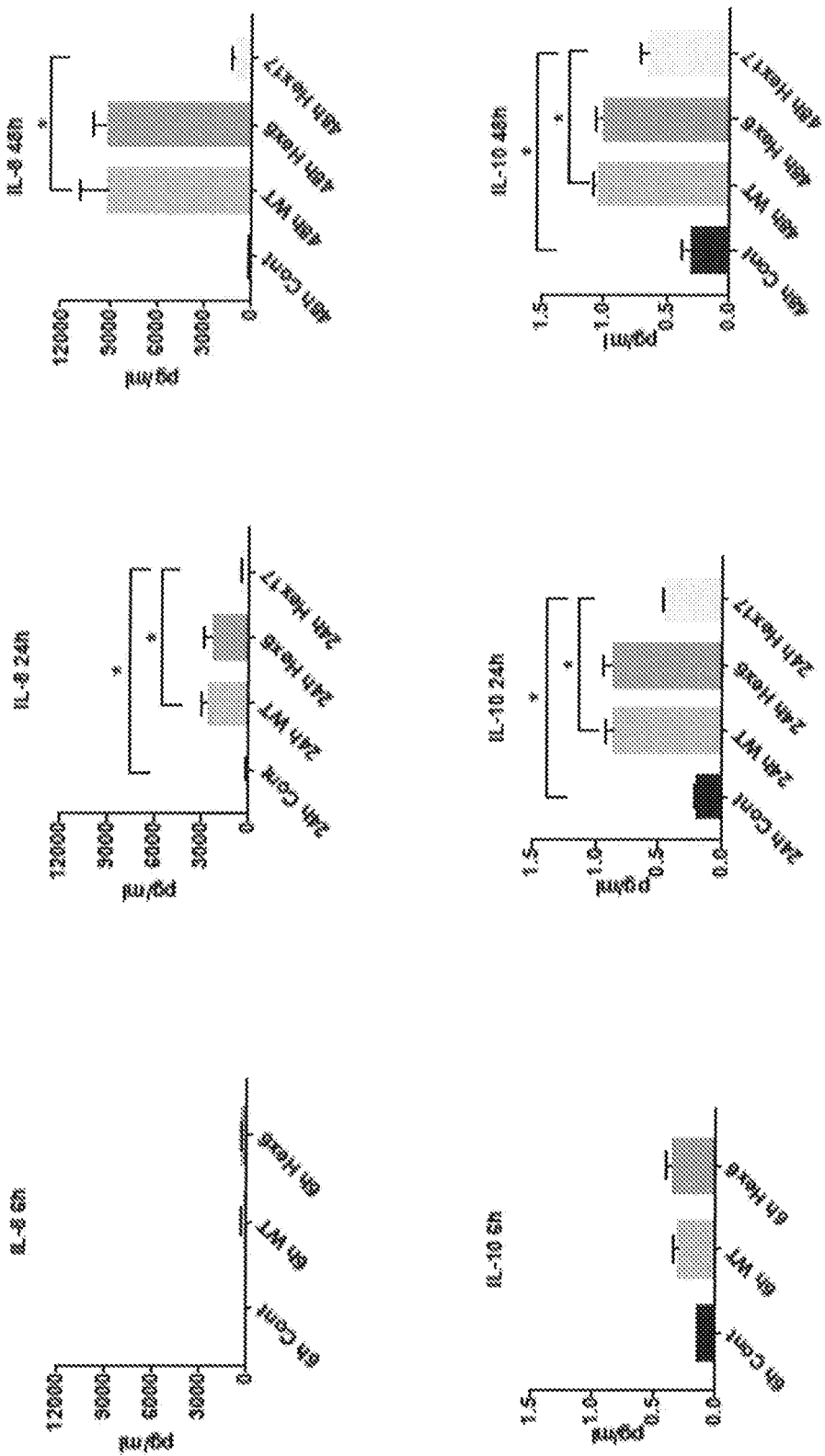
Figure 7D:
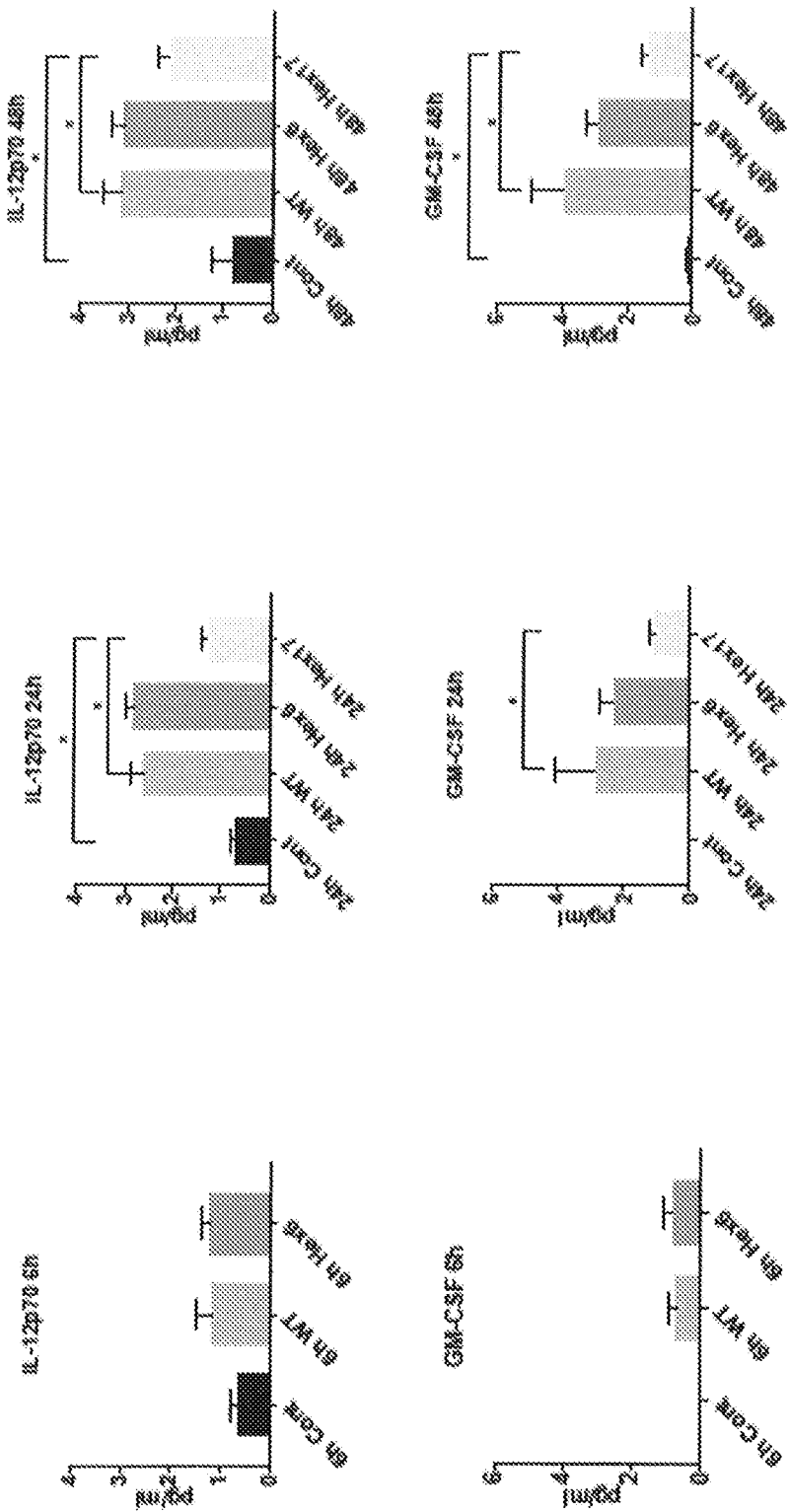
Figure 7E:
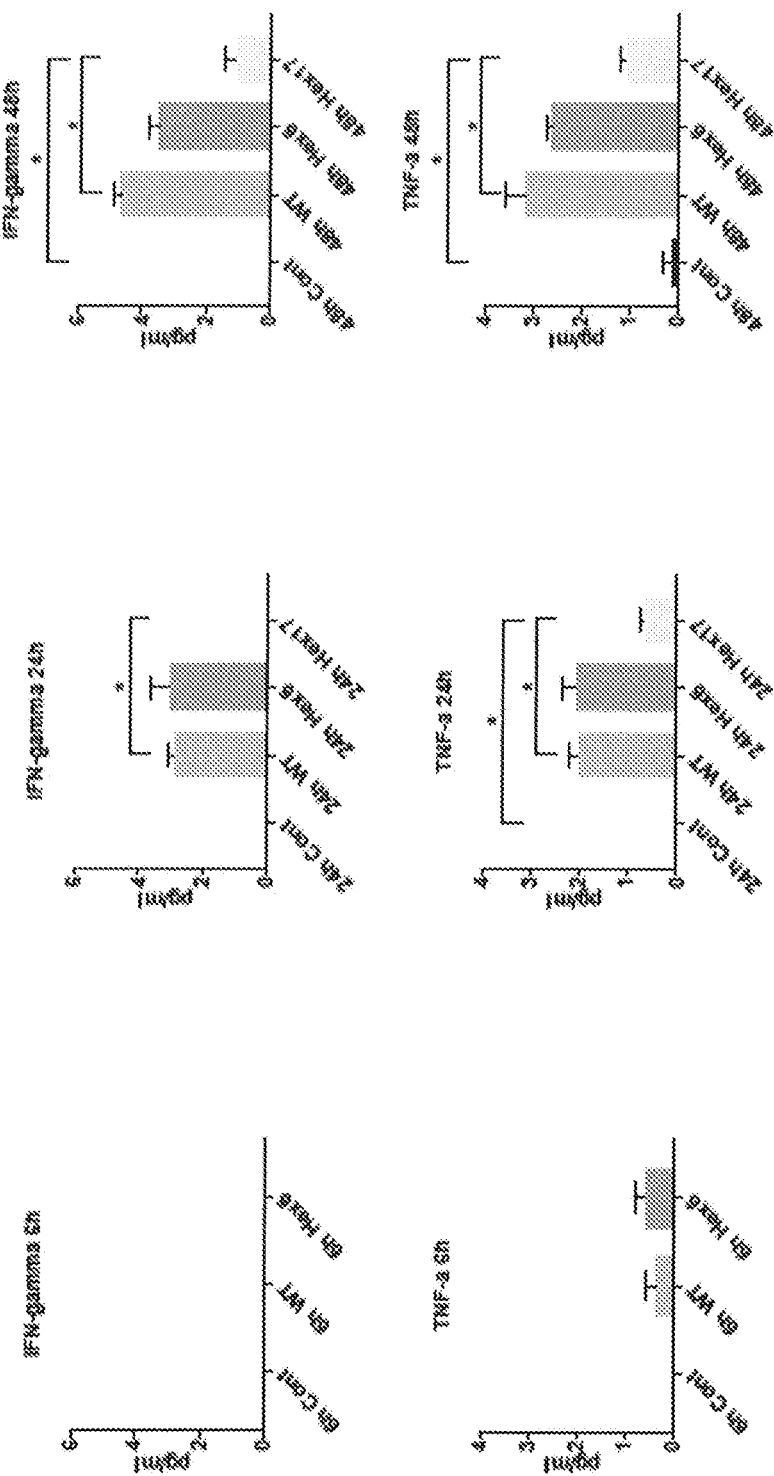
Figure 7F:
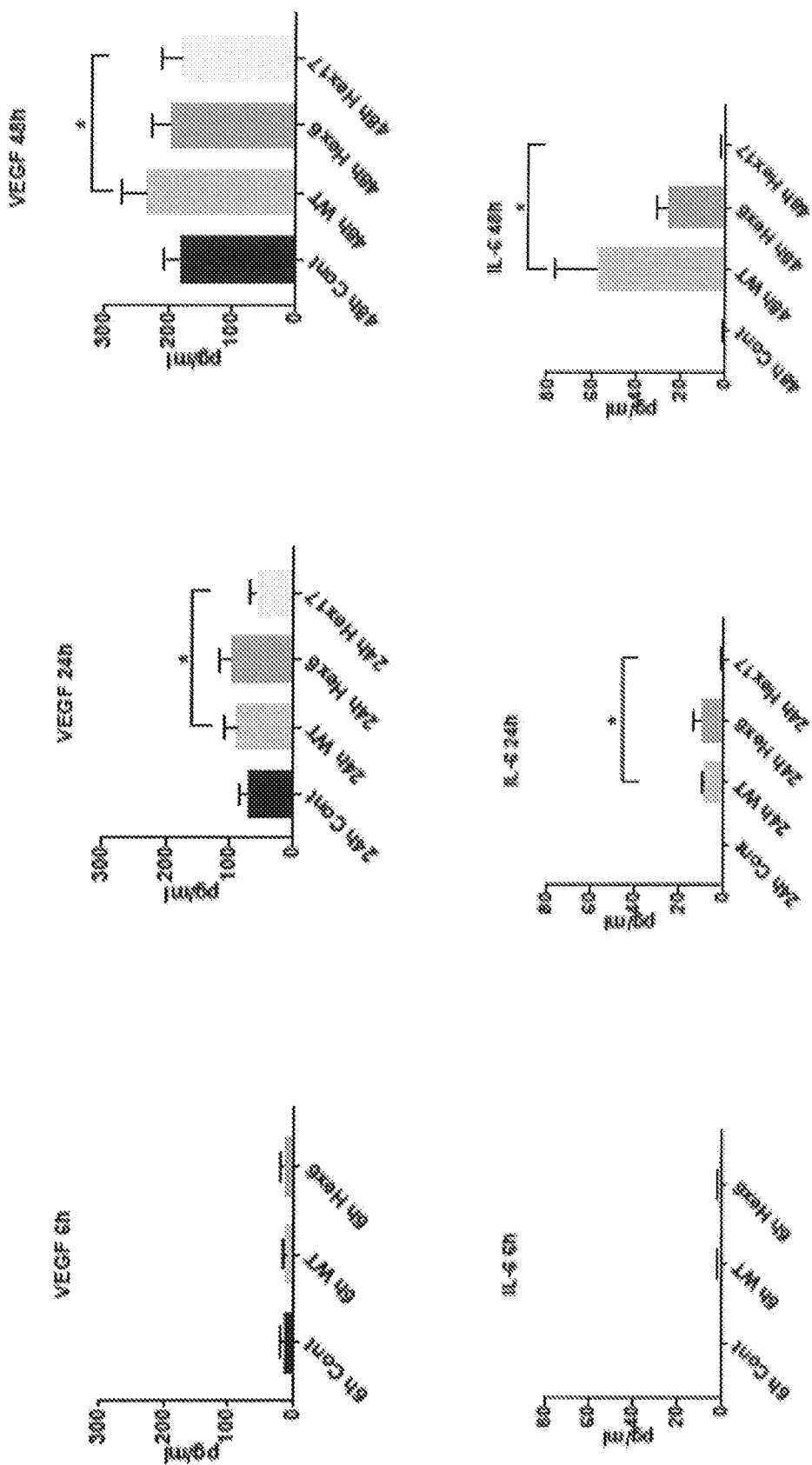

FIG. 6: IL-8 stimulation. A549 cells were stimulated by the addition of 10 µg of biologic (Sp2CBMTD (aka SpOrig), HEX6 or HEX17). Cell supernatant was harvested at 24 h or 48 h timepoints and the IL-8 content was determined by ELISA. Statistical significance between control and treated cells was determined with one-way ANOVA using Tukey's multiple comparison test.

FIG. 7: Multiplex analysis of inflammatory mediators. A549 cells were stimulated by the addition of 10 µg of biologic (Sp2CBMTD (aka SpOrig), HEX6 or HEX17). Cell supernatant was harvested at 6 h, 24 h or 48 h time-points and inflammatory mediators analysed using a Human Cytokine 12-plex Assay. Statistical significance between control and/or WT hexamer and hexamer variants was determined using a one-way ANOVA (Tukey's multiple comparison test).

Figure 8:
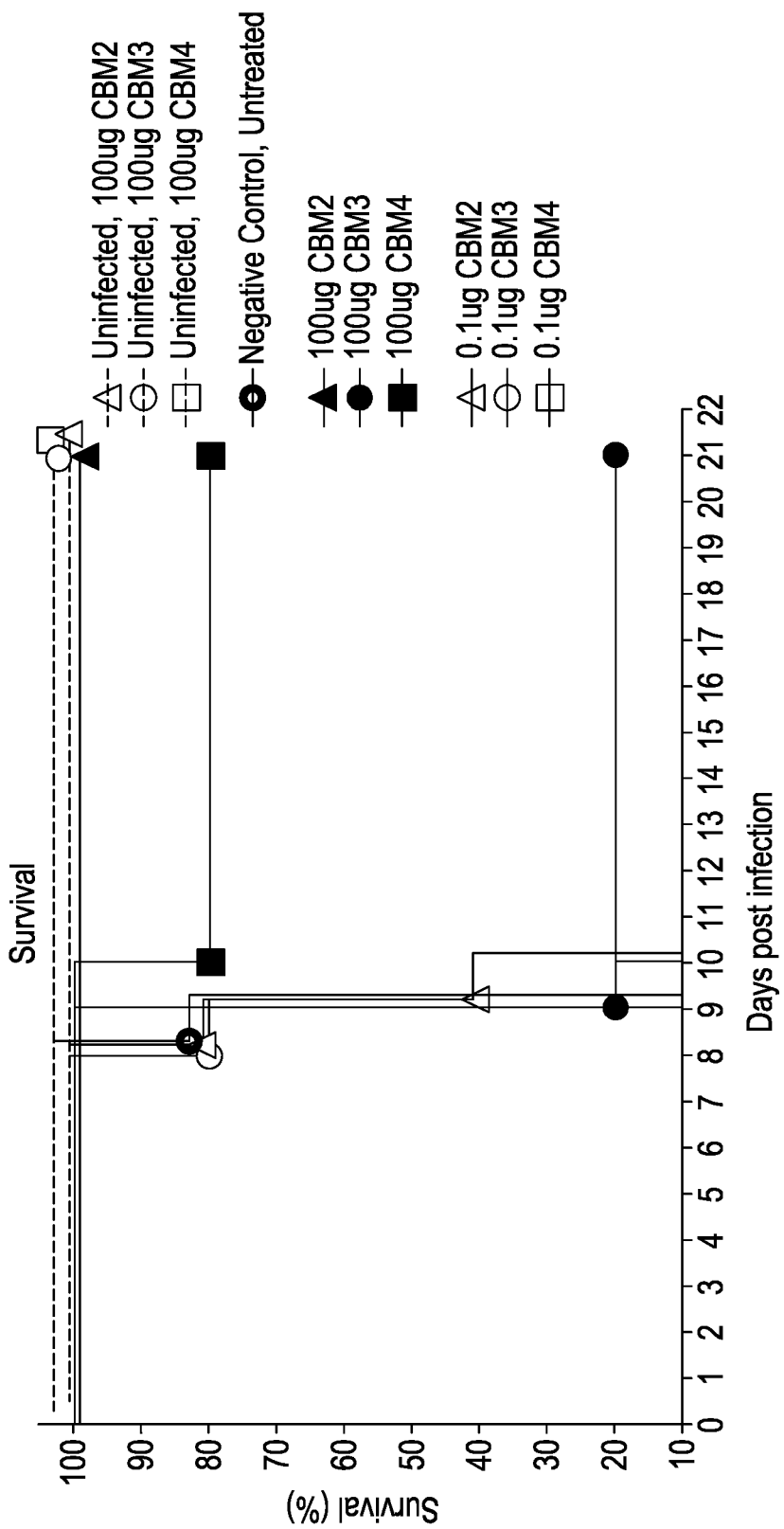

FIG. 8: Percentage survival of CBM-treated and untreated mice when lethally challenged with influenza strain PR8. CBM2, CBM3 and CBM4 represent HEX17, HEX6 and WT (SpOrig) respectively. Single CBM dosed animals were given 100 µg of CBM one day prior to lethal challenge with PR8; repeat dosed animal were given 2×0.1 µg of CBM at day-3 and day-1 prior to PR8 challenge.

Figure 9:
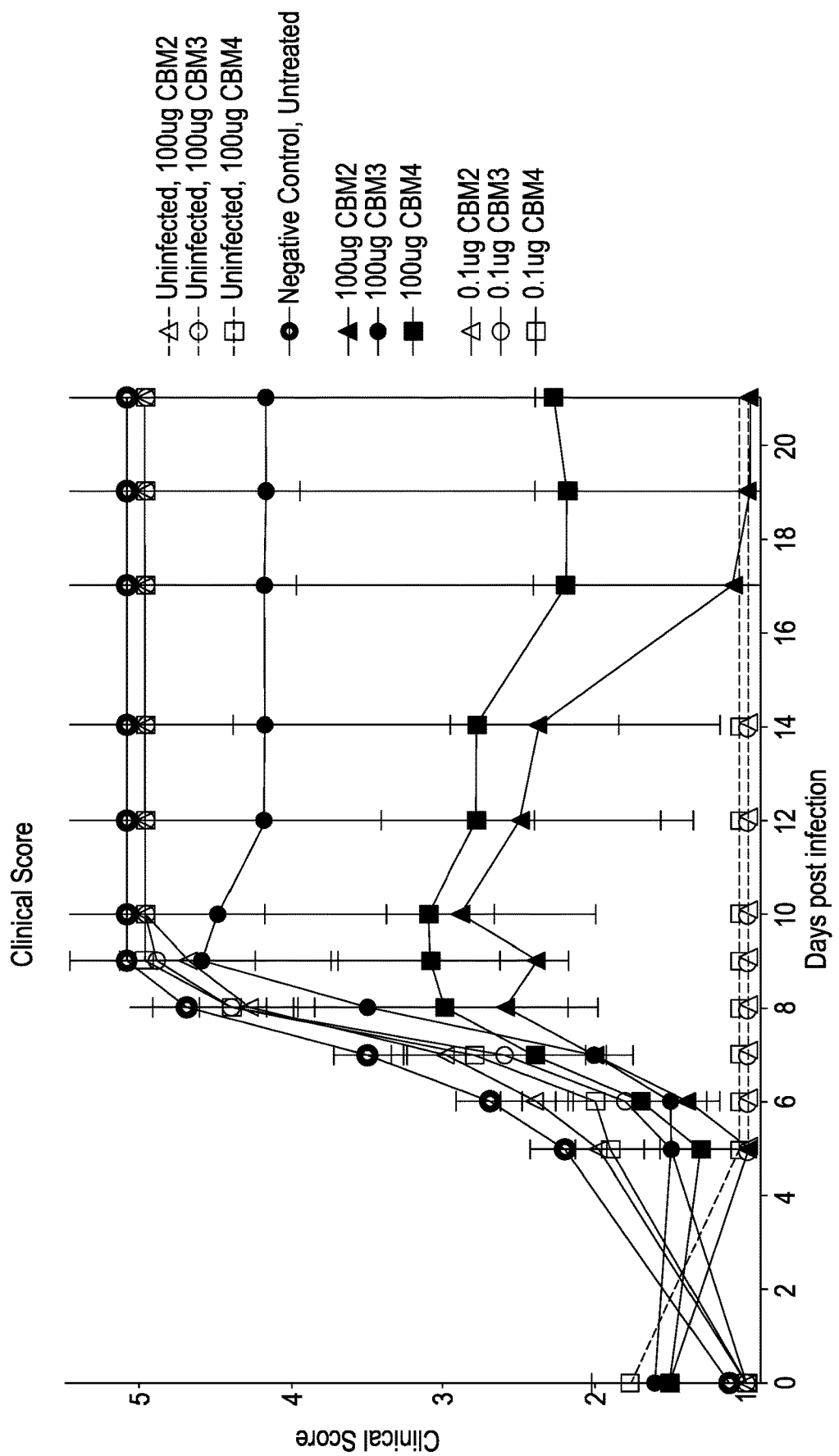

FIG. 9: Clinical scores of CBM-treated and untreated mice during PR8 infection. CBM2, CBM3 and CBM4 represent HEX17, HEX6 and WT (SpOrig) respectively. An ascending clinical score of 1 to 5 indicates no symptoms (1) to lethargy and death (5), respectively.

Figure 10:
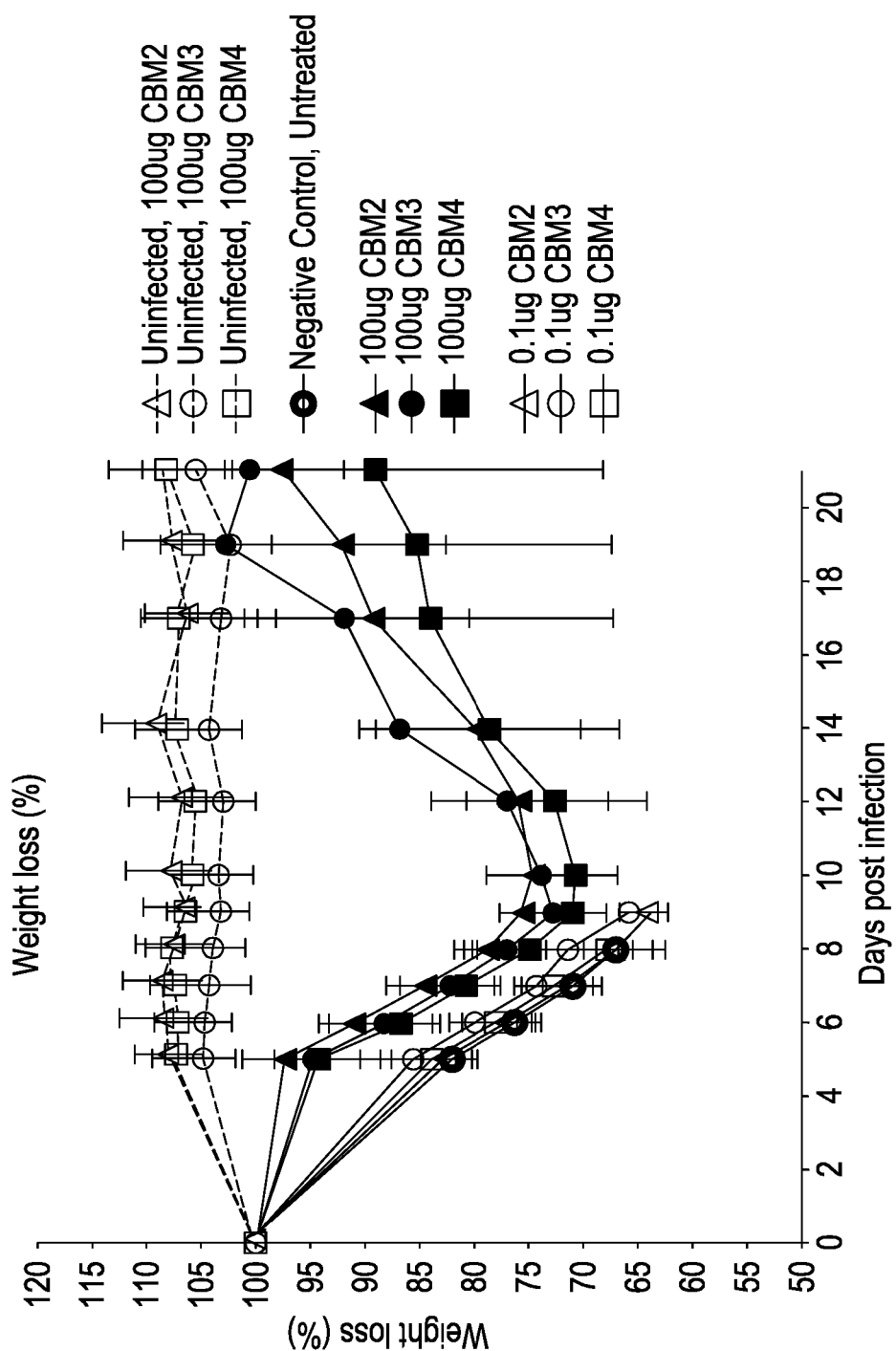

FIG. 10: Percentage weight loss of CBM-treated and untreated mice during PR8 infection. CBM2, CBM3 and CBM4 represent HEX17, HEX6 and WT (SpOrig) respectively.

Figure 11A:
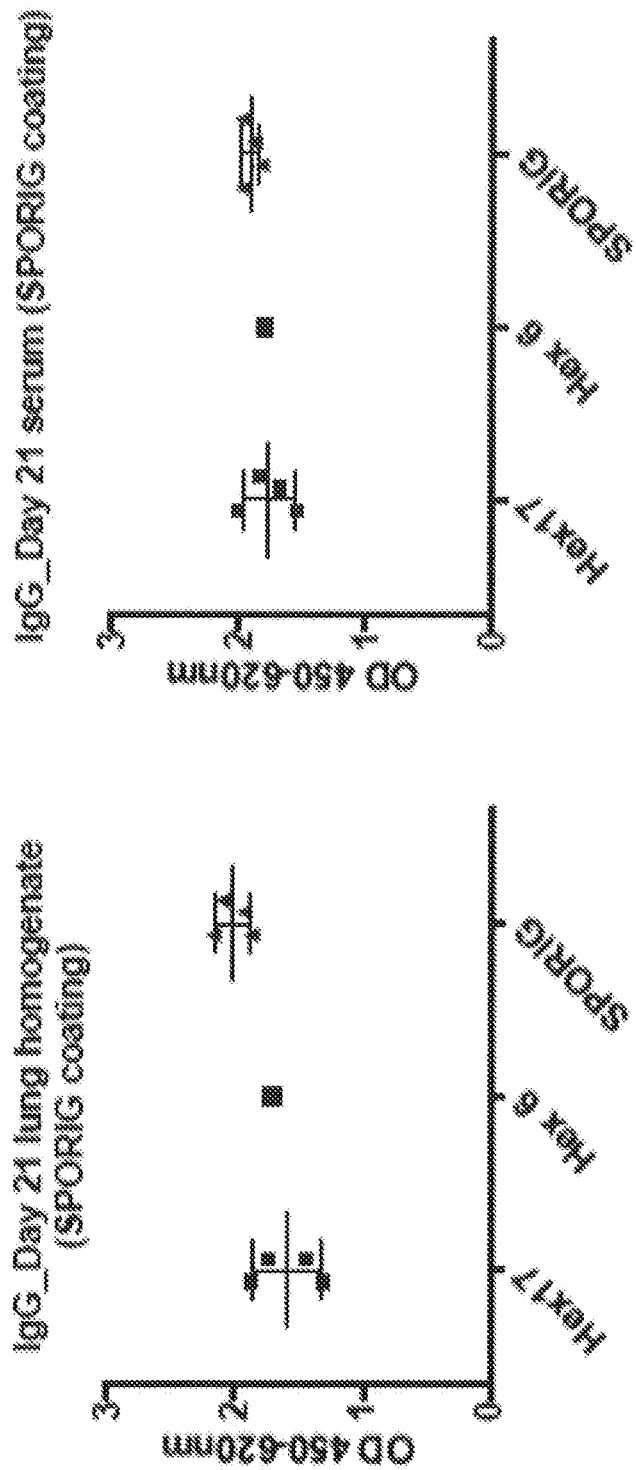
Figure 11B:
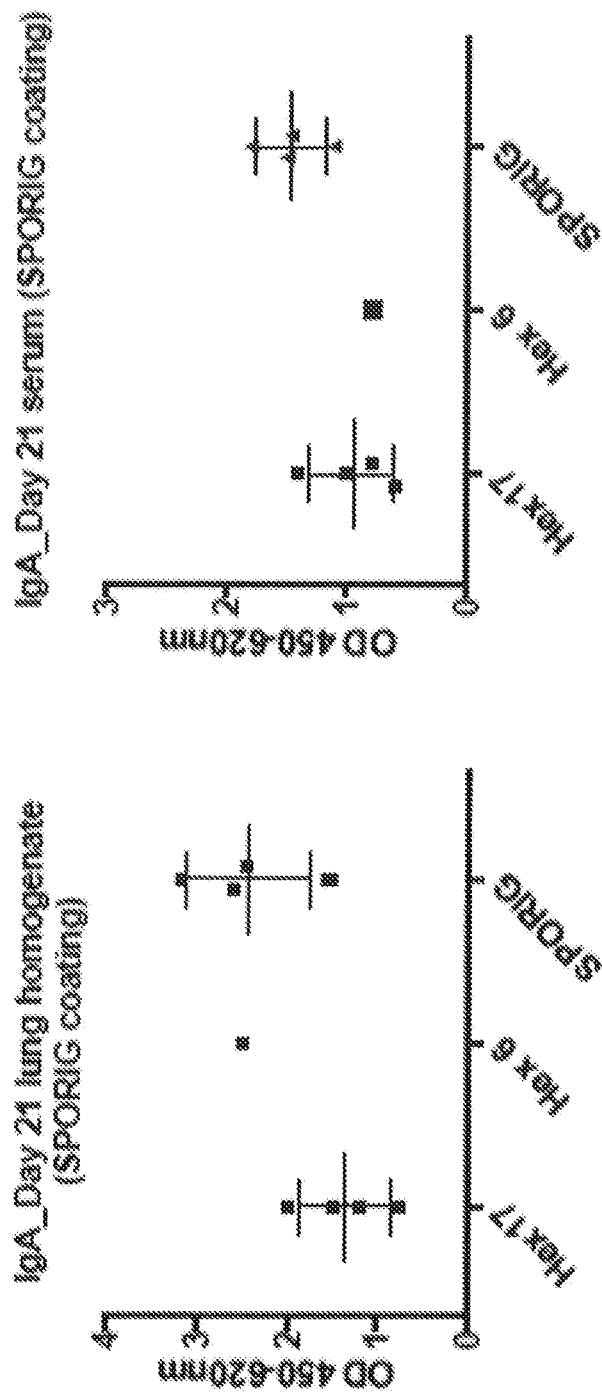
Figure 11C:
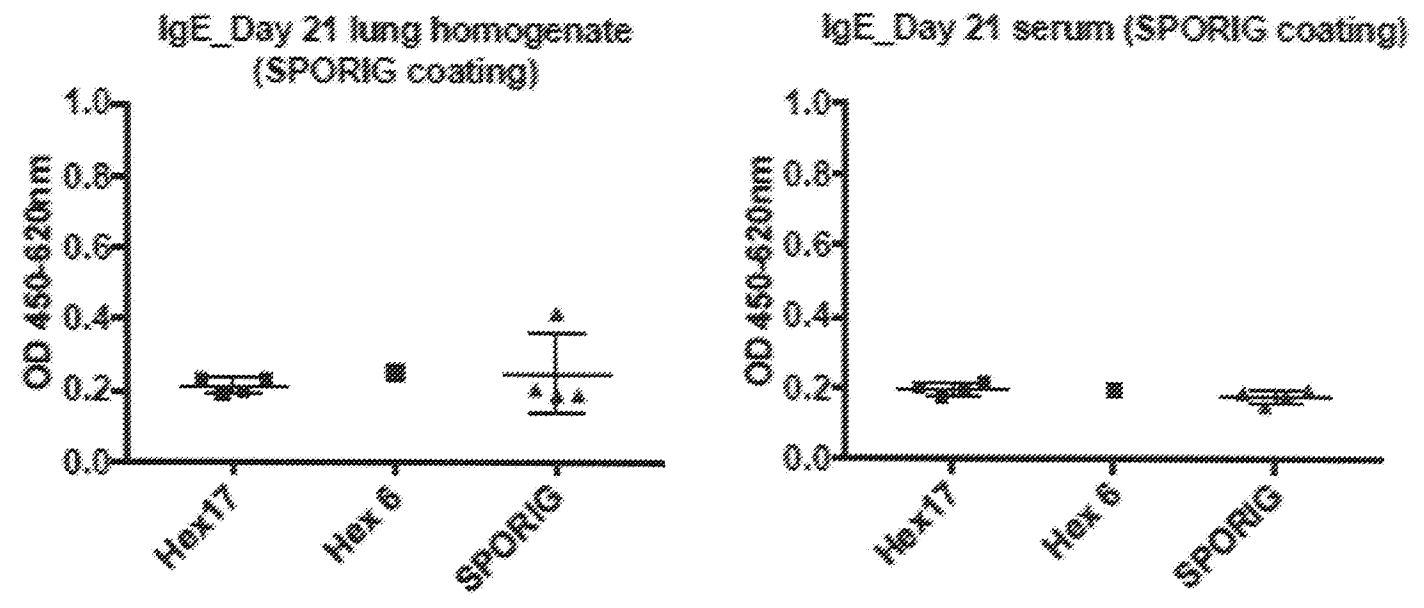
Figure 11D:
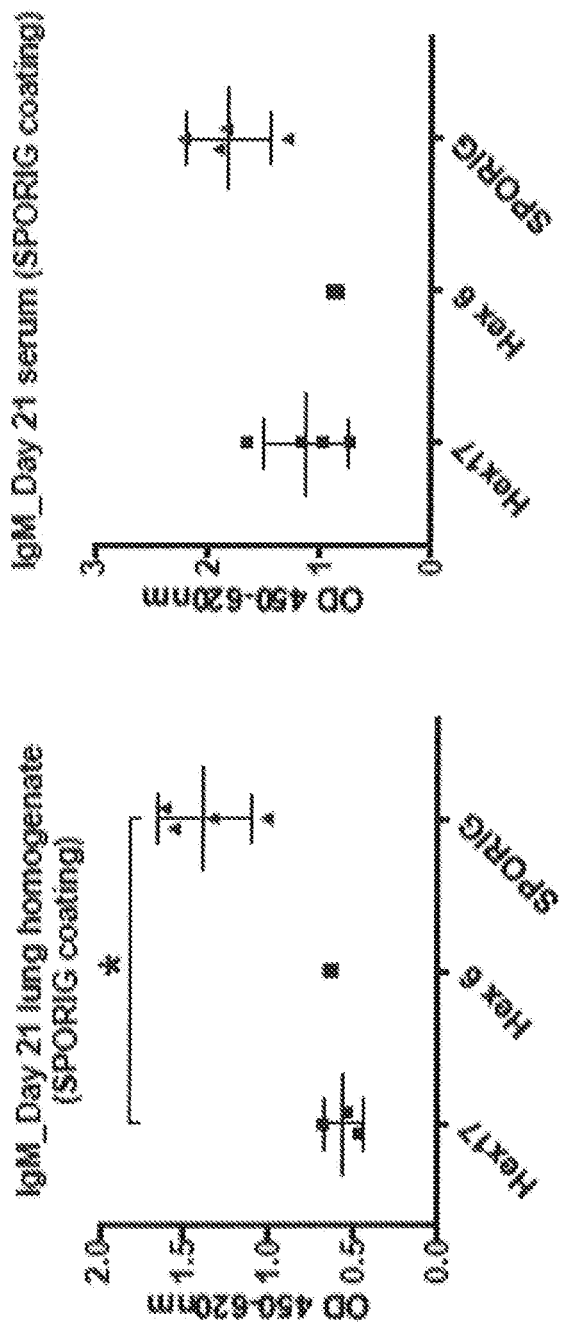

FIG. 11: Anti-mCBM antibody analysis of Day 21 lung homogenates and sera tissue from a PR8-challenged mouse study. Statistical significance between WT hexamer and hexamer variants was determined using a one-way ANOVA (Tukey's multiple comparison test).

Figure 12A:
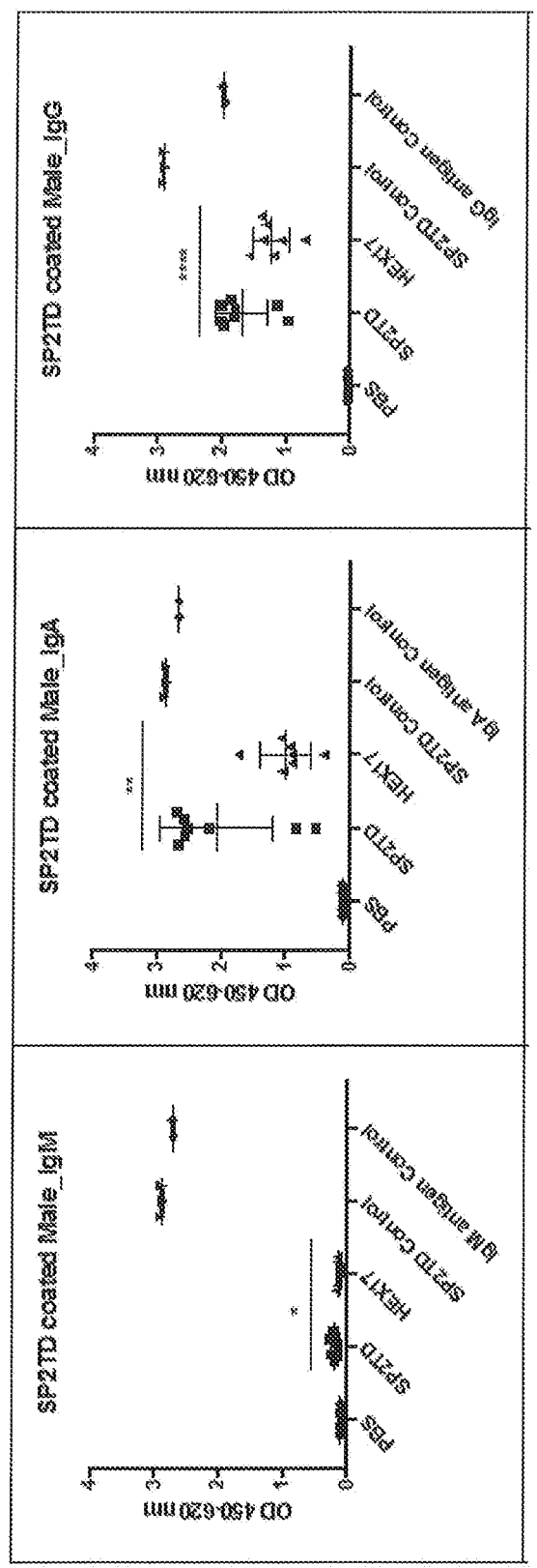
Figure 12A:
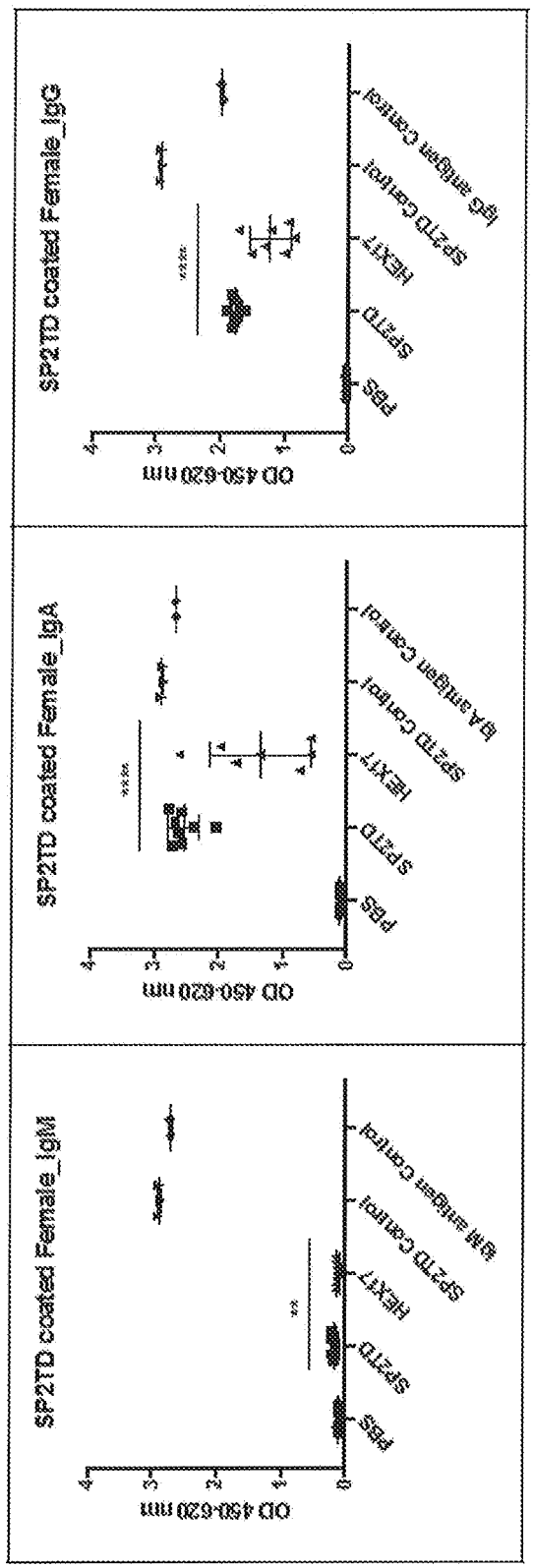
Figure 12A:
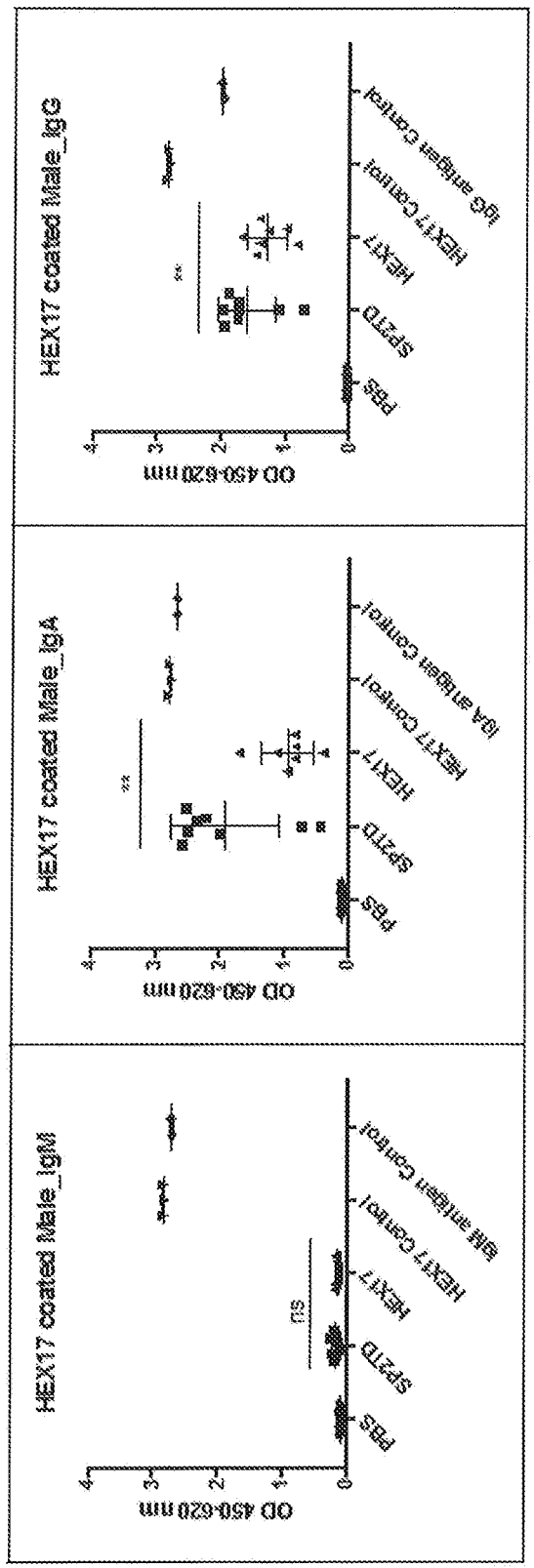
Figure 12A:
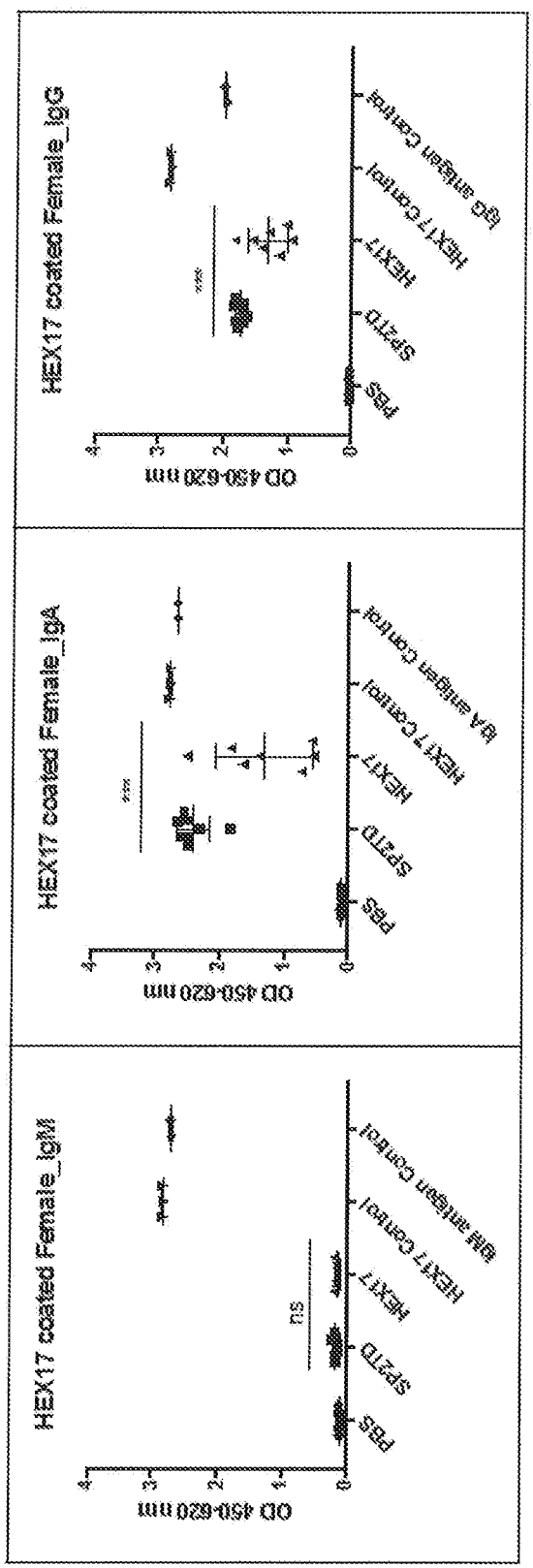

FIG. 12a: Anti-CBM antibody levels from Day 35 BAL mouse samples.

Figure 12B:
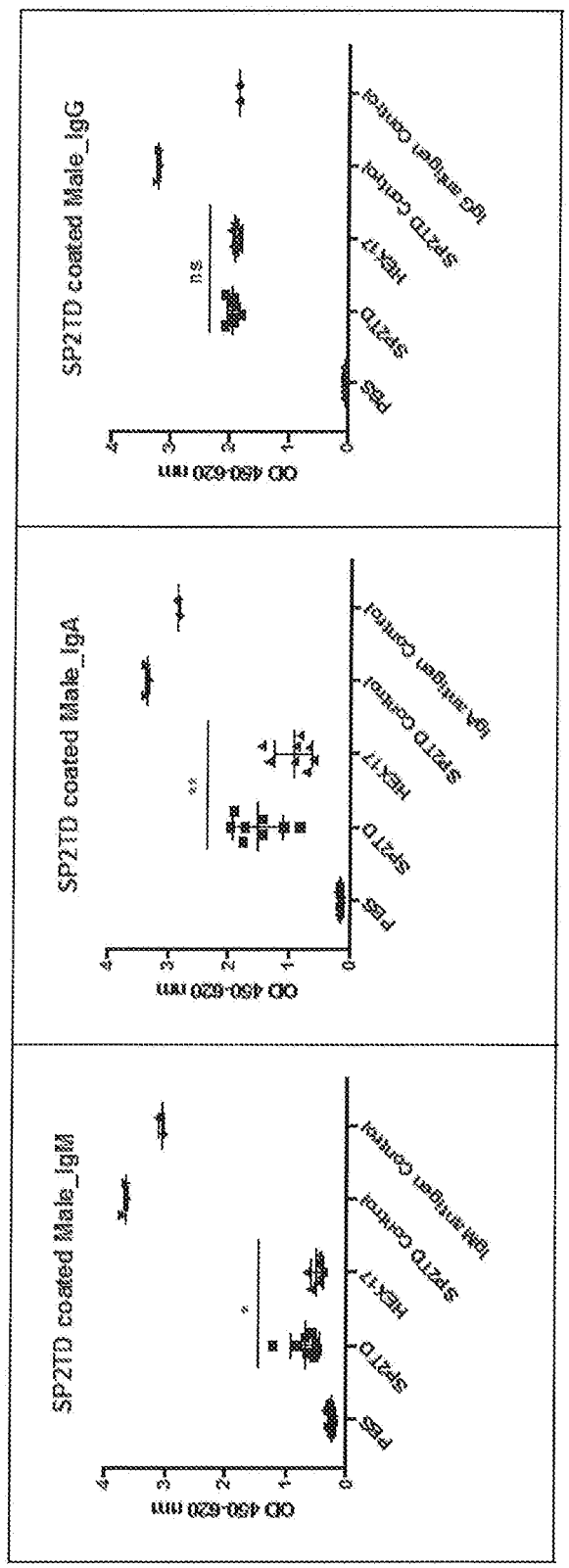
Figure 12B:
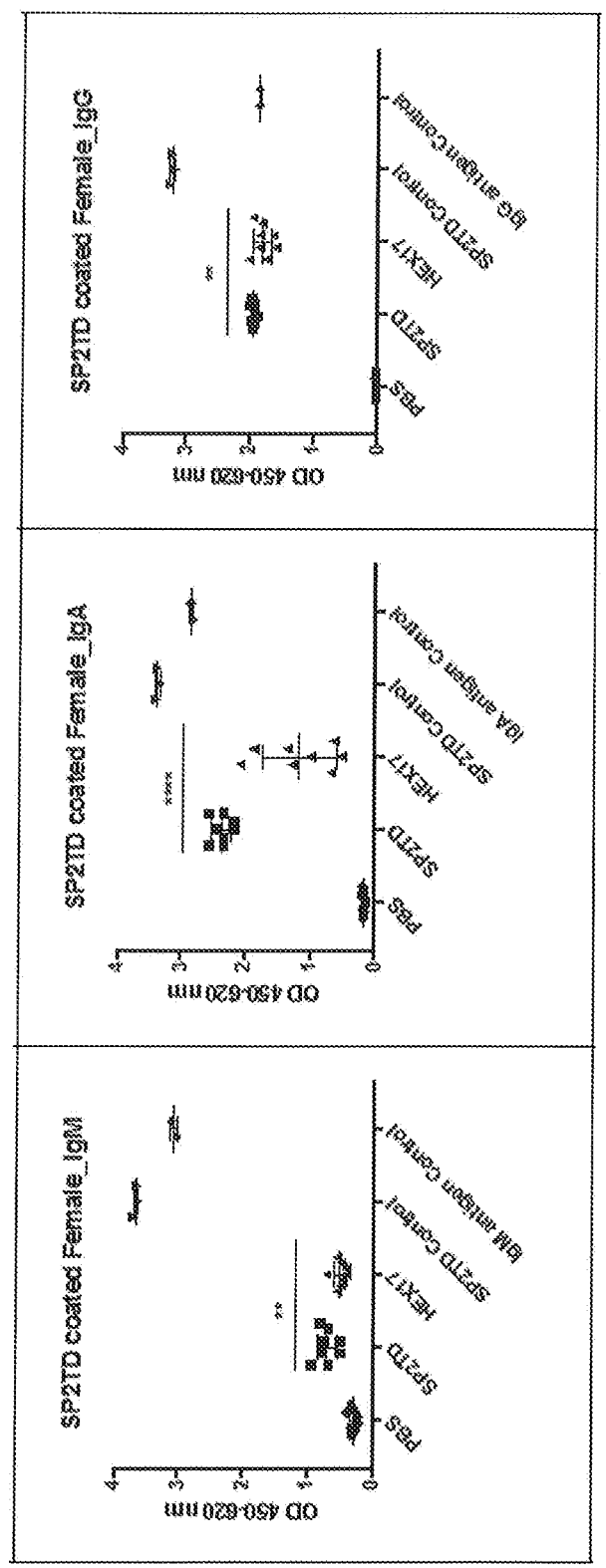
Figure 12B:
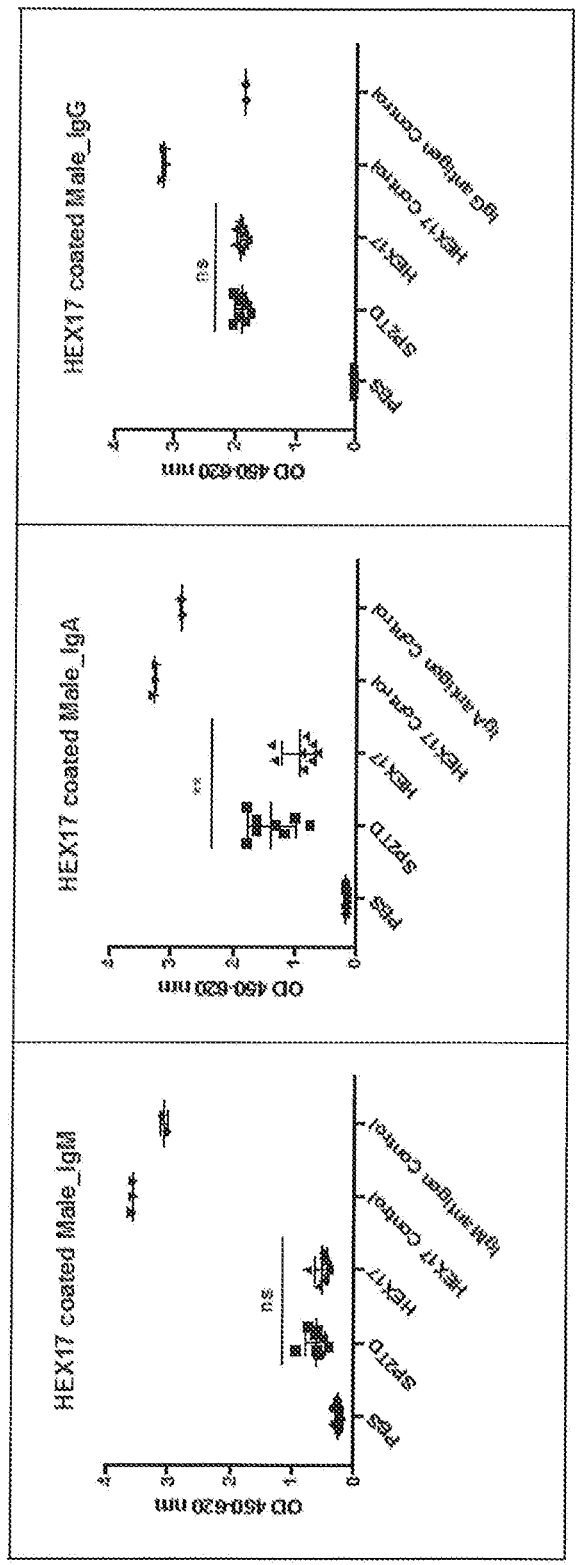
Figure 12B:
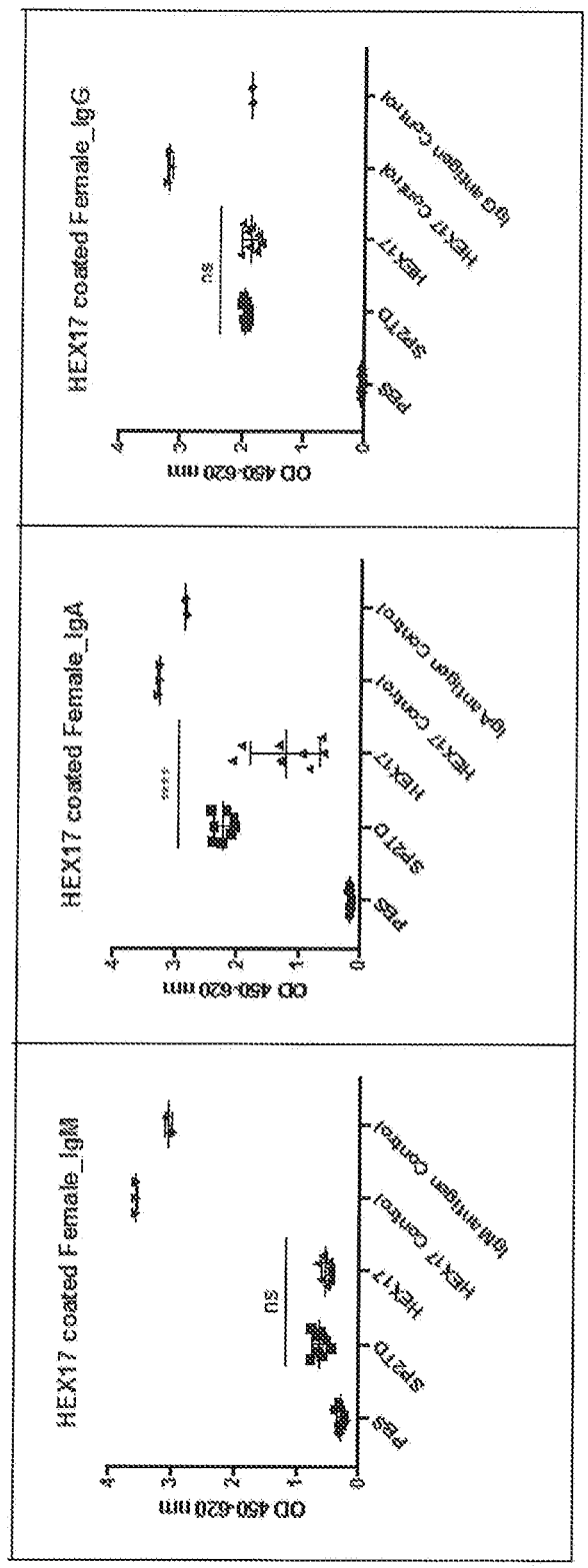

FIG. 12b: Anti-CBM antibody levels from Day 35 serum mouse samples

METHODS AND RESULTS

Sp2CBMTD: Prediction of Immunogenic Regions
Nordic Biopharma in Silico Screen
The in silico T-cell epitope screening identified four significant and two borderline immunogenic clusters:
Significant:

| Domain | Residue range | Sequence |
|---|---|---|
| SpCBM | 245 to 254 | GVLSRTSLRS |
| PaTD | 340 to 349 | WFSVSSNSLY |
| PaTD | 351 to 359 | LSHGLQRSP |
| PaTD | 398 to 406 | GSLNIRLGT |

Borderline:

| Domain | Residue range | Sequence |
|---|---|---|
| SpCBM | 167 to 178 | FYNLFSVSSATK |
| SpCBM | 239 to 251 | VRLYVNGVLSRTS |

ProImmune Human Donor T-Cell Proliferation Assay
The ProImmune study highlighted two regions of high antigenicity and two regions of moderate antigenicity:
High Antigenicity:

| Domain | Residue range | Sequence |
|---|---|---|
| SpCBM | 236 to 250 | KGRVRLYVNGVLSRT |
| PaTD | 392 to 406 | GAQVEVGSLNIRLGT |

Moderate Antigenicity:

| Domain | Residue range | Sequence |
|---|---|---|
| SpCBM | 167 to 181 | FYNLFSVSSATKKDE |
| PaTD | 338 to 352 | SDWFSVSSNSLYTLS |

ProPred in Silico Analysis
A further in silico tool, the online ProPred server[4], was also used. The output of the ProPred server is shown in FIG. 1. The relative positions of the Nordic Biopharma/ProImmune epitopes are also highlighted and indicate reasonable agreement between the three methods. In addition to the epitopes listed above, ProPred strongly predicted another immunogenic epitope in the SpCBM domain:

| Domain | Residue range | Sequence |
|---|---|---|
| SpCBM | 286 to 294 | IRNLITYNR |

Mutations in the Individual CBM and TD Domains
To guide the design of mutations that might reduce immunogenicity, ProPred was used to test the effect of changing each residue in these peptides to every alternative residue. Those that gave the greatest reduction in predicted number of allele binders were noted. As the crystal structure of both the SpCBM and TD domains are known, these mutations were also modelled to reduce the likelihood of introducing mutations that would obviously disrupt the protein structure.

Initially, nine single mutations in SpCBM and four single mutations in PaTD were introduced and are listed below ('Im' is short for immunogenicity mutant):

| (SpCBM) variants | Mutation | (PaTD) variants | Mutation |
|---|---|---|---|
| WT Sp | — | WTTD | — |
| Im15 | Y168W | Im24 | S342D |
| Im16 | L170A | Im25 | S345D |
| Im17 | L170T | Im26 | L348D |
| Im18 | V173G | Im27 | R403K |
| Im19 | V239A | | |
| Im20 | V239T | | |
| Im21 | V246G | | |
| Im22 | I286A | | |
| Im23 | Y292E | | |

Note: Im1 to Im14 (not shown) were introduced by mutagenesis into a non-codon optimized background, before the ProImmune data were available.

Synthesis of WT and Mutated Constructs
The genes encoding WT SpCBM, WT PaTD and the variants Im15 to Im27 were codon optimized for E. coli expression and synthesized by GeneArt. The genes were then cloned in-house into the pHISTEV vector for expression as 6His-tagged proteins.

Expression and Biophysical Characterization
An initial expression test was performed to assess solubility. The results show that all were expressed, but not all were soluble (FIG. 2). Note: solubility (or a lack thereof) is not necessarily a predictor of utility. One of skill will appreciate that when manufacturing or producing proteins, certain processes require the use of insoluble material as this is readily purified (from inclusion bodies and the like). Downstream protocols may then re-engineer proteins to modulate features such as solubility.

Results of the expression test show that:
Im16 (L170A) is insoluble or very poorly soluble
Im25 (TD, S345D) is insoluble
Im15 (Y168W) and Im17 (L170T) have reduced solubility
Im18 (V173G) and Im22 (I286A) are slightly reduced.
The remainder show soluble expression.

The 13 soluble proteins were expressed in E. coli and purified by immobilized metal affinity chromatography (IMAC), followed by TEV digestion to remove the 6His-tag, then reverse IMAC and size exclusion chromatography (SEC).

Ten purified domains (WT Sp, Im19, Im20, Im21, Im22, Im23, WTTD, Im24, Im26 and Im27) were further characterized by:
(i) Thermofluor to measure melting temperature (Tm)
(ii) Near UV circular dichroism (CD) to compare tertiary structures to WT
(iii) Dynamic light scattering (DLS) to check oligomeric state in solution
(iv) Surface plasmon resonance (SPR) to measure binding affinity to sialyllactose
(v) Measurement of IL-8 cytokine stimulation
The results are summarized in Table 1.

There is some indication that Im22 has lower Tm than WT. This residue is adjacent to M156 so may behave differently if M156F was included.

TD peptide 338-352:

Im24 (S342D) and Im26 (L348D) show similar characteristics to the WT trimerization domain, but with some suggestion of reduced Tm in Im26. These are in the 'moderately' antigenic region 338-352 SDWFSVSSNSLYTLS. The WT sequence was predicted to bind 9 alleles, while Im24 predicts 2 alleles and a Im24/Im26 double mutant predicts 1 allele.

TABLE 1

Qualitative summary of the biophysical characterizations of the WT domains and their variants. Colour coding is from green to red (including green', orange and yellow), where green indicates that the variant closely resembles its WT counterpart for that particular characteristic and pale green (green') or yellow indicate increasing degrees of differences. Red or orange indicate significant differences.

| Name | Mutation | Solubility | Purification | Tm +/− 6SL | NearUV CD | DLS | Biacore | Cytokine stimulation |
|---|---|---|---|---|---|---|---|---|
| WTSp | — | Green | Green | Green | Green | Green | Green | Green |
| Im15 | Y168W | Yellow | Orange | Red | N/A | N/A | N/A | N/A |
| Im16 | L170A | Red | N/A | N/A | N/A | N/A | N/A | N/A |
| Im17 | L170T | Yellow | Orange | N/A | N/A | N/A | N/A | N/A |
| Im18 | V173G | Green' | Orange | N/A | N/A | N/A | N/A | N/A |
| Im19 | V239A | Green | Green | Green | Green | Green | Green | N/D |
| Im20 | V239T | Green | Green | Green' | Green' | Green | Green | N/D |
| Im21 | V246G | Green | Green | Green' | Green | Green | Green | Green |
| Im22 | I286A | Green' | Green | Green' | Green | Green | Green | Green |
| Im23 | Y292E | Green | Green | Green' | Green' | Green | Yellow | Yellow |
| Im24 | S342D | Green | Green | Green | Green | Green | | |
| Im25 | S345D | Red | N/A | N/A | N/A | N/A | | |
| Im26 | L348D | Green | Green | Green' | Green | Green | | |
| Im27 | R403K | Green | Green | Green | Green | Green | | |
| WTTD | — | Green | Green | Green | Green | Green | | |

N/A: these characterizations were not performed due to poor solubility/purity of the protein.
N/D: not determined.

Sp Peptide 167-181:

Im15, Im16, Im17, Im18 are all insoluble or poorly soluble (as stated, this does not necessarily impact on protein utility). These are in the 'moderately' antigenic region 167-181 (FYNLFSVSSATKKDE). This region is clearly very sensitive to change.

Earlier results show that M156F, which sits adjacent to L170 (and I286), increases Tm by ~4° C.

This could therefore be combined with L170T. M156F does not increase predicted immunogenicity.

M185I increases Tm by 5° C., and lies parallel to L170 (FIG. 3). This mutation could also be included. Note that, like M156F, M185I does not increase predicted immunogenicity but slightly reduces the number of predicted allele binders.

Sp Peptide 236-250:

Im19, Im20, Im21 all behave similarly to WT. These are in the 'highly' antigenic region 236-250 (KGRVRLY-VNGVLSRT).

Im19 (V239A) was chosen over the threonine mutation (Im20, V239T). There is no difference in predicted immunogenicity but Im19 is a closer match to WT Thermofluor Tm and Near UV spectrum. This would be combined with Im21 (V246G).

Sp Peptide 286-294:

Im22 (I286A) is broadly similar to WT while Im23 (Y292E) appears to exhibit reduced ligand affinity. This region, 286-294 IRNLTVYNR, was not flagged up by ProImmune but is strongly predicted by ProPred to be immunogenic.

TD Peptide 392-406:

Im27 (R403K) is similar to WT. It is part of the 'highly' antigenic region 392-406 GAQVEVGSLNIRLGT. Predicted alleles are reduced from 21 to 3 when this mutation is introduced.

Synthesis of Multiple Mutation Combinations Im28-34

The following mutations were introduced:

i) M156F/L170T ii) M156F/L170T/M185I: In ProPred, alleles predicted for this region are reduced from 31 in the WT to 19 for this combination.

iii) V239A/V246G: In ProPred, alleles for this region are reduced from 44 to 3.

iv) I286A/Y292E: In ProPred, alleles are reduced from 41 to 1.

v) V239A/V246G/I286A/Y292E combines the previous two doubles.

vi) M156F/L170T/M185I/V239A/V246G/I286A/Y292E combines all the Sp mutations vii) TD: S342D/L348D/R403K: Predicted alleles are reduced from 9 to 1 for TD peptide 338-352 and alleles for peptide TD peptide 392-406 are reduced from 21 to 3. This triple mutant combines all the TD mutants. They are all surface exposed and distal to the N-terminal end of TD, so would not be expected to interfere with SpCBM in the hexamer form.

The constructs are named Im28 to Im34:

| (SpCBM) variant | Mutations |
|---|---|
| Im28 | M156F/L170T |
| Im29 | M156F/L170T/M185I |
| Im30 | V239A/V246G |
| Im31 | I286A/Y292E |
| Im32 | V239A/V246G/I286A/Y292E |
| Im33 | M156F/L170T/M185I/V239A/V246G/I286A/Y292E |
| (PaTD) variant | Mutation |
| Im34 | S342D/L348D/R403K |

2.5 Expression and Biophysical Characterization of Im28-Im34

As with the single mutations, the combinations Im28 to Im34 were synthesized by GeneArt and subcloned into pHISTEV for expression analysis. A nickel bead pull-down on the His-tagged soluble extract was also performed (FIG. 4).

Hexameric Forms
Design of Hexameric Constructs HEX1 to HEX17
Genes encoding the hexameric forms (called Hex1 to Hex17) were synthesized by GeneArt:
Sp2CBMTD

| variant | Mutations |
|---|---|
| HEX1 | CBM1(L170T V239A V246G I286A Y292E)-CBM2(L170T V239A V246G I286A Y292E)-TD (S342D L348D R403K) |
| HEX2 | CBM1(V239A V246G I286A Y292E)-CBM2(V239A V246G I286A Y292E)- TD (S342D R403K) |
| HEX3 | CBM1(V239A V246G I286A)-CBM2(V239A V246G I286A)-TD (S342D R403K) |
| HEX4 | CBM1(V239A V246G)-CBM2(V239A V246G)-TD (S342D) |
| HEX5 | CBM1(V239A V246G)-CBM2(V239A V246G)-TD(R403K) |
| HEX6 | CBM1(V239A V246G)- CBM2(V239A V246G)-TD (S342D R403K) |
| HEX17 | CBM1(V239A V246G A162P)- CBM2(V239A V246G A162P)-TD (S342D R403K) |

The hexameric forms were synthesized in two parts to avoid problems associated with synthesising repeat sequences in the tandem CBM copies. The first gene covered the first CBM and the second part encompassed the second CBM plus the TD. These could then be simultaneously cloned into pHISTEV to create the Sp2CBMTD construct that trimerizes upon expression.

The first hexamer, HEX1, contained the mutations L170T/V239A/V246G/I286A/Y292E in the CBMs and S342D/L348D/R403K in the TD.

The solubility data of the individual domains indicated that HEX1 was unlikely to be soluble (again, not necessarily a reflection on the utility of the molecule); a further construct, HEX3, was synthesized. Note that HEX2 contained the same mutations as Hex3, but with the addition of Y292E.

HEX3 was synthesized and subcloned into the pHISTEV vector. Expression was insoluble under all conditions tested (varying temperature, IPTG concentration, cell density at induction, with or without heat shock). The CBM-only domain containing the same three mutations (V239A V246G I286A) is soluble. A double mutant (V239A V246G) behaves very similarly to WT. Therefore, further variants (HEX4, HEX5 and HEX6) were designed and constructed by PCR/ligations, which exclude I286A and contain either one or both of the TD mutations.

During the work on HEX6 a number of other versions were designed containing different combinations of the HEX6 mutations (numbered HEX7 to HEX16; not characterised).

HEX17 contains the HEX6 mutations with an additional A162P mutation. This proline mutation has been shown to increase the single CBM Tm by 3-4° C. The proline mutation is not near the other mutations, the N- or C-termini or the ligand binding site.

Characterization of the Hexameric Variants

The expression, purification and characterization results are shown in Table 2. Based on these results, HEX6 and HEX17 were taken forward. The positions of the HEX17 mutations on the hexamer are shown in FIG. 5.

TABLE 2

| Name | Mutations | Solubility | Purification | Thermostability | NearUV CD | Biacore | IL-8 assay |
|---|---|---|---|---|---|---|---|
| Hex1 | L170T/V239A/V246G/I286A/Y292E/S342D/L348D/R403K | Red | N/A | N/A | N/A | N/A | N/A |
| Hex2 | V239A/V246G/I286A/Y292E/S342D/R403K (designed but not made) | | | | | | |
| Hex3 | V239A/V246G/I286A/S342D/R403K | Red | N/A | N/A | N/A | N/A | N/A |
| Hex4 | V239A/V246G/S342D | Yellow | Red | N/A | N/A | N/A | N/A |
| Hex5 | V239A/V246G/R403K | Green | Yellow | Yellow | N/A | N/A | N/A |
| Hex6 | V239A/V246G/S342D/R403K | Green | Green | Yellow | Green | Green | Yellow |
| Hex7 to 16 | Note: These constructs are different combinations of the Hex6 mutations and were designed as a back-up in case Hex6 failed | | | | | | |
| Hex17 | A162P/V239A/V246G/S342D/R403K | Green | Green | Green' | Green | Green | reduced IL-8 |

Table 2. Qualitative summary of the biophysical characterizations of the hexameric Sp2CBMTD variants. Colour coding is from green to red, where green indicates that the variant closely resembles its WT counterpart for that particular characteristic and pale green (green') or yellow indicate increasing degrees of differences. Red or orange indicate significant differences. N/A: these characterizations were not performed due to poor solubility/purity of the protein. N/D: not determined.

Example 1: Inflammatory Mediators

Aim: To measure the innate immune response of mCBM-treated human lung epithelial cells (A549) by analysing levels of inflammatory mediators over time.

Administration of Sp2CBMTD to mammalian cells stimulated a pro-inflammatory response both in vitro and in vivo[1,2]. To determine whether this was still observed with modified hexameric sialic acid binding molecules, mammalian A549 cells were stimulated by the addition of 10 μg of biologic (Sp2CBMTD (aka SpOrig), HEX6 or HEX17 and cell culture medium was harvested at specific time-points post administration. The concentrations of inflammatory mediators were measured both by ELISA and a multiplex assay.

Human IL-8 (benchmark cytokine for the study) response using a human 1× Mouse CXCL1/KC Quantikine ELISA Kit (R&D BioSystems). The concentration levels of IL-8 from stimulated A549 cells are shown in FIG. 6. It is evident that when A549 cells are stimulated with the modified hexamer HEX17, IL-8 levels are significantly lower than when compared to Sp2CBMTD (aka SpOrig), or Hex6-stimulated cells.

Inflammatory mediator response using a Human Cytokine 12-plex Assay (Bio-Plex Pro™ Bio-Rad). FIG. 7 demonstrates the analysis of 12 inflammatory mediators from culture medium after A549 cell stimulation by Sp2CBMTD (WT, aka SpOrig), HEX6 and HEX17 (variants) at specific time points (6 h, 24 h, 48 h). Prior to analysis, samples were thawed and diluted 1:4 in PBS before using a human HS Cytokine-12 plex assay (R&D Systems). The data indicates that:
  HEX17 affects the levels of almost all the cytokines tested compared to SpOrig and HEX6. There is a significant reduction in observed concentration (pg/ml) with analytes IL-6, IL-8, GM-CSF and IFN-gamma at 48 h when compared to SpOrig and HEX6.
  When compared to control at 48 h, HEX17 appears to cause an increase in the level of all cytokines tested with the exception of IL-5, and VEGF (yet to be confirmed).
  HEX6 only showed reduced IL-6 stimulation compared to SpOrig at 48 h.

Example 2: In Vivo PR8 Mouse Data

The objective of the study was to assess the efficacy of Sp2CBMTD (SpOrig) and its variants, in a mouse model of lethal influenza infection. Each of the candidate proteins were also administered in the absence of an influenza infection to assess whether they alone, caused any morbidity or mortality.

Survival, Clinical Scores and Weight Loss.

The results show that none of CBM2 (HEX17), CBM3 (HEX6) or CBM4 (WT, SpOrig) caused any overt morbidity or mortality alone. Administration of a single 100 μg dose of either CBM2 (HEX17), CBM3 (HEX6) and CBM4 (WT, SpOrig) one day prior to a lethal challenge with PR8 influenza virus elicited protection against PR8 infection, with greatest efficacy seen with HEX17 (100% survival), followed by SpOrig and then HEX6 (FIG. 8). Clinical scores were also lower with HEX17 compared to SpOrig and HEX6 (FIG. 9). Mice from single high dose treated groups that survived all lost weight at peak infection but soon recovered, in contrast to untreated, infected mice (FIG. 10).

Anti-mCBM Antibody Analysis of Lung Homogenates and Sera Tissue from a PR8-Challenged Mouse Study.

The objective of this study was to determine whether modified immunogenic epitopes of the modified variants of Sp2CBMTD (SpOrig) demonstrated reduced antibody levels in mice in a PR8-challenged study (it should be noted that epitopes were modified based on human MHC-class II binding information). For this, survived mice from PR8-challenged study were culled at Day 21 with lung and sera harvested and tested for anti-mCBM antibodies—IgG, IgA, IgE and IgM against coated antigen SpOrig (1 μg/well) in an ELISA format. The data shown in FIG. 11 indicated that:
  The modified protein HEX17 did show a significant ($p<0.05$) reduction in mouse lung IgM levels compared to SPORIG. Due to only one surviving mouse for HEX6 treatment, only HEX17 and SPORIG data was statistically analysed.
  There is some indication of a slight downward trend of antibody levels in mice (lung IgA and IgM) that were treated with the modified CBMs compared to SpOrig.

Example 3: The Effect of Repeat Intranasal Dosing of mCBMs, Sp2CBMTD and HEX17, in the Mouse The objective of this study was to assess the clinical effect and immune response of repeat dosing of both Sp2CBMTD (SpOrig) and HEX17 in mice over time.

Experimental Procedures

Intranasal Dosing.

On Days 1, 15 and 29, cohorts of mice (10F, 10M BALB/c mice per agent) were dosed with 20 μg of either sterile PBS, Sp2CBMTD or HEX17 via the intranasal route, under recoverable gaseous anaesthesia (isoflurane/oxygen mix), at a fixed volume of 40 μL.

Body Weights and Post-Dose Observations.

All mice were weighed twice weekly from Day −1 until the end of the study (Day 35). Post-dose observations were recorded every 15 min for the first 2 h after dose administration and then every 30 min for the next 6 h.

Analysis of Tissue Samples.

Mouse tissue (serum and bronchoalveolar lavage (BAL)) were tested for anti-CBM antibody responses (IgG, IgA and IgM) against either Sp2CBMTD or HEX17 as coating antigens (1 μg/well) in an ELISA format. Absorbance readings at $OD_{450nm}$ (reference background $OD_{620nm}$) were measured for each sample after reaction of an HRP-conjugated detection antibody with its chromogenic substrate 3,3',5,5'-tetramethylbenzidine (TMB), to the different antibody types.

Results:

Clinical Scores.

Further studies into the effect of repeat intranasal dosing of Sp2CBMTD and Hex17 in mice reveals that neither molecule had any significant effect on bodyweight or food consumption. Further, at later doses, HEX17 appears to be better tolerated, with some (resolving) clinical signs (including piloerection, hunched posture, underactivity, partially closed eyes and irregular breathing) being noted for a limited period after Sp2CBMTD administration.

Anti-mCBM Antibody Analysis of Serum and BAL Tissue from Mice.

The data shown in FIG. 12 indicated that after 35 days, where mice were given 3 doses of 20 μg CBM every two weeks between Days 1 and 29, an adaptive immune response was induced to both CBMs. HEX17 (an example of a modified or "de-immunized" CBM where epitopes are modified based on human MHC-class II binding information as described previously) demonstrated a significant ($p<0.05$) reduction of IgA in both BAL and serum tissues compared to Sp2CBMTD-treated mice. This was observed against both coated antigens. The difference in IgA response between the two candidates was also significant between male and female mice. The difference in IgG response was more evident in BAL samples than in sera. There was also a significant reduction of IgM levels from both BAL and serum samples when tested against Sp2CBMTD, but this was not significant in HEX17-coated plates.

The invention claimed is:

1. A sialic acid binding molecule comprising the following sequence:

(SEQ ID NO: 28)
GAMVIEKEDVETNASNGQRVDLSSELDKLKKLENATVHMEFKPDPKAPA

FYNLFSVSSATKKDEYFTMAVYNNTATLEGRGSDGKQFYNNYNDAPLK

VKPGQWNSVTFTVEKPTAELPKGRARLYVNGGLSRTSLRSGNFIKDMPD

VTHVQIGATKRANNTVWGSNLQIRNLTVYNRALTPEEVQKRSGGGSGVI

EKEDVETNASNGQRVDLSSELDKLKKLENATVHMEFKPDPKAPAFYNLF

SVSSATKKDEYFTMAVYNNTATLEGRGSDGKQFYNNYNDAPLKVKPGQ

WNSVTFTVEKPTAELPKGRARLYVNGGLSRTSLRSGNFIKDMPDVTHVQI

GATKRANNTVWGSNLQIRNLTVYNRALTPEEVQKRSGGSLGVPDFESDW

FDVSSNSLYTLSHGLQRSPRRVVVEFARSSSPSTWNIVMPSYFNDGGHKG

SGAQVEVGSLNIKLGTGAAVWGTGYFGGIDNSATTRFATGYYRVRAWI.

2. A pharmaceutical composition comprising the sialic acid binding molecule according to claim 1, formulated together with one or more excipients, carriers, adjuvants and/or buffers.

3. The pharmaceutical composition of claim 2, wherein the composition is formulated for oral, mucosal or parenteral administration.

4. The pharmaceutical composition of claim 3, wherein the composition is formulated for intranasal administration or inhalation.

5. A method of preparing the pharmaceutical composition of claim 2, comprising formulating the sialic acid binding molecule together with the one or more excipients, carriers, adjuvants and/or buffers.

* * * * *

UNITED STATES PATENT AND TRADEMARK OFFICE
CERTIFICATE OF CORRECTION

PATENT NO. : 11,466,059 B2
APPLICATION NO. : 15/733350
DATED : October 11, 2022
INVENTOR(S) : Connaris et al.

It is certified that error appears in the above-identified patent and that said Letters Patent is hereby corrected as shown below:

In the Specification

Column 12, Line 49: Please correct "-----(V239A V246G)" to read -- -----CBM2 (V239A V246G)--

Column 12, Lines 66-67: Please correct "(DOI 10.10021/prot.22509)" to read --(DOI 10.1002/prot.22509)--

Signed and Sealed this
Thirtieth Day of July, 2024

Katherine Kelly Vidal
*Director of the United States Patent and Trademark Office*

SEQUENCE LISTING

```
<160> NUMBER OF SEQ ID NOS: 28

<210> SEQ ID NO 1
<211> LENGTH: 1035
<212> TYPE: PRT
<213> ORGANISM: Streptococcus pneumoniae

<400> SEQUENCE: 1

Met Ser Tyr Phe Arg Asn Arg Asp Ile Asp Ile Glu Arg Asn Ser Met
1               5                   10                  15

Asn Arg Ser Val Gln Glu Arg Lys Cys Arg Tyr Ser Ile Arg Lys Leu
                20                  25                  30

Ser Val Gly Ala Val Ser Met Ile Val Gly Ala Val Val Phe Gly Thr
            35                  40                  45

Ser Pro Val Leu Ala Gln Glu Gly Ala Ser Glu Gln Pro Leu Ala Asn
    50                  55                  60

Glu Thr Gln Leu Ser Gly Glu Ser Ser Thr Leu Thr Asp Thr Glu Lys
65                  70                  75                  80

Ser Gln Pro Ser Ser Glu Thr Glu Leu Ser Gly Asn Lys Gln Glu Gln
                85                  90                  95

Glu Arg Lys Asp Lys Gln Glu Glu Lys Ile Pro Arg Asp Tyr Tyr Ala
                100                 105                 110

Arg Asp Leu Glu Asn Val Glu Thr Val Ile Glu Lys Glu Asp Val Glu
            115                 120                 125

Thr Asn Ala Ser Asn Gly Gln Arg Val Asp Leu Ser Ser Glu Leu Asp
    130                 135                 140

Lys Leu Lys Lys Leu Glu Asn Ala Thr Val His Met Glu Phe Lys Pro
145                 150                 155                 160

Asp Ala Lys Ala Pro Ala Phe Tyr Asn Leu Phe Ser Val Ser Ser Ala
                165                 170                 175

Thr Lys Lys Asp Glu Tyr Phe Thr Met Ala Val Tyr Asn Asn Thr Ala
                180                 185                 190

Thr Leu Glu Gly Arg Gly Ser Asp Gly Lys Gln Phe Tyr Asn Asn Tyr
            195                 200                 205

Asn Asp Ala Pro Leu Lys Val Lys Pro Gly Gln Trp Asn Ser Val Thr
    210                 215                 220

Phe Thr Val Glu Lys Pro Thr Ala Glu Leu Pro Lys Gly Arg Val Arg
225                 230                 235                 240

Leu Tyr Val Asn Gly Val Leu Ser Arg Thr Ser Leu Arg Ser Gly Asn
                245                 250                 255

Phe Ile Lys Asp Met Pro Asp Val Thr His Val Gln Ile Gly Ala Thr
                260                 265                 270

Lys Arg Ala Asn Asn Thr Val Trp Gly Ser Asn Leu Gln Ile Arg Asn
            275                 280                 285

Leu Thr Val Tyr Asn Arg Ala Leu Thr Pro Glu Glu Val Gln Lys Arg
    290                 295                 300
```

```
Ser Gln Leu Phe Lys Arg Ser Asp Leu Glu Lys Lys Leu Pro Glu Gly
305                 310                 315                 320

Ala Ala Leu Thr Glu Lys Thr Asp Ile Phe Glu Ser Gly Arg Asn Gly
            325                 330                 335

Lys Pro Asn Lys Asp Gly Ile Lys Ser Tyr Arg Ile Pro Ala Leu Leu
                340                 345                 350

Lys Thr Asp Lys Gly Thr Leu Ile Ala Gly Ala Asp Glu Arg Arg Leu
            355                 360                 365

His Ser Ser Asp Trp Gly Asp Ile Gly Met Val Ile Arg Arg Ser Glu
    370                 375                 380

Asp Asn Gly Lys Thr Trp Gly Asp Arg Val Thr Ile Thr Asn Leu Arg
385                 390                 395                 400

Asp Asn Pro Lys Ala Ser Asp Pro Ser Ile Gly Ser Pro Val Asn Ile
                405                 410                 415

Asp Met Val Leu Val Gln Asp Pro Glu Thr Lys Arg Ile Phe Ser Ile
            420                 425                 430

Tyr Asp Met Phe Pro Glu Gly Lys Gly Ile Phe Gly Met Ser Ser Gln
            435                 440                 445

Lys Glu Glu Ala Tyr Lys Lys Ile Asp Gly Lys Thr Tyr Gln Ile Leu
450                 455                 460

Tyr Arg Glu Gly Glu Lys Gly Ala Tyr Thr Ile Arg Glu Asn Gly Thr
465                 470                 475                 480

Val Tyr Thr Pro Asp Gly Lys Ala Thr Asp Tyr Arg Val Val Asp
                485                 490                 495

Pro Val Lys Pro Ala Tyr Ser Asp Lys Gly Asp Leu Tyr Lys Gly Asn
                500                 505                 510

Gln Leu Leu Gly Asn Ile Tyr Phe Thr Thr Asn Lys Thr Ser Pro Phe
            515                 520                 525

Arg Ile Ala Lys Asp Ser Tyr Leu Trp Met Ser Tyr Ser Asp Asp Asp
            530                 535                 540

Gly Lys Thr Trp Ser Ala Pro Gln Asp Ile Thr Pro Met Val Lys Ala
545                 550                 555                 560

Asp Trp Met Lys Phe Leu Gly Val Gly Pro Gly Thr Gly Ile Val Leu
                565                 570                 575

Arg Asn Gly Pro His Lys Gly Arg Ile Leu Ile Pro Val Tyr Thr Thr
            580                 585                 590

Asn Asn Val Ser His Leu Asn Gly Ser Gln Ser Ser Arg Ile Ile Tyr
            595                 600                 605

Ser Asp His Gly Lys Thr Trp His Ala Gly Glu Ala Val Asn Asp
    610                 615                 620

Asn Arg Gln Val Asp Gly Gln Lys Ile His Ser Ser Thr Met Asn Asn
625                 630                 635                 640

Arg Arg Ala Gln Asn Thr Glu Ser Thr Val Val Gln Leu Asn Asn Gly
            645                 650                 655

Asp Val Lys Leu Phe Met Arg Gly Leu Thr Gly Asp Leu Gln Val Ala
            660                 665                 670

Thr Ser Lys Asp Gly Gly Val Thr Trp Glu Lys Asp Ile Lys Arg Tyr
            675                 680                 685

Pro Gln Val Lys Asp Val Tyr Val Gln Met Ser Ala Ile His Thr Met
            690                 695                 700

His Glu Gly Lys Glu Tyr Ile Ile Leu Ser Asn Ala Gly Gly Pro Lys
705                 710                 715                 720
```

```
Arg Glu Asn Gly Met Val His Leu Ala Arg Val Glu Glu Asn Gly Glu
            725                 730                 735

Leu Thr Trp Leu Lys His Asn Pro Ile Gln Lys Gly Glu Phe Ala Tyr
            740                 745                 750

Asn Ser Leu Gln Glu Leu Gly Asn Gly Glu Tyr Gly Ile Leu Tyr Glu
            755                 760                 765

His Thr Glu Lys Gly Gln Asn Ala Tyr Thr Leu Ser Phe Arg Lys Phe
            770                 775                 780

Asn Trp Asp Phe Leu Ser Lys Asp Leu Ile Ser Pro Thr Glu Ala Lys
785                 790                 795                 800

Val Lys Arg Thr Arg Glu Met Gly Lys Gly Val Ile Gly Leu Glu Phe
                    805                 810                 815

Asp Ser Glu Val Leu Val Asn Lys Ala Pro Thr Leu Gln Leu Ala Asn
                    820                 825                 830

Gly Lys Thr Ala Arg Phe Met Thr Gln Tyr Asp Thr Lys Thr Leu Leu
                    835                 840                 845

Phe Thr Val Asp Ser Glu Asp Met Gly Gln Lys Val Thr Gly Leu Ala
            850                 855                 860

Glu Gly Ala Ile Glu Ser Met His Asn Leu Pro Val Ser Val Ala Gly
865                 870                 875                 880

Thr Lys Leu Ser Asn Gly Met Asn Gly Ser Glu Ala Ala Val His Glu
                    885                 890                 895

Val Pro Glu Tyr Thr Gly Pro Leu Gly Thr Ser Gly Glu Glu Pro Ala
                    900                 905                 910

Pro Thr Val Glu Lys Pro Glu Tyr Thr Gly Pro Leu Gly Thr Ser Gly
                    915                 920                 925

Glu Glu Pro Ala Pro Thr Val Glu Lys Pro Glu Tyr Thr Gly Pro Leu
            930                 935                 940

Gly Thr Ala Gly Glu Glu Ala Ala Pro Thr Val Glu Lys Pro Glu Phe
945                 950                 955                 960

Thr Gly Gly Val Asn Gly Thr Glu Pro Ala Val His Glu Ile Ala Glu
                    965                 970                 975

Tyr Lys Gly Ser Asp Ser Leu Val Thr Leu Thr Thr Lys Glu Asp Tyr
                    980                 985                 990

Thr Tyr Lys Ala Pro Leu Ala Gln Gln Ala Leu Pro Glu Thr Gly Asn
                    995                 1000                1005

Lys Glu Ser Asp Leu Leu Ala Ser Leu Gly Leu Thr Ala Phe Phe
            1010                1015                1020

Leu Gly Leu Phe Thr Leu Gly Lys Lys Arg Glu Gln
            1025                1030                1035

<210> SEQ ID NO 2
<211> LENGTH: 185
<212> TYPE: PRT
<213> ORGANISM: Streptococcus pneumoniae

<400> SEQUENCE: 2

Val Ile Glu Lys Glu Asp Val Glu Thr Asn Ala Ser Asn Gly Gln Arg
1               5                   10                  15

Val Asp Leu Ser Ser Glu Leu Asp Lys Leu Lys Lys Leu Glu Asn Ala
            20                  25                  30

Thr Val His Met Glu Phe Lys Pro Asp Ala Lys Ala Pro Ala Phe Tyr
            35                  40                  45

Asn Leu Phe Ser Val Ser Ser Ala Thr Lys Lys Asp Glu Tyr Phe Thr
50                  55                  60
```

```
Met Ala Val Tyr Asn Asn Thr Ala Thr Leu Glu Gly Arg Gly Ser Asp
 65                  70                  75                  80

Gly Lys Gln Phe Tyr Asn Asn Tyr Asn Asp Ala Pro Leu Lys Val Lys
                 85                  90                  95

Pro Gly Gln Trp Asn Ser Val Thr Phe Thr Val Glu Lys Pro Thr Ala
            100                 105                 110

Glu Leu Pro Lys Gly Arg Val Arg Leu Tyr Val Asn Gly Val Leu Ser
        115                 120                 125

Arg Thr Ser Leu Arg Ser Gly Asn Phe Ile Lys Asp Met Pro Asp Val
    130                 135                 140

Thr His Val Gln Ile Gly Ala Thr Lys Arg Ala Asn Asn Thr Val Trp
145                 150                 155                 160

Gly Ser Asn Leu Gln Ile Arg Asn Leu Thr Val Tyr Asn Arg Ala Leu
                165                 170                 175

Thr Pro Glu Glu Val Gln Lys Arg Ser
            180                 185

<210> SEQ ID NO 3
<211> LENGTH: 781
<212> TYPE: PRT
<213> ORGANISM: Vibrio cholerae

<400> SEQUENCE: 3

Met Arg Phe Lys Asn Val Lys Lys Thr Ala Leu Met Leu Ala Met Phe
  1               5                  10                  15

Gly Met Ala Thr Ser Ser Asn Ala Ala Leu Phe Asp Tyr Asn Ala Thr
             20                  25                  30

Gly Asp Thr Glu Phe Asp Ser Pro Ala Lys Gln Gly Trp Met Gln Asp
         35                  40                  45

Asn Thr Asn Asn Gly Ser Gly Val Leu Thr Asn Ala Asp Gly Met Pro
     50                  55                  60

Ala Trp Leu Val Gln Gly Ile Gly Gly Arg Ala Gln Trp Thr Tyr Ser
 65                  70                  75                  80

Leu Ser Thr Asn Gln His Ala Gln Ala Ser Ser Phe Gly Trp Arg Met
                 85                  90                  95

Thr Thr Glu Met Lys Val Leu Ser Gly Gly Met Ile Thr Asn Tyr Tyr
            100                 105                 110

Ala Asn Gly Thr Gln Arg Val Leu Pro Ile Ile Ser Leu Asp Ser Ser
        115                 120                 125

Gly Asn Leu Val Val Glu Phe Glu Gly Gln Thr Gly Arg Thr Val Leu
    130                 135                 140

Ala Thr Gly Thr Ala Ala Thr Glu Tyr His Lys Phe Glu Leu Val Phe
145                 150                 155                 160

Leu Pro Gly Ser Asn Pro Ser Ala Ser Phe Tyr Phe Asp Gly Lys Leu
                165                 170                 175

Ile Arg Asp Asn Ile Gln Pro Thr Ala Ser Lys Gln Asn Met Ile Val
            180                 185                 190

Trp Gly Asn Gly Ser Ser Asn Thr Asp Gly Val Ala Ala Tyr Arg Asp
        195                 200                 205

Ile Lys Phe Glu Ile Gln Gly Asp Val Ile Phe Arg Gly Pro Asp Arg
    210                 215                 220

Ile Pro Ser Ile Val Ala Ser Ser Val Thr Pro Gly Val Val Thr Ala
225                 230                 235                 240

Phe Ala Glu Lys Arg Val Gly Gly Gly Asp Pro Gly Ala Leu Ser Asn
```

```
                         245                 250                 255
        Thr Asn Asp Ile Ile Thr Arg Thr Ser Arg Asp Gly Ile Thr Trp
                    260                 265                 270
        Asp Thr Glu Leu Asn Leu Thr Glu Gln Ile Asn Val Ser Asp Glu Phe
                        275                 280                 285
        Asp Phe Ser Asp Pro Arg Pro Ile Tyr Asp Pro Ser Ser Asn Thr Val
                    290                 295                 300
        Leu Val Ser Tyr Ala Arg Trp Pro Thr Asp Ala Ala Gln Asn Gly Asp
        305                 310                 315                 320
        Arg Ile Lys Pro Trp Met Pro Asn Gly Ile Phe Tyr Ser Val Tyr Asp
                            325                 330                 335
        Val Ala Ser Gly Asn Trp Gln Ala Pro Ile Asp Val Thr Asp Gln Val
                        340                 345                 350
        Lys Glu Arg Ser Phe Gln Ile Ala Gly Trp Gly Gly Ser Glu Leu Tyr
                    355                 360                 365
        Arg Arg Asn Thr Ser Leu Asn Ser Gln Gln Asp Trp Gln Ser Asn Ala
                370                 375                 380
        Lys Ile Arg Ile Val Asp Gly Ala Ala Asn Gln Ile Gln Val Ala Asp
        385                 390                 395                 400
        Gly Ser Arg Lys Tyr Val Val Thr Leu Ser Ile Asp Glu Ser Gly Gly
                            405                 410                 415
        Leu Val Ala Asn Leu Asn Gly Val Ser Ala Pro Ile Ile Leu Gln Ser
                        420                 425                 430
        Glu His Ala Lys Val His Ser Phe His Asp Tyr Glu Leu Gln Tyr Ser
                    435                 440                 445
        Ala Leu Asn His Thr Thr Thr Leu Phe Val Asp Gly Gln Gln Ile Thr
        450                 455                 460
        Thr Trp Ala Gly Glu Val Ser Gln Glu Asn Asn Ile Gln Phe Gly Asn
        465                 470                 475                 480
        Ala Asp Ala Gln Ile Asp Gly Arg Leu His Val Gln Lys Ile Val Leu
                            485                 490                 495
        Thr Gln Gln Gly His Asn Leu Val Glu Phe Asp Ala Phe Tyr Leu Ala
                        500                 505                 510
        Gln Gln Thr Pro Glu Val Glu Lys Asp Leu Glu Lys Leu Gly Trp Thr
                    515                 520                 525
        Lys Ile Lys Thr Gly Asn Thr Met Ser Leu Tyr Gly Asn Ala Ser Val
                530                 535                 540
        Asn Pro Gly Pro Gly His Gly Ile Thr Leu Thr Arg Gln Gln Asn Ile
        545                 550                 555                 560
        Ser Gly Ser Gln Asn Gly Arg Leu Ile Tyr Pro Ala Ile Val Leu Asp
                            565                 570                 575
        Arg Phe Phe Leu Asn Val Met Ser Ile Tyr Ser Asp Asp Gly Gly Ser
                        580                 585                 590
        Asn Trp Gln Thr Gly Ser Thr Leu Pro Ile Pro Phe Arg Trp Lys Ser
                    595                 600                 605
        Ser Ser Ile Leu Glu Thr Leu Glu Pro Ser Glu Ala Asp Met Val Glu
        610                 615                 620
        Leu Gln Asn Gly Asp Leu Leu Leu Thr Ala Arg Leu Asp Phe Asn Gln
        625                 630                 635                 640
        Ile Val Asn Gly Val Asn Tyr Ser Pro Arg Gln Gln Phe Leu Ser Lys
                            645                 650                 655
        Asp Gly Gly Ile Thr Trp Ser Leu Leu Glu Ala Asn Asn Ala Asn Val
                        660                 665                 670
```

```
Phe Ser Asn Ile Ser Thr Gly Thr Val Asp Ala Ser Ile Thr Arg Phe
            675                 680                 685

Glu Gln Ser Asp Gly Ser His Phe Leu Leu Phe Thr Asn Pro Gln Gly
        690                 695                 700

Asn Pro Ala Gly Thr Asn Gly Arg Gln Asn Leu Gly Leu Trp Phe Ser
705                 710                 715                 720

Phe Asp Glu Gly Val Thr Trp Lys Gly Pro Ile Gln Leu Val Asn Gly
                725                 730                 735

Ala Ser Ala Tyr Ser Asp Ile Tyr Gln Leu Asp Ser Glu Asn Ala Ile
            740                 745                 750

Val Ile Val Glu Thr Asp Asn Ser Asn Met Arg Ile Leu Arg Met Pro
        755                 760                 765

Ile Thr Leu Leu Lys Gln Lys Leu Thr Leu Ser Gln Asn
770                 775                 780

<210> SEQ ID NO 4
<211> LENGTH: 182
<212> TYPE: PRT
<213> ORGANISM: Vibrio cholerae

<400> SEQUENCE: 4

Ala Leu Phe Asp Tyr Asn Ala Thr Gly Asp Thr Glu Phe Asp Ser Pro
1               5                   10                  15

Ala Lys Gln Gly Trp Met Gln Asp Asn Thr Asn Asn Gly Ser Gly Val
            20                  25                  30

Leu Thr Asn Ala Asp Gly Met Pro Ala Trp Leu Val Gln Gly Ile Gly
        35                  40                  45

Gly Arg Ala Gln Trp Thr Tyr Ser Leu Ser Thr Asn Gln His Ala Gln
    50                  55                  60

Ala Ser Ser Phe Gly Trp Arg Met Thr Thr Glu Met Lys Val Leu Ser
65                  70                  75                  80

Gly Gly Met Ile Thr Asn Tyr Tyr Ala Asn Gly Thr Gln Arg Val Leu
                85                  90                  95

Pro Ile Ile Ser Leu Asp Ser Ser Gly Asn Leu Val Val Glu Phe Glu
            100                 105                 110

Gly Gln Thr Gly Arg Thr Val Leu Ala Thr Gly Thr Ala Ala Thr Glu
        115                 120                 125

Tyr His Lys Phe Glu Leu Val Phe Leu Pro Gly Ser Asn Pro Ser Ala
    130                 135                 140

Ser Phe Tyr Phe Asp Gly Lys Leu Ile Arg Asp Asn Ile Gln Pro Thr
145                 150                 155                 160

Ala Ser Lys Gln Asn Met Ile Val Trp Gly Asn Gly Ser Ser Asn Thr
                165                 170                 175

Asp Gly Val Ala Ala Tyr
            180

<210> SEQ ID NO 5
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: MISC_FEATURE
<222> LOCATION: (3)..(3)
<223> OTHER INFORMATION: Any amino acid

<400> SEQUENCE: 5
```

```
Ala Leu Xaa Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Linker

<400> SEQUENCE: 6

Leu Gln Ala Leu Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: MISC_FEATURE
<222> LOCATION: (3)..(3)
<223> OTHER INFORMATION: Any amino acid

<400> SEQUENCE: 7

Gly Gly Xaa Ser Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Linker

<400> SEQUENCE: 8

Gly Gly Ala Leu Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Linker

<400> SEQUENCE: 9

Gly Gly Ser Leu Gly
1               5

<210> SEQ ID NO 10
<211> LENGTH: 10
<212> TYPE: PRT
<213> ORGANISM: Artificial Sequence
<220> FEATURE:
<223> OTHER INFORMATION: Linker
<220> FEATURE:
<221> NAME/KEY: MISC_FEATURE
<222> LOCATION: (3)..(3)
<223> OTHER INFORMATION: Any amino acid

<400> SEQUENCE: 10

Ala Leu Xaa Gly Ser Gly Gly Ser Gly
1               5                   10

<210> SEQ ID NO 11
```

<211> LENGTH: 10
<212> TYPE: PRT
<213> ORGANISM: Artificial Sequence
<220> FEATURE:
<223> OTHER INFORMATION: Linker

<400> SEQUENCE: 11

Leu Gln Ala Leu Gly Gly Gly Gly Ser Leu
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Ala Leu Xaa Gly Ser Gly Gly Gly Ser Gly Gly Gly Gly Ser Gly
1               5                   10                  15

<210> SEQ ID NO 13
<211> LENGTH: 438
<212> TYPE: PRT
<213> ORGANISM: Pseudomonas aeruginosa

<400> SEQUENCE: 13

Met Asn Thr Tyr Phe Asp Ile Pro His Arg Leu Val Gly Lys Ala Leu
1               5                   10                  15

Tyr Glu Ser Tyr Tyr Asp His Phe Gly Gln Met Asp Ile Leu Ser Asp
                20                  25                  30

Gly Ser Leu Tyr Leu Ile Tyr Arg Arg Ala Thr Glu His Val Gly Gly
            35                  40                  45

Ser Asp Gly Arg Val Val Phe Ser Lys Leu Glu Gly Gly Ile Trp Ser
     50                  55                  60

Ala Pro Thr Ile Val Ala Gln Ala Gly Gly Gln Asp Phe Arg Asp Val
65                  70                  75                  80

Ala Gly Gly Thr Met Pro Ser Gly Arg Ile Val Ala Ala Ser Thr Val
                85                  90                  95

Tyr Glu Thr Gly Glu Val Lys Val Tyr Val Ser Asp Ser Gly Val
                100                 105                 110

Thr Trp Val His Lys Phe Thr Leu Ala Arg Gly Gly Ala Asp Tyr Asn
            115                 120                 125

Phe Ala His Gly Lys Ser Phe Gln Val Gly Ala Arg Tyr Val Ile Pro
    130                 135                 140

Leu Tyr Ala Ala Thr Gly Val Asn Tyr Glu Leu Lys Trp Leu Glu Ser
145                 150                 155                 160

Ser Asp Gly Gly Glu Thr Trp Gly Glu Gly Ser Thr Ile Tyr Ser Gly
                165                 170                 175

Asn Thr Pro Tyr Asn Glu Thr Ser Tyr Leu Pro Val Gly Asp Gly Val
            180                 185                 190

Ile Leu Ala Val Ala Arg Val Gly Ser Gly Ala Gly Gly Ala Leu Arg
        195                 200                 205

Gln Phe Ile Ser Leu Asp Asp Gly Gly Thr Trp Thr Asp Gln Gly Asn
    210                 215                 220

Val Thr Ala Gln Asn Gly Asp Ser Thr Asp Ile Leu Val Ala Pro Ser

```
                       225                 230                 235                 240

Leu Ser Tyr Ile Tyr Ser Glu Gly Gly Thr Pro His Val Val Leu Leu
                        245                 250                 255

Tyr Thr Asn Arg Thr Thr His Phe Cys Tyr Tyr Arg Thr Ile Leu Leu
                        260                 265                 270

Ala Lys Ala Val Ala Gly Ser Gly Trp Thr Glu Arg Val Pro Val
                275                 280                 285

Tyr Ser Ala Pro Ala Ala Ser Gly Tyr Thr Ser Gln Val Val Leu Gly
                        290                 295                 300

Gly Arg Arg Ile Leu Gly Asn Leu Phe Arg Glu Thr Ser Ser Thr Thr
        305                 310                 315                 320

Ser Gly Ala Tyr Gln Phe Glu Val Tyr Leu Gly Val Pro Asp Phe
                        325                 330                 335

Glu Ser Asp Trp Phe Ser Val Ser Asn Ser Leu Tyr Thr Leu Ser
                        340                 345                 350

His Gly Leu Gln Arg Ser Pro Arg Arg Val Val Glu Phe Ala Arg
                        355                 360                 365

Ser Ser Ser Pro Ser Thr Trp Asn Ile Val Met Pro Ser Tyr Phe Asn
        370                 375                 380

Asp Gly Gly His Lys Gly Ser Gly Ala Gln Val Glu Val Gly Ser Leu
        385                 390                 395                 400

Asn Ile Arg Leu Gly Thr Gly Ala Ala Val Trp Gly Thr Gly Tyr Phe
                        405                 410                 415

Gly Gly Ile Asp Asn Ser Ala Thr Thr Arg Phe Ala Thr Gly Tyr Tyr
                        420                 425                 430

Arg Val Arg Ala Trp Ile
                        435

<210> SEQ ID NO 14
<211> LENGTH: 106
<212> TYPE: PRT
<213> ORGANISM: Pseudomonas aeruginosa

<400> SEQUENCE: 14

Val Pro Asp Phe Glu Ser Asp Trp Phe Ser Val Ser Asn Ser Leu
1               5                  10                  15

Tyr Thr Leu Ser His Gly Leu Gln Arg Ser Pro Arg Arg Val Val
                20                  25                  30

Glu Phe Ala Arg Ser Ser Ser Pro Ser Thr Trp Asn Ile Val Met Pro
                35                  40                  45

Ser Tyr Phe Asn Asp Gly Gly His Lys Gly Ser Gly Ala Gln Val Glu
        50                  55                  60

Val Gly Ser Leu Asn Ile Arg Leu Gly Thr Gly Ala Ala Val Trp Gly
65                  70                  75                  80

Thr Gly Tyr Phe Gly Gly Ile Asp Asn Ser Ala Thr Thr Arg Phe Ala
                        85                  90                  95

Thr Gly Tyr Tyr Arg Val Arg Ala Trp Ile
                100                 105

<210> SEQ ID NO 15
<211> LENGTH: 12
<212> TYPE: PRT
<213> ORGANISM: Streptococcus pneumoniae

<400> SEQUENCE: 15

Phe Tyr Asn Leu Phe Ser Val Ser Ser Ala Thr Lys
```

<210> SEQ ID NO 16
<211> LENGTH: 15
<212> TYPE: PRT
<213> ORGANISM: Streptococcus pneumoniae

<400> SEQUENCE: 16

Phe Tyr Asn Leu Phe Ser Val Ser Ser Ala Thr Lys Lys Asp Glu
1               5                   10                  15

<210> SEQ ID NO 17
<211> LENGTH: 13
<212> TYPE: PRT
<213> ORGANISM: Streptococcus pneumoniae

<400> SEQUENCE: 17

Val Arg Leu Tyr Val Asn Gly Val Leu Ser Arg Thr Ser
1               5                   10

<210> SEQ ID NO 18
<211> LENGTH: 15
<212> TYPE: PRT
<213> ORGANISM: Streptococcus pneumoniae

<400> SEQUENCE: 18

Lys Gly Arg Val Arg Leu Tyr Val Asn Gly Val Leu Ser Arg Thr
1               5                   10                  15

<210> SEQ ID NO 19
<211> LENGTH: 10
<212> TYPE: PRT
<213> ORGANISM: Streptococcus pneumoniae

<400> SEQUENCE: 19

Gly Val Leu Ser Arg Thr Ser Leu Arg Ser
1               5                   10

<210> SEQ ID NO 20
<211> LENGTH: 9
<212> TYPE: PRT
<213> ORGANISM: Streptococcus pneumoniae

<400> SEQUENCE: 20

Ile Arg Asn Leu Thr Val Tyr Asn Arg
1               5

<210> SEQ ID NO 21
<211> LENGTH: 10
<212> TYPE: PRT
<213> ORGANISM: Pseudomonas aeruginosa

<400> SEQUENCE: 21

Trp Phe Ser Val Ser Ser Asn Ser Leu Tyr
1               5                   10

<210> SEQ ID NO 22
<211> LENGTH: 9
<212> TYPE: PRT
<213> ORGANISM: Pseudomonas aeruginosa

<400> SEQUENCE: 22

Leu Ser His Gly Leu Gln Arg Ser Pro
1               5

<210> SEQ ID NO 23
<211> LENGTH: 9
<212> TYPE: PRT
<213> ORGANISM: Pseudomonas aeruginosa

<400> SEQUENCE: 23

Gly Ser Leu Asn Ile Arg Leu Gly Thr
1               5

<210> SEQ ID NO 24
<211> LENGTH: 15
<212> TYPE: PRT
<213> ORGANISM: Pseudomonas aeruginosa

<400> SEQUENCE: 24

Gly Ala Gln Val Glu Val Gly Ser Leu Asn Ile Arg Leu Gly Thr
1               5                   10                  15

<210> SEQ ID NO 25
<211> LENGTH: 15
<212> TYPE: PRT
<213> ORGANISM: Pseudomonas aeruginosa

<400> SEQUENCE: 25

Ser Asp Trp Phe Ser Val Ser Asn Ser Leu Tyr Thr Leu Ser
1               5                   10                  15

<210> SEQ ID NO 26
<211> LENGTH: 489
<212> TYPE: PRT
<213> ORGANISM: Streptococcus pneumoniae

<400> SEQUENCE: 26

Gly Ala Met Val Ile Glu Lys Glu Asp Val Thr Asn Ala Ser Asn
1               5                   10                  15

Gly Gln Arg Val Asp Leu Ser Ser Glu Leu Asp Lys Leu Lys Lys Leu
                20                  25                  30

Glu Asn Ala Thr Val His Met Glu Phe Lys Pro Asp Ala Lys Ala Pro
            35                  40                  45

Ala Phe Tyr Asn Leu Phe Ser Val Ser Ser Ala Thr Lys Lys Asp Glu
        50                  55                  60

Tyr Phe Thr Met Ala Val Tyr Asn Asn Thr Ala Thr Leu Glu Gly Arg
65                  70                  75                  80

Gly Ser Asp Gly Lys Gln Phe Tyr Asn Tyr Asn Asp Ala Pro Leu
                85                  90                  95

Lys Val Lys Pro Gly Gln Trp Asn Ser Val Thr Phe Thr Val Glu Lys
            100                 105                 110

Pro Thr Ala Glu Leu Pro Lys Gly Arg Val Arg Leu Tyr Val Asn Gly
        115                 120                 125

Val Leu Ser Arg Thr Ser Leu Arg Ser Gly Asn Phe Ile Lys Asp Met
    130                 135                 140

Pro Asp Val Thr His Val Gln Ile Gly Ala Thr Lys Arg Ala Asn Asn
145                 150                 155                 160

Thr Val Trp Gly Ser Asn Leu Gln Ile Arg Asn Leu Thr Val Tyr Asn
                165                 170                 175

Arg Ala Leu Thr Pro Glu Glu Val Gln Lys Arg Ser Gly Gly Ser
            180                 185                 190

Gly Val Ile Glu Lys Glu Asp Val Glu Thr Asn Ala Ser Asn Gly Gln
        195                 200                 205

Arg Val Asp Leu Ser Ser Glu Leu Asp Lys Leu Lys Lys Leu Glu Asn
210                 215                 220

Ala Thr Val His Met Glu Phe Lys Pro Asp Ala Lys Ala Pro Ala Phe
225                 230                 235                 240

Tyr Asn Leu Phe Ser Val Ser Ser Ala Thr Lys Lys Asp Glu Tyr Phe
            245                 250                 255

Thr Met Ala Val Tyr Asn Asn Thr Ala Thr Leu Glu Gly Arg Gly Ser
            260                 265                 270

Asp Gly Lys Gln Phe Tyr Asn Asn Tyr Asn Asp Ala Pro Leu Lys Val
        275                 280                 285

Lys Pro Gly Gln Trp Asn Ser Val Thr Phe Thr Val Glu Lys Pro Thr
290                 295                 300

Ala Glu Leu Pro Lys Gly Arg Val Arg Leu Tyr Val Asn Gly Val Leu
305                 310                 315                 320

Ser Arg Thr Ser Leu Arg Ser Gly Asn Phe Ile Lys Asp Met Pro Asp
                325                 330                 335

Val Thr His Val Gln Ile Gly Ala Thr Lys Arg Ala Asn Asn Thr Val
            340                 345                 350

Trp Gly Ser Asn Leu Gln Ile Arg Asn Leu Thr Val Tyr Asn Arg Ala
            355                 360                 365

Leu Thr Pro Glu Glu Val Gln Lys Arg Ser Gly Gly Ala Leu Gly Val
370                 375                 380

Pro Asp Phe Glu Ser Asp Trp Phe Ser Val Ser Ser Asn Ser Leu Tyr
385                 390                 395                 400

Thr Leu Ser His Gly Leu Gln Arg Ser Pro Arg Arg Val Val Val Glu
                405                 410                 415

Phe Ala Arg Ser Ser Ser Pro Ser Thr Trp Asn Ile Val Met Pro Ser
            420                 425                 430

Tyr Phe Asn Asp Gly Gly His Lys Gly Ser Gly Ala Gln Val Glu Val
            435                 440                 445

Gly Ser Leu Asn Ile Arg Leu Gly Thr Gly Ala Ala Val Trp Gly Thr
        450                 455                 460

Gly Tyr Phe Gly Gly Ile Asp Asn Ser Ala Thr Thr Arg Phe Ala Thr
465                 470                 475                 480

Gly Tyr Tyr Arg Val Arg Ala Trp Ile
                485

<210> SEQ ID NO 27
<211> LENGTH: 489
<212> TYPE: PRT
<213> ORGANISM: Artificial Sequence
<220> FEATURE:
<223> OTHER INFORMATION: Modified CBM

<400> SEQUENCE: 27

Gly Ala Met Val Ile Glu Lys Glu Asp Val Glu Thr Asn Ala Ser Asn
1               5                   10                  15

Gly Gln Arg Val Asp Leu Ser Ser Glu Leu Asp Lys Leu Lys Lys Leu
            20                  25                  30

Glu Asn Ala Thr Val His Met Glu Phe Lys Pro Asp Ala Lys Ala Pro
        35                  40                  45

Ala Phe Tyr Asn Leu Phe Ser Val Ser Ser Ala Thr Lys Lys Asp Glu
    50                  55                  60

Tyr Phe Thr Met Ala Val Tyr Asn Asn Thr Ala Thr Leu Glu Gly Arg
65                  70                  75                  80

```
Gly Ser Asp Gly Lys Gln Phe Tyr Asn Asn Tyr Asn Asp Ala Pro Leu
                85                  90                  95
Lys Val Lys Pro Gly Gln Trp Asn Ser Val Thr Phe Thr Val Glu Lys
            100                 105                 110
Pro Thr Ala Glu Leu Pro Lys Gly Arg Ala Arg Leu Tyr Val Asn Gly
        115                 120                 125
Gly Leu Ser Arg Thr Ser Leu Arg Ser Gly Asn Phe Ile Lys Asp Met
    130                 135                 140
Pro Asp Val Thr His Val Gln Ile Gly Ala Thr Lys Arg Ala Asn Asn
145                 150                 155                 160
Thr Val Trp Gly Ser Asn Leu Gln Ile Arg Asn Leu Thr Val Tyr Asn
                165                 170                 175
Arg Ala Leu Thr Pro Glu Glu Val Gln Lys Arg Ser Gly Gly Gly Ser
            180                 185                 190
Gly Val Ile Glu Lys Glu Asp Val Glu Thr Asn Ala Ser Asn Gly Gln
        195                 200                 205
Arg Val Asp Leu Ser Ser Glu Leu Asp Lys Leu Lys Lys Leu Glu Asn
    210                 215                 220
Ala Thr Val His Met Glu Phe Lys Pro Asp Ala Lys Ala Pro Ala Phe
225                 230                 235                 240
Tyr Asn Leu Phe Ser Val Ser Ser Ala Thr Lys Lys Asp Glu Tyr Phe
                245                 250                 255
Thr Met Ala Val Tyr Asn Asn Thr Ala Thr Leu Glu Gly Arg Gly Ser
            260                 265                 270
Asp Gly Lys Gln Phe Tyr Asn Asn Tyr Asn Asp Ala Pro Leu Lys Val
        275                 280                 285
Lys Pro Gly Gln Trp Asn Ser Val Thr Phe Thr Val Glu Lys Pro Thr
    290                 295                 300
Ala Glu Leu Pro Lys Gly Arg Ala Arg Leu Tyr Val Asn Gly Gly Leu
305                 310                 315                 320
Ser Arg Thr Ser Leu Arg Ser Gly Asn Phe Ile Lys Asp Met Pro Asp
                325                 330                 335
Val Thr His Val Gln Ile Gly Ala Thr Lys Arg Ala Asn Asn Thr Val
            340                 345                 350
Trp Gly Ser Asn Leu Gln Ile Arg Asn Leu Thr Val Tyr Asn Arg Ala
        355                 360                 365
Leu Thr Pro Glu Glu Val Gln Lys Arg Ser Gly Gly Ser Leu Gly Val
    370                 375                 380
Pro Asp Phe Glu Ser Asp Trp Phe Asp Val Ser Ser Asn Ser Leu Tyr
385                 390                 395                 400
Thr Leu Ser His Gly Leu Gln Arg Ser Pro Arg Arg Val Val Val Glu
                405                 410                 415
Phe Ala Arg Ser Ser Ser Pro Ser Thr Trp Asn Ile Val Met Pro Ser
            420                 425                 430
Tyr Phe Asn Asp Gly Gly His Lys Gly Ser Gly Ala Gln Val Glu Val
        435                 440                 445
Gly Ser Leu Asn Ile Lys Leu Gly Thr Gly Ala Ala Val Trp Gly Thr
    450                 455                 460
Gly Tyr Phe Gly Gly Ile Asp Asn Ser Ala Thr Thr Arg Phe Ala Thr
465                 470                 475                 480
Gly Tyr Tyr Arg Val Arg Ala Trp Ile
                485
```

<210> SEQ ID NO 28
<211> LENGTH: 489
<212> TYPE: PRT
<213> ORGANISM: Artificial Sequence
<220> FEATURE:
<223> OTHER INFORMATION: Modified CBM

<400> SEQUENCE: 28

```
Gly Ala Met Val Ile Glu Lys Glu Asp Val Glu Thr Asn Ala Ser Asn
1               5                   10                  15

Gly Gln Arg Val Asp Leu Ser Ser Glu Leu Asp Lys Leu Lys Lys Leu
            20                  25                  30

Glu Asn Ala Thr Val His Met Glu Phe Lys Pro Asp Pro Lys Ala Pro
        35                  40                  45

Ala Phe Tyr Asn Leu Phe Ser Val Ser Ser Ala Thr Lys Lys Asp Glu
    50                  55                  60

Tyr Phe Thr Met Ala Val Tyr Asn Asn Thr Ala Thr Leu Glu Gly Arg
65                  70                  75                  80

Gly Ser Asp Gly Lys Gln Phe Tyr Asn Asn Tyr Asp Ala Pro Leu
                85                  90                  95

Lys Val Lys Pro Gly Gln Trp Asn Ser Val Thr Phe Thr Val Glu Lys
            100                 105                 110

Pro Thr Ala Glu Leu Pro Lys Gly Arg Ala Arg Leu Tyr Val Asn Gly
        115                 120                 125

Gly Leu Ser Arg Thr Ser Leu Arg Ser Gly Asn Phe Ile Lys Asp Met
    130                 135                 140

Pro Asp Val Thr His Val Gln Ile Gly Ala Thr Lys Arg Ala Asn Asn
145                 150                 155                 160

Thr Val Trp Gly Ser Asn Leu Gln Ile Arg Asn Leu Thr Val Tyr Asn
                165                 170                 175

Arg Ala Leu Thr Pro Glu Glu Val Gln Lys Arg Ser Gly Gly Gly Ser
            180                 185                 190

Gly Val Ile Glu Lys Glu Asp Val Glu Thr Asn Ala Ser Asn Gly Gln
        195                 200                 205

Arg Val Asp Leu Ser Ser Glu Leu Asp Lys Leu Lys Lys Leu Glu Asn
    210                 215                 220

Ala Thr Val His Met Glu Phe Lys Pro Asp Pro Lys Ala Pro Ala Phe
225                 230                 235                 240

Tyr Asn Leu Phe Ser Val Ser Ser Ala Thr Lys Lys Asp Glu Tyr Phe
                245                 250                 255

Thr Met Ala Val Tyr Asn Asn Thr Ala Thr Leu Glu Gly Arg Gly Ser
            260                 265                 270

Asp Gly Lys Gln Phe Tyr Asn Asn Tyr Asp Ala Pro Leu Lys Val
        275                 280                 285

Lys Pro Gly Gln Trp Asn Ser Val Thr Phe Thr Val Glu Lys Pro Thr
    290                 295                 300

Ala Glu Leu Pro Lys Gly Arg Ala Arg Leu Tyr Val Asn Gly Gly Leu
305                 310                 315                 320

Ser Arg Thr Ser Leu Arg Ser Gly Asn Phe Ile Lys Asp Met Pro Asp
                325                 330                 335

Val Thr His Val Gln Ile Gly Ala Thr Lys Arg Ala Asn Asn Thr Val
            340                 345                 350

Trp Gly Ser Asn Leu Gln Ile Arg Asn Leu Thr Val Tyr Asn Arg Ala
        355                 360                 365
```

```
Leu Thr Pro Glu Glu Val Gln Lys Arg Ser Gly Gly Ser Leu Gly Val
    370             375             380

Pro Asp Phe Glu Ser Asp Trp Phe Asp Val Ser Ser Asn Ser Leu Tyr
385             390             395             400

Thr Leu Ser His Gly Leu Gln Arg Ser Pro Arg Arg Val Val Val Glu
            405             410             415

Phe Ala Arg Ser Ser Pro Ser Thr Trp Asn Ile Val Met Pro Ser
            420             425             430

Tyr Phe Asn Asp Gly Gly His Lys Gly Ser Gly Ala Gln Val Glu Val
            435             440             445

Gly Ser Leu Asn Ile Lys Leu Gly Thr Gly Ala Ala Val Trp Gly Thr
    450             455             460

Gly Tyr Phe Gly Gly Ile Asp Asn Ser Ala Thr Thr Arg Phe Ala Thr
465             470             475             480

Gly Tyr Tyr Arg Val Arg Ala Trp Ile
            485
```